United States Patent
Kawamura et al.

(10) Patent No.: US 11,678,571 B2
(45) Date of Patent: Jun. 13, 2023

(54) ORGANIC ELECTROLUMINESCENT DEVICE USING ARYL AMINE DERIVATIVE CONTAINING HETEROCYCLE

(71) Applicants: Idemitsu Kosan Co., Ltd., Tokyo (JP); JOLED Inc., Tokyo (JP)

(72) Inventors: Masahiro Kawamura, Sodegaura (JP); Emiko Kambe, Kanagawa (JP); Akifumi Nakamura, Kanagawa (JP); Yasunori Kijima, Kanagawa (JP); Tadahiko Yoshinaga, Kanagawa (JP); Shigeyuki Matsunami, Kanagawa (JP)

(73) Assignees: Idemitsu Kosan Co., Ltd., Tokyo (JP); JOLED Inc., Tokyo (JP)

(*) Notice: Subject to any disclaimer, the term of this patent is extended or adjusted under 35 U.S.C. 154(b) by 43 days.

(21) Appl. No.: 17/396,820

(22) Filed: Aug. 9, 2021

(65) Prior Publication Data

US 2021/0376247 A1 Dec. 2, 2021

Related U.S. Application Data

(63) Continuation of application No. 17/106,846, filed on Nov. 30, 2020, now Pat. No. 11,152,574, which is a
(Continued)

(30) Foreign Application Priority Data

Jun. 22, 2006 (JP) .................. 2006-172853

(51) Int. Cl.
*H01L 51/00* (2006.01)
*C09K 11/06* (2006.01)
(Continued)

(52) U.S. Cl.
CPC ......... *H10K 85/636* (2023.02); *C07D 209/86* (2013.01); *C09K 11/025* (2013.01);
(Continued)

(58) Field of Classification Search
None
See application file for complete search history.

(56) References Cited

U.S. PATENT DOCUMENTS 5,061,569 A 10/1991 VanSlyke et al.
5,891,587 A 4/1999 Hu et al.
(Continued)

FOREIGN PATENT DOCUMENTS

CN 113130828 A 7/2021
EP 0 891 121 A1 1/1999
(Continued)

OTHER PUBLICATIONS

Extended European Search Report dated Apr. 4, 2011, in European Application No. 07767148.5.
(Continued)

*Primary Examiner* — Jay Yang
*Assistant Examiner* — J. L. Yang
(74) *Attorney, Agent, or Firm* — Oblon, McClelland, Maier & Neustadt, L.L.P.

(57) ABSTRACT

A compound of formula (7) is provided (7)

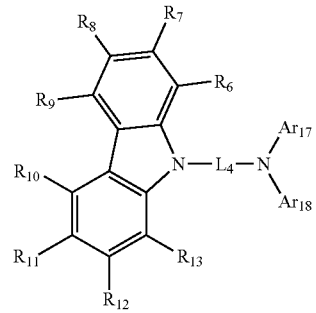

wherein $L_4$ is a linking group selected from the group consisting of:
(Continued)

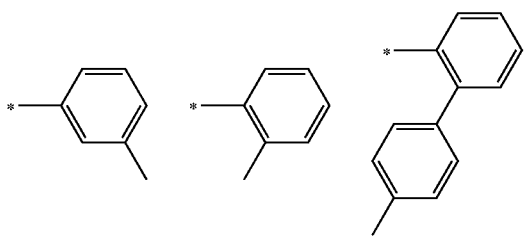

provided that an asterisk (*) indicates the position bonding to the nitrogen atom of the carbazolyl group, $R_6$ to $R_{13}$ are independently a hydrogen atom, or a phenyl group, $Ar_{17}$ is an unsubstituted phenylphenyl group, and $Ar_{18}$ is a phenylphenyl group which may be substituted by a phenyl group or a naphthyl group, or a phenyl group which may be substituted by a naphthyl group.

6 Claims, 1 Drawing Sheet

Related U.S. Application Data continuation of application No. 15/724,985, filed on Oct. 4, 2017, now Pat. No. 11,094,888, which is a continuation of application No. 14/871,055, filed on Sep. 30, 2015, now Pat. No. 9,960,360, which is a continuation of application No. 11/766,281, filed on Jun. 21, 2007, now Pat. No. 10,263,192.

(51) Int. Cl.
  *C07D 209/86* (2006.01)
  *C09K 11/02* (2006.01)
(52) U.S. Cl.
  CPC ............ *C09K 11/06* (2013.01); *H10K 85/342* (2023.02); *H10K 85/626* (2023.02); *H10K 85/633* (2023.02); *H10K 85/6572* (2023.02); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/185* (2013.01); *H10K 50/11* (2023.02); *H10K 50/14* (2023.02); *H10K 50/15* (2023.02); *H10K 50/17* (2023.02); *H10K 50/81* (2023.02); *H10K 50/82* (2023.02); *H10K 85/324* (2023.02); *H10K 85/611* (2023.02); *H10K 85/615* (2023.02); *H10K 85/622* (2023.02); *H10K 85/655* (2023.02); *H10K 2101/10* (2023.02); *H10K 2102/103* (2023.02)

(56) References Cited

U.S. PATENT DOCUMENTS

| 6,242,115 | B1 | 6/2001 | Thomson et al. |
| 6,344,283 | B1 | 2/2002 | Inoue et al. |
| 6,449,772 | B1 | 9/2002 | Donner |
| 7,507,485 | B2 | 3/2009 | Oh et al. |
| 7,981,523 | B2 | 7/2011 | Hosokawa et al. |
| 8,154,195 | B2 | 4/2012 | Nishimura et al. |
| 8,211,552 | B2 | 7/2012 | Nishimura et al. |
| 8,217,570 | B2 | 7/2012 | Kawamura et al. |
| 8,330,350 | B2 | 12/2012 | Nishimura et al. |
| 8,587,192 | B2 | 11/2013 | Nishimura et al. |
| 8,647,754 | B2 | 2/2014 | Mizuki et al. |
| 8,753,757 | B2 | 6/2014 | Hosokawa |
| 8,779,655 | B2 | 7/2014 | Nishimura et al. |
| 8,803,420 | B2 | 8/2014 | Kawamura et al. |
| 8,895,159 | B2 | 11/2014 | Mizuki et al. |
| 9,099,658 | B2 | 8/2015 | Kawamura et al. |
| 10,263,192 | B2 | 4/2019 | Kawamura et al. |
| 10,283,717 | B2 | 5/2019 | Kawamura et al. |
| 2001/0008711 | A1 | 7/2001 | Igarashi |
| 2002/0102434 | A1 | 8/2002 | Inoue et al. |
| 2002/0107405 | A1 | 8/2002 | Lin et al. |
| 2003/0048072 | A1 | 3/2003 | Ishihara et al. |
| 2003/0118866 | A1 | 6/2003 | Oh et al. |
| 2003/0143430 | A1 | 7/2003 | Kawamura et al. |
| 2003/0219625 | A1 | 11/2003 | Wolk et al. |
| 2004/0058193 | A1 | 3/2004 | Hatwar |
| 2004/0110030 | A1 | 6/2004 | Inoue et al. |
| 2004/0113547 | A1 | 6/2004 | Son et al. |
| 2005/0142384 | A1 | 6/2005 | Itai |
| 2006/0043858 | A1 | 3/2006 | Ikeda et al. |
| 2006/0043859 | A1 | 3/2006 | Fukuoka et al. |
| 2007/0075635 | A1 | 4/2007 | Yabunouchi et al. |
| 2007/0215867 | A1 | 9/2007 | Kawakami et al. |
| 2007/0215889 | A1 | 9/2007 | Kawakami et al. |
| 2007/0252516 | A1 | 11/2007 | Kondakova et al. |
| 2007/0278938 | A1 | 12/2007 | Yabunouchi et al. |
| 2007/0287029 | A1 | 12/2007 | Kawamura et al. |
| 2008/0014464 | A1 | 1/2008 | Kawamura et al. |
| 2008/0108811 | A1 | 5/2008 | Yabunouchi et al. |
| 2009/0045731 | A1 | 2/2009 | Nishimura et al. |
| 2009/0058261 | A1 | 3/2009 | Kawakami et al. |
| 2009/0174313 | A1 | 7/2009 | Nishimura et al. |
| 2009/0278445 | A1 | 11/2009 | Jen et al. |
| 2010/0141119 | A1 | 6/2010 | Yabunouchi et al. |
| 2010/0244693 | A1 | 9/2010 | Kawamura et al. |
| 2012/0187826 | A1 | 7/2012 | Kawamura et al. |
| 2012/0256172 | A1 | 10/2012 | Ito et al. |
| 2015/0162553 | A1 | 6/2015 | Kim et al. |
| 2019/0288220 | A1 | 9/2019 | Kim et al. |
| 2020/0335705 | A1 | 10/2020 | Song et al. |
| 2021/0202858 | A1 | 7/2021 | Shin et al. |
| 2021/0202860 | A1 | 7/2021 | Shin et al. |

FOREIGN PATENT DOCUMENTS

| EP | 1 610 594 | A1 | 12/2005 |
| EP | 1 880 990 | A1 | 1/2008 |
| EP | 3 846 242 | A1 | 7/2021 |
| JP | H 05-10066 | A | 1/1993 |
| JP | 11-144873 | A | 5/1999 |
| JP | 11-288783 | A | 10/1999 |
| JP | 11-329737 | A | 11/1999 |
| JP | 2000-302756 | A | 10/2000 |
| JP | 2002-241352 | A | 8/2002 |
| JP | 2003-171366 | A | 6/2003 |
| JP | 2004-178896 | A | 6/2004 |
| JP | 2004-262761 | A | 9/2004 |
| JP | 2004-307412 | A | 11/2004 |
| JP | 2004-345960 | | 12/2004 |
| JP | 2005-44802 | A | 2/2005 |
| JP | 2005-116247 | A | 4/2005 |
| JP | 2005-166680 | | 6/2005 |
| JP | 2005-289914 | A | 10/2005 |
| JP | 2006-16384 | | 1/2006 |
| JP | 2006-56841 | | 3/2006 |
| JP | 2007-110093 | A | 4/2007 |
| JP | 2007-220721 | A | 8/2007 |
| JP | 2008-524848 | A | 7/2008 |
| JP | 2012-074707 | A | 4/2012 |
| KR | 10-2005-0012132 | A | 1/2005 |
| KR | 10-2006-0053119 | A | 5/2006 |
| KR | 10-2007-0091291 | A | 9/2007 |
| KR | 10-2020-0065952 | A | 6/2020 |
| KR | 10-2169832 | B1 | 10/2020 |
| KR | 10-2169834 | B1 | 10/2020 |
| KR | 10-2021-0086165 | A | 7/2021 |
| KR | 10-2021-0095562 | A | 8/2021 |
| KR | 10-2021-0110141 | A | 9/2021 |
| WO | WO 1998/30071 | A1 | 7/1998 |
| WO | WO 2004/018587 | | 3/2004 |

(56) References Cited

FOREIGN PATENT DOCUMENTS

| WO | WO 2004/091262 | 10/2004 |
| WO | WO 2006/006505 A1 | 1/2006 |
| WO | WO 2006/019270 A1 | 2/2006 |
| WO | WO 2006/045201 A2 | 5/2006 |
| WO | WO 2006/046441 A1 | 5/2006 |
| WO | WO 2006077130 A1 | 7/2006 |
| WO | WO 2007/043354 A1 | 4/2007 |
| WO | WO 2020/241580 A1 | 12/2020 |

OTHER PUBLICATIONS

Office Action dated Dec. 16, 2011 in European Patent Application No. 07 767 148.5-2203.
Observations by a Third Party issued Nov. 22, 2012 in Japanese Patent Application No. 2008-522454.
Office Action dated Jul. 2, 2013, in Japanese Patent Application No. 2008-522454.
Office Action dated Dec. 17, 2013 in Korean Patent Application No. 10-2008-7030995.
Machine English translation of JP 2004-178896 A. Nov. 15, 2014.
Machine English translation of JP 2000-302756 A. Aug. 15, 2012.
Koene et al., "Asymmetric Triaryldiamines as Thermally Stable Hole Transporting Layers for Organic-Light-Emitting Devices", Chem. Mater. 10:2235-2250 (1998).
Chou, M-Y et al., "Electropolymerization of Starburst Triarylamines and Their Application to Electrochromism and Electroluminescence", Chem. Mater. 16:654-661 (2004).
Machine English translation JP 2005116247 A. Mar. 9, 2010.

ORGANIC ELECTROLUMINESCENT DEVICE USING ARYL AMINE DERIVATIVE CONTAINING HETEROCYCLE

CROSS REFERENCE TO RELATED APPLICATIONS

This application is a continuation application of prior U.S. application Ser. No. 17/106,846, filed Nov. 30, 2020, now allowed; which is a continuation of prior U.S. application Ser. No. 15/724,985, filed Oct. 4, 2017, now U.S. Pat. No. 11,094,888; which is a continuation application of prior U.S. application Ser. No. 14/871,055, filed Sep. 30, 2015, now U.S. Pat. No. 9,960,360; which is a continuation application to prior U.S. application Ser. No. 11/766,281, filed Jun. 21, 2007, now U.S. Pat. No. 10,263,192, all of the disclosures which are incorporated herein by reference in its entirety. The parent application claims priority to Japanese Patent Application No. 2006-172853, filed Jun. 22, 2006, the disclosure of which is incorporated herein by reference in its entirety.

TECHNICAL FIELD

The invention relates to an organic electroluminescent device using a heterocycle-containing arylamine derivative.

BACKGROUND

An organic electroluminescent device (hereinafter, "electroluminescent" is often abbreviated as "EL") is a self-emission device by the use of the principle that a fluorescent compound emits light by the recombination energy of holes injected from an anode and electrons injected from a cathode when an electric field is impressed.

Since C. W. Tang et al. of Eastman Kodak Co. reported a low-voltage driven organic EL device in the form of a stacked type device (Non-Patent Document 1), studies on organic EL devices wherein organic materials are used as the constituent materials has actively conducted.

In the organic EL device reported by Tang et al., tris(8-hydroxyquinolinol)aluminum is used for an emitting layer, and a triphenyldiamine derivative is used for a hole-transporting layer. The advantages of the stack structure are to increase injection efficiency of holes to the emitting layer, to increase generation efficiency of excitons generated by recombination by blocking electrons injected in the cathode, to confine the generated excitons in the emitting layer, and so on.

Like this example, as the structure of the organic EL device, a two-layered type of a hole-transporting (injecting) layer and an electron-transporting emitting layer, and a three-layered type of a hole-transporting (injecting) layer, an emitting layer and an electron-transporting (injecting) layer are widely known. In such stack structure devices, their device structures and fabrication methods have been contrived to increase recombination efficiency of injected holes and electrons.

As the hole-injecting material used in an organic EL device, a material having a phenylenediamine structure is known from Patent Documents 1 and 2 and has heretofore been used widely. As the hole-transporting material, an arylamine material containing a bendizine structure described in Patent Documents 3 and 4 has been used.

Patent Documents 5 to 7 disclose a carbazole-containing arylamine compound. The compound increases luminous efficiency when used as a hole-transporting material, but has such a disadvantage that the driving voltage significantly increases which results in an extremely shortened device life.

For effective injection of holes from an anode to an emitting layer, Patent Document 8 discloses a device having two or more hole-injecting/transporting layers having ionization potential values which are set in a stepwise manner. The material described in Patent Document 8 is not satisfactory in respect both of luminous efficiency and device life.

Patent Document 1: JP-A-H8-291115
Patent Document 2: JP-A-2000-309566
Patent Document 3: U.S. Pat. No. 5,061,569
Patent Document 4: JP-A-2001-273978
Patent Document 5: U.S. Pat. No. 6,242,115
Patent Document 6: JP-A-2000-302756
Patent Document 7: JP-A-H11-144873
Patent Document 8: JP-A-H6-314594
Non-patent Document 1: C. W. Tang, S. A. Vanslyke, Applied Physics Letters, 51, 913, 1987

An object of the invention is to provide a low-voltage, high-efficiency, and long-lived organic EL device.

SUMMARY OF THE INVENTION

According to the invention, the following organic EL device is provided.
1. An organic electroluminescent device comprising:
an anode, a cathode, an emitting layer formed of an organic compound and interposed between the cathode and the anode, and two or more layers provided in a hole-injecting/hole-transporting region between the anode and the emitting layer;
of the layers which are provided in the hole-injecting/hole-transporting region, a layer which is in contact with the emitting layer containing a compound represented by the formula (1); and
of the layers which are provided in the hole-injecting/hole-transporting region, a layer which is interposed between the anode and the layer which is in contact with the emitting layer containing an amine derivative represented by the formula (2).

(1)

wherein Z is a substituted or unsubstituted nitrogen-containing heterocyclic group; $L_1$ is a linking group formed by bonding of 1 to 4 divalent aromatic groups which each may have a substituent; and $Ar_1$ and $Ar_2$ are independently an aromatic hydrocarbon ring group or an aromatic heterocyclic group which may have a substituent.

(2)

wherein $L_2$ is a substituted or unsubstituted arylene group having 10 to 40 nucleus carbon atoms; and $Ar_3$ to $Ar_6$ are independently a substituted or unsubstituted aromatic hydrocarbon ring group having 6 to 60 nucleus carbon atoms or a substituted or unsubstituted aromatic heterocyclic group having 6 to 60 nucleus atoms.

2. The organic electroluminescent device according to 1, wherein the amine derivative is a compound represented by the following formula (3).

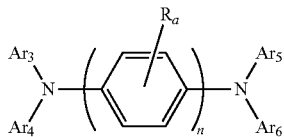

(3)

wherein $Ar_3$ to $Ar_6$ are independently a substituted or unsubstituted aromatic hydrocarbon ring group having 6 to 60 nucleus carbon atoms or a substituted or unsubstituted aromatic heterocyclic group having 6 to 60 nucleus atoms; $R_a$ is a substituent; and n is an integer of 2 to 4.

3. The organic electroluminescent device according to 2, wherein the amine derivative is a compound represented by the following formula (4).

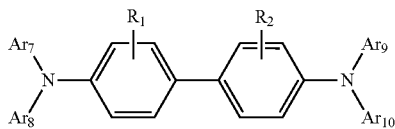

(4)

wherein $R_1$ and $R_2$ are independently a substituent and may be bonded to each other to form a saturated or unsaturated ring; and $Ar_7$ to $Ar_{40}$ are independently a substituted or unsubstituted aromatic hydrocarbon ring group having 6 to 60 nucleus carbon atoms or a substituted or unsubstituted aromatic heterocyclic group having 6 to 60 nucleus carbon atoms.

4. The organic electroluminescent device according to 3, wherein at least one of $Ar_7$ to $Ar_{10}$ in the formula (4) is a substituted or unsubstituted biphenyl group.

5. The organic electroluminescent device according to 2, wherein the amine derivative is a compound represented by the following formula (5).

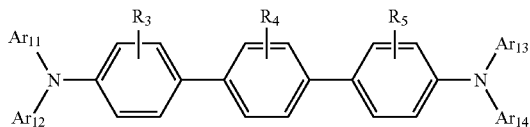

(5)

wherein $R_3$ to $R_5$ are independently a substituent and may be bonded to each other to form a saturated or unsaturated ring; and $Ar_{11}$ to $Ar_{14}$ are independently a substituted or unsubstituted aromatic hydrocarbon ring having 6 to 60 nucleus carbon atom or a substituted or unsubstituted aromatic heterocyclic group having 6 to 60 nucleus atoms.

6. The organic electroluminescent device according to 5, wherein at least one of $Ar_{11}$ to $Ar_{14}$ in the formula (5) is a substituted or unsubstituted biphenyl group.

7. The organic electroluminescent device according to any one of 1 to 6, wherein the compound represented by the formula (1) is a compound represented by the following formula (6).

(6)

wherein Cz is a substituted or unsubstituted carbozolyl group; $L_3$ is a linking group formed by bonding of 1 to 4 divalent aromatic groups which each may have a substituent; and $Ar_{15}$ and $Ar_{16}$ are independently an aromatic hydrocarbon ring group or an aromatic heterocyclic group which may have a substituent.

8. The organic electroluminescent device according to any one of 1 to 7, wherein the compound represented by the formula (1) is a compound represented by the following formula (7).

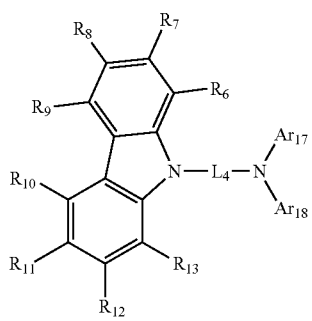

(7)

wherein $Ar_{17}$ and $Ar_{18}$ are independently an aromatic hydrocarbon ring group or an aromatic heterocyclic group which may have a substituent; and $R_6$ to $R_{13}$ are independently a hydrogen atom, a halogen atom, an alkyl group, an aralkyl group, an alkenyl group, a cyano group, an amino group, an acyl group, an alkoxycarbonyl group, a carboxyl group, an alkoxy group, an aryloxy group, an alkylsulfonyl group, a hydroxy group, an amide group, an aromatic hydrocarbon ring group or an aromatic heterocyclic group, which may further be substituted; adjacent atoms or groups represented by $R_6$ to $R_{13}$ may form a ring; and $L_4$ is a linking group formed by bonding of 1 to 4 divalent aromatic groups which each may have a substituent.

9. The organic electroluminescent device according to 8, wherein the compound represented by the formula (7) is a compound represented by the following formula (8).

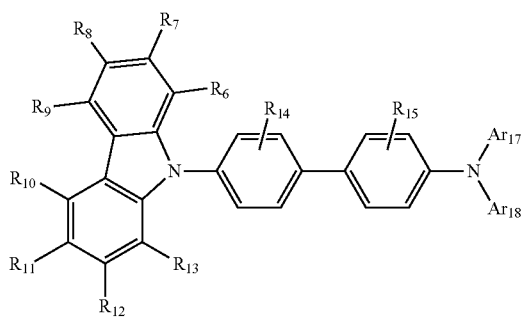

(8)

wherein $Ar_{17}$ and $Ar_{18}$ are independently an aromatic hydrocarbon group or an aromatic heterocyclic group, which may have a substituent; $R_6$ to $R_{15}$ are independently a hydrogen atom, a halogen atom, an alkyl group, an aralkyl group, an alkenyl group, a cyano group, an amino group, an acyl group, an alkoxycarbonyl group, a carboxyl group, an alkoxy group, an aryloxy group, an alkylsulfonyl group, a hydroxy group, an amide group, an aromatic hydrocarbon ring group or an aromatic heterocyclic group, which may further be substituted; and adjacent atoms or groups represented by $R_6$ to $R_{15}$ may form a ring.

10. The organic electroluminescent device according to any one of 1 to 9, wherein, of the layers which are provided in the hole-injecting/hole-transporting region, the layer which is in contact with the anode contains an acceptor material.

11. The organic electroluminescent device according to any one of 1 to 10, which emits blue light.

According to the technology of the invention, a low-voltage, high-efficiency, and long-lived an organic EL device can be realized by the used of a material with a specific structure.

BEST MODE FOR CARRYING OUT THE INVENTION

The organic EL device of the invention has at least an emitting layer formed an organic compound between the anode and the cathode, and has two or more layers in a hole-transporting/injecting region between the anode and the cathode.

Figure 1:
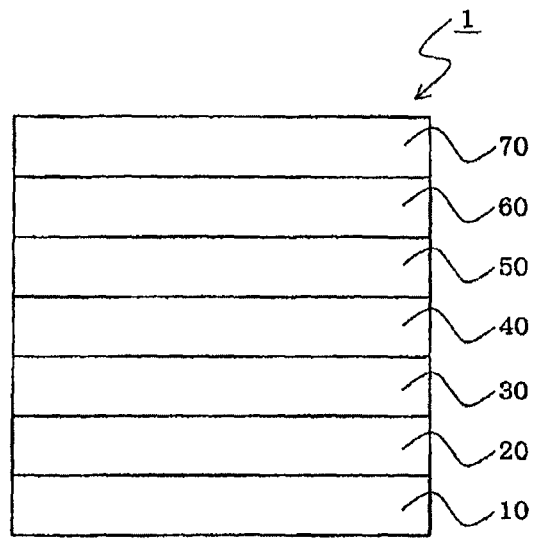
FIG. 1 is a schematic cross-sectional view showing an embodiment of an organic EL device according to the invention.

FIG. 1 is a schematic cross-sectional view of one embodiment of the organic EL device of the invention.

In the organic EL device 1, an anode 10, a hole-injecting layer 20, a hole-transporting layer 30, an emitting layer 40, an electron-transporting layer 50, an electron-injecting layer 60 and a cathode 70 are stacked on a substrate (not shown) in this order.

In the invention, the hole-injecting layer 20 and the hole-transporting layer 30, which are the layers present in the hole-injecting/transporting region, satisfy the following requirements (A) and (B).

(A) The layer which is in contact with the emitting layer (hole-transporting layer 30) contains a compound represented by the following formula (1).

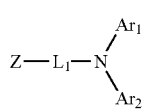  (1)

(B) The layer which is provided between the anode and the layer which is in contact with the emitting layer (hole-injecting layer 20) contains an amine derivative represented by the following formula (2).

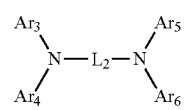  (2)

By the provision of a layer containing a specific compound at a prescribed position in the hole-injecting/hole-transporting region, the device exhibits a high luminous efficiency and a prolonged device life at a low voltage. The reason therefor is considered as follows. Due to the combined use of the compound represented by the formula (1) and the amine derivative represented by the formula (2), the compound represented by the formula (1) exhibits its inherent property of enhancing the luminous efficiency of the device, and uniquely facilitates injection of holes, thereby significantly increasing the number of holes to be injected into the emitting layer, and the layer of the compound represented by the formula (1) prevents electrons from reaching the layer of the derivative represented by the formula (2).

In the formula (1), Z is a substituted or unsubstituted heterocyclic group.

Preferred examples include pyrrole, imidazole, pyrazole, triazole, oxadiazole, pyridine, pyradine, triazine, pyrimidine, carbazole, azacarbazole, diazacarbazole, indole, benzimidazole, imidazopyridine, and indolysine.

Imidazole, carbazole, indole, indolysine, imidazopyridine, pyridine, pyrimidine and triazine are still more preferable.

As the substituent for Z, a hydrogen atom, a halogen atom (fluorine, chlorine, bromine, or iodine), an alkyl group (e.g. a linear or branched alkyl having 1 to 6 carbon atoms such as methyl and ethyl; a cycloalkyl group having 5 to 8 carbon atoms such as cyclopentyl and cyclohexyl), an aralkyl group (e.g. an aralkyl group having 7 to 13 carbon atoms such as benzyl and phenethyl), an alkenyl group (e.g. a linear or branched alkenyl group having 2 to 7 carbon atoms such as vinyl and allyl), a cyano group, an amino group, in particular a tertiary amino group (e.g. a dialkylamino group having a linear or branched alkyl group having 2 to 20 carbon atoms such as diethylamino and diisopropylamino; a diarylamino group such as diphenylamino and phenylnaphthylamino; an arylalkylamino group having 7 to 20 carbon atoms such as methylphenylamino), an acyl group (e.g. a linear, branched or cyclic acyl group having a hydrocarbon group part having 1 to 20 carbon atoms such as acetyl, propionyl, benzoyl, naphthoyl), an alkoxycarbonyl group (e.g. a linear or branched alkoxycarbonyl group having 2 to 7 carbon atoms such as methoxycarbonyl and ethoxycarbonyl), a carboxy group, an alkoxy group (e.g. a linear or branched alkoxy group having 1 to 6 carbon atoms such as methoxy and ethoxy), an aryloxy group (e.g. an aryloxy group having 6 to 10 carbon atoms such as phenoxy and benzyloxy), an alkylsulfonyl group (e.g. an alkylsulfonyl group having 1 to 6 carbon atoms such as methylsulfonyl, ethylsulfonyl, propylsulfonyl, butylsulfonyl, and hexysulfonyl), a hydroxy group, an amide group (an alkylamide group having 2 to 7 carbon atoms such as methylamide, dimethylamide, and diethylamide; an arylamide group such as benzylamide and dibenzylamide), an aromatic hydrocarbon ring group (e.g. an aromatic hydrocarbon ring group formed of a monocyclic or condensed benzene ring containing two to four rings such as phenyl, naphthyl, anthryl, phenanthryl, and pyrenyl), or an aromatic heterocyclic group (e.g. an aromatic heterocyclic group formed of a 5- or 6-membered monocyclic or condensed ring containing two to three rings such as carbazolyl, pyridyl, triazyl, pyrazyl, quinoxalyl, and thienyl).

More preferred examples of the substituent for Z include a hydrogen atom, a halogen atom, an alkyl group, an alkoxy group, an aromatic hydrocarbon ring group, and an aromatic heterocyclic group.

The above-mentioned substituent may further have a substituent. Examples of such substituent include a halogen atom (fluorine, chlorine, bromine, or iodine), an alkyl group (e.g. a linear or branched alkyl group having 1 to 6 carbon atoms such as methyl and ethyl), an alkenyl group (e.g. a linear or branched alkenyl group having 1 to 6 carbon atoms such as vinyl and allyl), an alkoxycarbonyl group (e.g. a linear or branched alkoxycarbonyl group having 1 to 6 carbon atoms such as methoxycarbonyl and ethoxycarbonyl), an alkoxy group (e.g. a linear or branched alkoxy group having 1 to 6 carbon atoms such as methoxy and ethoxy), an aryloxy group (e.g. an aryloxy group having 6 to 10 carbon atoms such as phenoxy and naphthoxy), a dialkylamino group (e.g. a dialkylamino group having a linear or branched alkyl group having 2 to 20 carbon atoms such as diethylamino and diisopropylamino), a diarylamino group (e.g. a diarylamino group such as diphenylamino and phenylnaphthylamino), an aromatic hydrocarbon ring group (e.g. an aromatic hydrocarbon ring group such as phenyl), an aromatic heterocyclic group (e.g. an aromatic heterocyclic group formed of a 5- or 6-membered monocyclic ring such as thienyl and pyridyl), an acyl group (e.g. a linear or branched acyl group having 1 to 6 carbon atoms such as acetyl and propionyl), a haloalkyl group (e.g. a linear or branched haloalkyl group having 1 to 6 carbon atoms such as trifluoromethyl), and a cyano group. Of these, a halogen atom, an alkoxy group, and an aromatic hydrocarbon ring group are more preferable.

In the formula (1), $L_1$ represents a linking group formed by bonding 1 to 4 divalent aromatic groups which each may have a substituent. $L_1$ is preferably —$Ar^{1'}$—, —$Ar^{2'}$—$Ar^{3'}$—, —$Ar^{4'}$—$Ar^{5'}$—$Ar^{6'}$—, or —$Ar^{7'}$—$Ar^{8'}$—$Ar^{9'}$—$Ar^{10'}$—. $Ar^{1'}$, $Ar^{2'}$, $Ar^{3'}$, $Ar^{4'}$, $Ar^{6'}$, $Ar^{7'}$ and $Ar^{10'}$ are independently a divalent group formed of a 5- or 6-membered monocyclic or condensed aromatic ring containing two to five rings, which may be substituted. $Ar^{5'}$, $Ar^{8'}$ and $Ar^{9'}$ are independently a divalent group formed of a 5- or 6-membered monocyclic or condensed aromatic ring containing two to five rings, which may be substituted, or —$NAr^{11'}$— ($Ar^{11'}$ is a monovalent aromatic hydrocarbon ring group or an aromatic heterocyclic group which may have a substitutent).

Specific examples of $Ar^{1'}$, $Ar^{2'}$, $Ar^{3'}$, $Ar^{4'}$, $Ar^{6'}$, $Ar^{7'}$ and $Ar^{10'}$ include a divalent aromatic ring group such as phenylene, naphthylene, anthrylene, phenanthrylene, pyrenylene, perilenylene, and a divalent aromatic heterocyclic group such as pyridylene, triazylene, pyrazylene, quinoxalene, thienylene, and oxadiazolylene.

$Ar^{5'}$, $Ar^{8'}$ and $Ar^{9'}$ are divalent aromatic groups represented by the groups mentioned above as $Ar^{1'}$ or the like, or a divalent arylamine group represented by —$NAr^{11'}$— (where $Ar^{11'}$ represents a monovalent aromatic hydrocarbon ring group or an aromatic heterocyclic group which may have a substituent). Examples of $Ar^{11'}$ include a 5- or 6-membered aromatic group, such as phenyl, naphthyl, anthryl, phenanthryl, thienyl, pyridyl, and carbazolyl, which each may have a substituent.

As $Ar^{1'}$, which is the smallest linking group as $L_1$, it is preferred that $Ar^{1'}$ be a condensed ring containing three or more rings to improve the strength of the compound as well as the heat resistance of the compound derived therefrom.

It is preferred that $Ar^{2'}$, $Ar^{3'}$, $Ar^{4'}$, $Ar^{6'}$, $Ar^{7'}$ and $Ar^{10'}$ be a monocyclic or condensed ring containing two to three rings, more preferably a monocyclic or condensed ring containing two rings.

In order to improve heat resistance, $Ar^{5'}$, $Ar^{8'}$ and $Ar^{9'}$ are preferably an aromatic ring. In respect of improving amorphous property of the compound, $Ar^{5'}$, $Ar^{8'}$ and $Ar^{9'}$ are preferably —$NAr^{11'}$—. When $Ar^{5'}$, $Ar^{8'}$ and $Ar^{9'}$ are —$NAr^{11'}$—, the emission wavelength of the compound can be shifted to a longer wavelength region to obtain a desired emission wavelength readily. If one of $Ar^{8'}$ and $Ar^{9'}$ is —$NAr^{11'}$—, it is preferred that the remaining be an aromatic group.

As the substituent for $Ar^{1'}$ to $Ar^{10'}$, the same substituent as those exemplified as the substituent for Z can be given, for example. Of these, an alkyl group, an alkoxy group, an aromatic hydrocarbon ring group or an aromatic heterocyclic group are preferable.

As the substituent for $Ar^{11'}$, the same substituent as those exemplified for Z can be given, for example. Of these, an arylamino group, an aromatic hydrocarbon ring group such as phenyl and naphthyl, and an aromatic heterocyclic group such as carbazolyl group are particularly preferable.

$Ar^1$ and $Ar^2$ in the formula (1) are independently an aromatic hydrocarbon ring group or an aromatic heterocyclic group, which may have a substituent. As the aromatic hydrocarbon ring group represented by $Ar^1$ and $Ar^2$, a monocyclic or condensed benzene ring containing two to five rings can be given, for example. Specific examples include phenyl, naphthyl, anthryl, phenanthryl, pyrenyl, and perilenyl. As the aromatic heterocyclic group, a 5- or 6-membered monocyclic or condensed ring containing two to five rings can be given. Specific examples include pyridyl, triazinyl, pyradinyl, quinoxalynyl, and thienyl.

Examples of the substituent for the aromatic hydrocarbon ring group or the aromatic heterocyclic group include an alkyl group (e.g. a linear or branched alkyl group having 1 to 6 carbon atoms such as methyl and ethyl), an alkenyl group (e.g. a linear or branched alkenyl group having 1 to 6 carbon atoms such as vinyl and allyl), an alkoxycarbonyl group (e.g. a linear or branched alkoxycarbonyl group having 1 to 6 carbon atoms such as methoxycarbonyl and ethoxycarbonyl), an alkoxy group (a linear or branched alkoxy group having 1 to 6 carbon atoms such as methoxy and ethoxy), an aryloxy group (e.g. an aryloxy group having 6 to 10 carbon atoms such as phenoxy and naphthoxy), an aralkyloxy group (e.g. aryloxy group having 7 to 13 carbon atoms such as benzyloxy), a secondary or tertiary amino group (e.g. a dialkylamino group having a linear or branched alkyl group having 2 to 20 carbon atoms such as diethylamino and diisopropylamino; a diarylamino group such as diphenylamino and phenylnaphthylamino, an arylalkylamino group having 7 to 20 carbon atoms such as methylphenylamino), a halogen atom (fluorine, chlorine, bromine, or iodine), an aromatic hydrocarbon ring group (e.g. an aromatic hydrocarbon ring group having 6 to 10 carbon atoms such as phenyl and naphthyl), and an aromatic heterocyclic group (e.g. an aromatic heterocyclic group formed of a 5- or 6-membered monocyclic or condensed ring containing two rings such as thienyl and pyridyl).

Of these, an alkyl group, an alkoxy group, an alkylamino group, an arylamino group, an arylalkylamino group, a halogen atom, an aromatic hydrocarbon ring group, and an aromatic heterocyclic group are preferable. In particular, an alkyl group, an alkoxy group, and an arylamino group are preferable.

If $Ar^1$ and $Ar^2$ have a structure in which three or more aromatic groups are connected in series through two or more direct linkages, like a terphenyl group, the hole-transporting property inherent to an arylamino group represented by —$NAr^1Ar^2$ may deteriorate, and the glass transition temperature (Tg) of the compound may lower.

Therefore, in order not to impair the property of the compound of the invention, it is important that both of $Ar^1$ and $Ar^2$ be a group in which three or more aromatic groups are not connected in series through a direct linkage or short, chain-like linking group.

A preferred nitrogen-containing compound represented by the formula (1) is a carbazole derivative represented by the following formula (6).

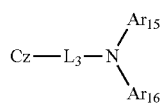
(6)

In the formula (6), Cz is a substituted or unsubstituted carbazolyl group.

Examples of the carbazolyl group represented by Cz include 1-carbazolyl, 2-carbazolyl, 3-carbazolyl, 4-carbazolyl, and N-carbazolyl. Preferably, 2-carbazolyl, 3-carbozolyl, and N-carbazolyl.

These carbozolyl groups may have a substituent. As such a substituent, the same substituent as those exemplified as the substituent for Z or the like in the formula (1) can be given.

In the formula (6), $L_3$ represents a linking group which may be formed by bonding of 1 to 4 divalent aromatic groups, which each may have a substituent. Preferred groups as $L_3$ are the same as those for $L_1$ in the formula (1).

In the formula (6), $Ar_{15}$ and $Ar_{16}$ are independently an aromatic hydrocarbon ring group or an aromatic heterocyclic group, which may have a substituent. Preferred groups as $Ar_{15}$ and $Ar_{16}$ are the same as those for $Ar_1$ and $Ar_2$ in the formula (1).

The carbazolyl derivative in the formula (6) is preferably a compound containing an N-carbazolyl group represented by the following formula (7).

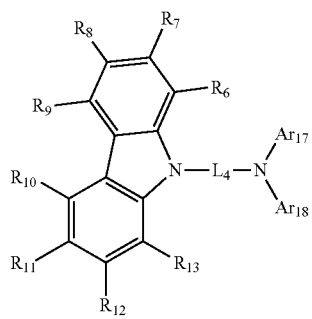
(7)

wherein $Ar_{17}$ and $Ar_{18}$ are independently an aromatic hydrocarbon ring group or an aromatic heterocyclic group which may have a substituent; an $R_6$ to $R_{13}$ are independently a hydrogen atom, a halogen atom, an alkyl group, an aralkyl group, an alkenyl group, a cyano group, an amino group, an acyl group, an alkoxycarbonyl group, a carboxyl group, an alkoxy group, an aryloxy group, an alkylsulfonyl group, a hydroxy group, an amide group, an aromatic hydrocarbon ring group or an aromatic heterocyclic group, which may further be substituted; adjacent atoms or groups represented by $R_6$ to $R_{13}$ may form a ring; and $L_4$ is a linking group formed by bonding of 1 to 4 divalent aromatic groups which each may have a substituent.

In the formula (7), the examples of the groups represented by $R_6$ to $R_{13}$ are the same as those exemplified above for Z.

Adjacent atoms or groups represented by $R_6$ to $R_{13}$ may be bonded each other to form a ring which is condensed to the N-carbazolyl group. The ring formed by bonding of the adjacent atoms or groups is normally a 5- to 8-membered ring, preferably a 5- or 6-membered ring, more preferably a 6-membered ring. This ring may either be an aromatic ring or a non-aromatic ring, but preferably an aromatic ring. The ring may be either an aromatic hydrocarbon ring or an aromatic heterocyclic ring, but preferably an aromatic hydrocarbon ring.

In the N-carbazolyl group in the formula (7), examples of the condensed ring which is formed by bonding of any of $R^6$ to $R^{13}$ to bond to the N-carbozolyl group are given below.

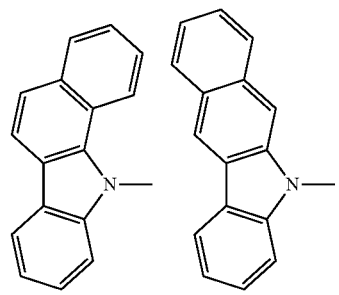

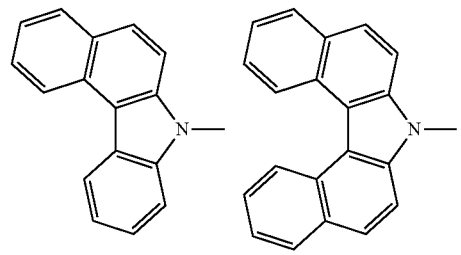

It is particularly preferred that all of $R^6$ to $R^{13}$ be a hydrogen atom (in other words, the N-carbozolyl group is unsubstituted). Alternatively, one or more of $R^6$ to $R^{13}$ are any of methyl, phenyl and methoxy, and the remaining is a hydrogen atom.

It is particularly preferred that the compound represented by the formula (7) is a compound represented by the following formula (8).

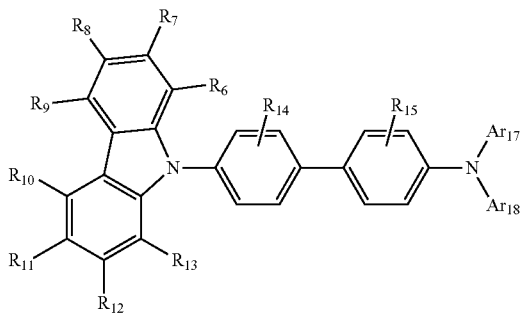

(8)

Examples of $R^6$ to $R^{15}$ are the same as those exemplified as the substitutent for Z. $R^6$ to $R^{15}$ may be bonded to each other to form a saturated or unsaturated ring. Aria and $Ar_{20}$ are independently an aromatic hydrocarbon ring group or an aromatic heterocyclic group, which may have a substitutent. Examples of $R^6$ to $R^{15}$ are the same as those for $Ar_1$ as mentioned above.

The fluorene-based compound represented by the formula (9) may also be preferably employed.

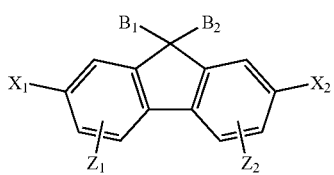

(9)

wherein $X_1$ is an N-carbazoyl group which is unsubstituted or mono- or poly-substituted by a halogen atom, an alkyl group having 1 to 10 carbon atoms, an alkoxy group having 1 to 10 carbon atoms or an aryl group having 6 to 10 carbon atoms, an N-phenoxazyl group which is unsubstituted or mono- or poly-substituted by a halogen atom, an alkyl group having 1 to 10 carbon atoms, an alkoxy group having 1 to 10 carbon atoms, or an aryl group having 6 to 10 carbon atoms, or an N-phenothiazyl group which is unsubstituted or mono- or poly-substituted by a halogen atom, an alkyl group having 1 to 10 carbon atoms, an alkoxy group having 1 to 10 carbon atoms, or an aryl group having 6 to 10 carbon atoms; $X_2$ is an N-carbazoyl group which is unsubstituted or mono- or poly-substituted by a halogen atom, an alkyl group having 1 to 10 carbon atoms, an alkoxy group having 1 to 10 carbon atoms, or an aryl group having 6 to 10 carbon atoms, an N-phenoxazyl group which is unsubstituted or mono- or poly-substituted by a halogen atom, an alkyl group having 1 to 10 carbon atoms, an alkoxy group having 1 to 10 carbon atoms, or an aryl group having 6 to 10 carbon atoms, an N-phenothiazyl group which is unsubstituted or mono- or poly-substituted by a halogen atom, an alkyl group having 1 to 10 alkyl groups, an alkoxy group having 1 to 10 carbon atoms, or an aryl group having 6 to 10 carbon atoms, or —$NAr^{21'}Ar^{22'}$ (wherein $Ar^{21'}$ and $Ar^{22'}$ are a carbocyclic aromatic group having 6 to 20 total carbon atoms or a heterocyclic aromatic group having 3 to 20 total carbon atoms which is unsubstituted or mono- or poly-substituted by a halogen atom, an alkyl group, an alkoxy group, or an aryl group.

$B_1$ and $B_2$ are a hydrogen atom, a linear, branched or cyclic alkyl group, a carbocyclic aromatic group having 5 to 20 total carbon atoms or a heterocyclic aromatic group having 3 to 20 total carbon atoms, which is unsubstituted or mono- or poly-substituted by a halogen atom, an alkyl group, an alkoxy group, or an aryl group, or an aralkyl group which is substituted or mono- or poly-substituted by a halogen atom, an alkyl group, an alkoxy group, or an aryl group or an aralkyl group which is unsubstituted or mono- or poly-substituted by a halogen atom, an alkyl group, an alkoxy group or an aryl group; and $Z_1$ and $Z_2$ are a hydrogen atom, a halogen atom, a linear, branched or cyclic alkyl group, a linear, branched or cyclic alkoxy group, or a carbocyclic aromatic group having 6 to 20 total carbon atoms or a heterocyclic aromatic group having 3 to 20 total carbon atoms, which is unsubstituted or mono- or poly-substituted by a halogen atom, an alkyl group, an alkoxy group, or an aryl group.

In the compound represented by the formula (9), $X_1$ is a substituted or unsubstituted N-carbozoyl group, a substituted or unsubstituted N-phenoxazyl group, or a substituted or unsubstituted N-phenothiazyl group. Preferably, $X_1$ is an N-carbozoyl group, an N-phenoxazyl group or an N-phenothiazyl group which is unsubstituted or mono- or poly-substituted by a halogen atom, an alkyl group having 1 to 10 carbon atoms, an alkoxy group having 1 to 10 carbon atoms, or an aryl group having 5 to 10 carbon atoms. More preferably, $X_1$ is an N-carbozoyl group, an N-phenoxazyl group or an N-phenothiazyl group which is unsubstituted or mono- or poly-substituted by a halogen atom, an alkyl group having 1 to 4 carbon atoms, an alkoxy group having 1 to 4 carbon atoms, or an aryl group having 6 to 10 carbon atoms. Still more preferably, $X_1$ is an unsubstituted N-carbazoyl group, an unsubstituted N-phenoxazyl group or an unsubstituted N-phenothiazyl group.

Specific examples of the substituted or unsubstituted N-carbazoyl group, the substituted or unsubstituted N-phenoxazyl group, and the substituted or unsubstituted N-phenothiazyl group represented by $X_1$ include N-carbazoyl, 2-methyl-N-carbazoyl, 3-methyl-N-carbazoyl, 4-methyl-N-carbozoyl, 3-n-butyl-N-carbazoyl, 3-n-hexyl-N-carbazoyl, 3-n-octyl-N-carbazoyl, 3-n-decyl-N-carbazoyl, 3,6-dimethyl-N-carbazoyl, 2-methoxy-N-carbazoyl, 3-methoxy-N-carbazoyl, 3-ethoxy-N-carbazoyl, 3-isopropoxy-N-carbazoyl, 3-n-butoxy-N-carbozoyl, 3-n-octyloxy-N-carbozoyl, 3-n-decyloxy-N-carbazoyl, 3-phenyl-N-carbazoyl, 3-(4'-methylphenyl)-N-carbazoyl, 3-chloro-N-carbazoyl, N-phenoxazyl, N-phenothiazyl, and 2-methyl-N-phenothiazyl. In the compound represented by the general formula (1), $X_2$ is a substituted or unsubstituted N-carbazoyl group, a substituted or unsubstituted N-phenoxazyl group, a substituted or unsubstituted N-phenothiazyl group or —$NAr^{21'}Ar^{22'}$ (wherein $Ar^{21'}$ and $Ar^{22'}$ are a substituted or unsubstituted aryl group).

As specific examples of the substituted or unsubstituted N-carbazoyl group, the substituted or unsubstituted N-phenoxazyl group, and the substituted or unsubstituted N-phenothiazyl group represented by $X_2$, the same N-carbazoyl groups, N-phenoxazyl groups and N-phenothiazyl groups as those exemplified as the specific examples for $X_4$ can be given.

In $NAr^{21'}Ar^{22'}$, $Ar^{21'}$ and $Ar^{22'}$ are a substituted or unsubstituted aryl group. Here, the aryl group means a carbocyclic aromatic group such as phenyl, naphthyl, and anthryl or a heterocyclic aromatic group such as furyl, thienyl and pyridyl. $Ar^{21'}$ and $Ar^{22'}$ are preferably a carbocyclic aromatic group having 6 to 20 total carbon atoms or a heterocyclic aromatic group having 3 to 20 total carbon atoms, which is unsubstituted or mono- or poly-substituted by a halogen atom, an alkyl group, an alkoxy group or an aryl group. More preferably, $Ar^{21'}$ and $Ar^{22'}$ are a carbocyclic aromatic group having 6 to 20 total carbon atoms, which is unsubstituted or mono- or poly-substituted by a halogen atom, an alkyl group having 1 to 14 carbon atoms, an alkoxy group having 1 to 14 carbon atoms or an aryl group having 6 to 10 carbon atoms. Still more preferably, $Ar^{21'}$ and $Ar^{22'}$ are a carbocyclic aromatic group having 6 to 16 total carbon atoms, which is unsubstituted or mono- or poly-substituted by a halogen atom, an alkyl group having 1 to 4 carbon atoms, an alkoxy group having 1 to 4 carbon atoms or an aryl group having 6 to 10 carbon atoms.

Specific examples of $Ar^{21'}$ and $Ar^{22'}$ include, but not limited thereto, phenyl, 1-naphthyl, 2-naphthyl, 2-anthryl, 9-anthryl, 4-quinolyl, 4-pyridyl, 3-pyridyl, 2-pyridyl, 3-furyl, 2-furyl, 3-thienyl, 2-thienyl, 2-oxazolyl, 2-thiazolyl, 2-benzoxazolyl, 2-benzothiazolyl, 2-benzoimidazolyl, 4-methylphenyl, 3-methylphenyl, 2-methylphenyl, 4-ethylphenyl, 3-ethylphenyl, 2-ethylphenyl, 4-n-propylphenyl, 4-isopropylphenyl, 2-isopropylphenyl, 4-n-butylphenyl, 4-isobutylphenyl, 4-sec-butylphenyl, 2-sec-butylphenyl, 4-tert-butylphenyl, 3-tert-butylphenyl, 2-tert-butylphenyl, 4-n-pentylphenyl, 4-isopentylphenyl, 2-neopentylphenyl, 4-tert-pentylphenyl, 4-n-hexylphenyl, 4-(2'-ethylbutyl)phenyl, 4-n-heptylphenyl, 4-n-octylphenyl, 4-(2'-ethylhexyl)phenyl, 4-tert-octylphenyl, 4-n-decylphenyl, 4-n-dodecylphenyl, 4-n-tetradecylphenyl, 4-cyclopentylphenyl, 4-cyclohexylphenyl, 4-(4'-methylcylohexyl)phenyl, 4-(4'-tert-butylcyclohexyl)phenyl, 3-cyclohexylphenyl, 2-cyclohexylphenyl, 4-ethyl-1-naphthyl, 6-n-butyl-2-naphthyl, 2,4-dimethylphenyl, 2,5-dimethylphenyl, 3,4-dimethylphenyl, 3,5-dimethylphenyl, 2,6-dimethylphenyl, 2,4-diethylphenyl, 2,3,5-trimethylphenyl, 2,3,6-trimethylphenyl, 3,4,5-trimethylphenyl, 2,6-diethylphenyl, 2,5-diisopropylphenyl, 2,6-diisobutylphenyl, 2,4-di-tert-butylphenyl, 2,5-di-tert-butylphenyl, 4,6-di-tert-butyl-2-methylphenyl, 5-tert-butyl-2-methylphenyl, 4-tert-butyl-2,6-dimethylphenyl, 4-methoxyphenyl, 3-methoxyphenyl, 2-methoxyphenyl, 4-ethoxyphenyl, 3-ethoxyphenyl, 2-ethoxyphenyl, 4-n-propoxyphenyl, 3-n-propoxyphenyl, 4-isopropoxyphenyl, 2-isopropoxyphenyl, 4-n-butoxyphenyl, 4-isobutoxyphenyl, 2-sec-butoxyphenyl, 4-n-pentyloxyphenyl, 4-isopentyloxyphenyl, 2-isopentyloxyphenyl, 4-neopentyloxyphenyl, 2-neopentyloxyphenyl, 4-n-hexyloxyphenyl, 2-(2'-ethylbutyl)oxyphenyl, 4-n-octyloxyphenyl, 4-n-decyloxyphenyl, 4-n-dodecyloxyphenyl, 4-n-tetradecyloxyphenyl, 4-cyclohexyloxyphenyl, 2-cyclohexyloxyphenyl, 2-methoxy-1-naphthyl, 4-methoxy-1-naphthyl, 4-n-butoxy-1-naphthyl, 5-ethoxy-1-naphthyl, 6-methoxy-2-naphthyl, 6-ethoxy-2-naphthyl, 6-n-buthoxy-2-naphthyl 6-n-hexyoxy-2-naphthyl, 7-methoxy-2-naphthyl, 7-n-buthoxy-2-naphthyl, 2-methyl-4-methoxyphenyl, 2-methyl-5-methoxyphenyl, 3-methyl-5-methoxyphenyl, 3-ethyl-5-methoxyphenyl, 2-methoxy-4-methylphenyl, 3-methoxy-4-methylphenyl, 2,4-dimethoxyphenyl, 2,5-dimethoxyphenyl, 2,6-dimethoxyphenyl, 3,4-dimethoxyphenyl, 3,5-dimethoxyphenyl, 3,5-diethoxyphenyl, 3,5-di-n-buthoxyphenyl, 2-methoxy-4-ethoxyphenyl, 2-methoxy-6-ethoxyphenyl, 3,4,5-trimethoxyphenyl, 4-phenylphenyl, 3-phenylphenyl, 2-phenylphenyl, 4-(4'-methylphenyl)phenyl, 4-(3'-methylphenyl)phenyl, 4-(4'-methoxyphenyl)phenyl, 4-(4'-n-buthoxyphenyl)phenyl, 2-(2'-methoxyphenyl) phenyl, 4-(4'-chlorophenyl)phenyl, 3-methyl-4-phenylphenyl, 3-methoxy-4-phenylphenyl, 4-fluorophenyl, 3-fluorophenyl, 2-fluorophenyl, 4-chlorophenyl, 3-chlorophenyl, 2-chlorophenyl, 4-bromophenyl, 2-bromophenyl, 4-chloro-1-naphthyl, 4-chloro-2-naphthyl, 6-bromo-2-naphthyl, 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 3,4-dichlorophenyl, 3,5-dichlorophenyl, 2,5-dibromophenyl, 2,4,6-trichlorophenyl, 2,4-dichloro-1-naphthyl, 1,6-dichloro-2-naphthyl, 2-fluoro-4-methylphenyl, 2-fluoro-5-methylphenyl, 3-fluoro-2-methylphenyl, 3-fluoro-4-methylphenyl, 2-methyl-4-fluorophenyl, 2-methyl-5-fluorophenyl, 3-methyl-4-fluorophenyl, 2-chloro-4-methylphenyl, 2-chloro-5-methylphenyl, 2-chloro-6-methylphenyl, 2-methyl-3-chlorophenyl, 2-methyl-4-chlorophenyl, 3-methyl-4-chlorophenyl, 2-chloro-4,6-dimethylphenyl, 2-methoxy-4-fluorophenyl, 2-fluoro-4-methoxyphenyl, 2-fluoro-4-ethoxyphenyl, 2-fluoro-6-methoxyphenyl, 3-fluoro-4-ethoxyphenyl, 3-chloro-4-methoxyphenyl, 2-methoxy-5-chlorophenyl, 3-methoxy-6-chlorophenyl, and 5-chloro-2,4-dimethoxyphenyl.

In the compound represented by the formula (9), $B_1$ and $B_2$ are a hydrogen atom, a linear, branched or cyclic alkyl group, a substituted or unsubstituted aryl group, or a substituted or unsubstituted aralkyl group. Preferably, $B_1$ and $B_2$ are a hydrogen atom, a linear, branched or cyclic alkyl group having 1 to 16 carbon atoms, a substituted or unsubstituted aryl group having 4 to 16 carbon atoms, or a substituted or unsubstituted aralkyl group having 5 to 16 carbon atoms. More preferably, $B_1$ and $B_2$ are a hydrogen atom, a linear, branched or cyclic alkyl group having 1 to 8 carbon atom, a substituted or unsubstituted aryl group having 6 to 12 carbon atoms or a substituted or unsubstituted aralkyl group having 7 to 12 carbon atoms. Still more preferably, $B_1$ and $B_2$ are a linear, branched or cyclic alkyl group having 1 to 8 carbon atoms, a carbocyclic aromatic group having 6 to 10 carbon atoms, and a carbocyclic aralkyl group having 7 to 10 carbon atoms.

As the specific examples of the substituted or unsubstituted aryl group represented by $B_1$ and $B_2$, the same substituted or unsubstituted aryl group exemplified as the specific examples for $Ar_4$ and $Ar_2$ can be given, for example. Specific examples of the liner, branched or cyclic alkyl group represented by $B_1$ and $B_2$ include, but not limited thereto, methyl, ethyl, n-propyl, isopropyl, n-butyl, isobutyl, sec-butyl, tert-butyl, n-pentyl, iso-pentyl, neo-pentyl, tert-pentyl, cyclopentyl, n-hexyl, 2-ethylbutyl, 3,3-dimethylbutyl, cyclohexyl, n-heptyl, cyclohexylmethyl, n-octyl, tert-octyl, 2-ethylhexyl, n-nonyl, n-decyl, n-dodecyl, n-tetradecyl and n-hexadecyl.

Specific examples of the substituted or unsubstituted aralkyl group represented by $B_1$ and $B_2$ include, but not limited thereto, an aralkyl group such as benzyl, phenethyl, α-methylbenzyl, α,α-dimethylbenzyl, 1-naphthylmethyl, 2-naphthylmethyl, furfuryl, 2-methylbenzyl, 3-methylbenzyl, 4-methylbenzyl, 4-ethylbenzyl, 4-isopropylbenzyl, 4-tert-butylbenzyl, 4-n-hexylbenzyl, 4-nonylbenzyl, 3,4-dimethylbenzyl, 3-methoxybenzyl, 4-methoxybenzyl, 4-ethoxybenzyl, 4-n-butoxybenzyl, 4-n-hexyloxybenzyl, 4-nonyloxybenzyl, 4-fluorobenzyl, 3-fluorobenzyl, 2-chlorobenzyl, and 4-chlorobenzyl.

$Z_1$ and $Z_2$ are a hydrogen atom, a halogen atom, a linear, branched or cyclic alkyl group, a linear, branched or cyclic alkoxy group, or a substituted or unsubstituted aryl group. Preferably, $Z_1$ and $Z_2$ are a hydrogen atom, a halogen atom, a linear, branched or cyclic alkyl group having 1 to 16 carbon atoms, a linear, branched or cyclic alkoxy group having 1 to 16 carbon atoms, or a substituted or unsubstituted aryl group having 4 to 20 carbon atoms. More preferably, $Z_1$ and $Z_2$ are a hydrogen atom, a halogen atom, a linear, branched or cyclic alkyl group having 1 to 8 carbon atoms, a linear, branched or cyclic alkoxy group having 1 to 8 carbon atoms, or a substituted or unsubstituted aryl group having 6 to 12 carbon atoms. Still more preferably, $Z_1$ and $Z_2$ are a hydrogen atom.

As the specific examples of the linear, branched or cyclic alkyl group represented by $Z_1$ and $Z_2$, the same linear, branched or cyclic alkyl group exemplified as the specific examples for $B_1$ and $B_2$ can be given. As the specific examples of the substituted or unsubstituted aryl group represented by $Z_1$ and $Z_2$, the same substituted or unsubstituted aryl group exemplified as the specific examples for $Ar^{21'}$ and $Ar^{22'}$ can be given, for example.

Specific examples of the halogen atom, the linear, branched or cyclic alkoxy group represented by $Z_1$ and $Z_2$ include a halogen atom such as fluorine, chlorine, and bromine, and an alkoxy group such as methoxy, ethoxy, n-propoxy, isopropoxy, n-butoxy, isobutoxy, sec-butoxy, n-pentyloxy, isopentyloxy, neopentyloxy, cyclopentyloxy, n-hexyloxy, 2-ethylbutoxy, 3,3-dimethylbutoxy, cyclohexyloxy, n-heptyloxy, cyclohexylmethyloxy, n-octyloxy, 2-ethylhexyloxy, n-nonyloxy, n-decyloxy, n-dodecyloxy, n-tetradecyloxy, and n-hexadecyloxy.

Specific examples of the compound represented by the above formula (9) include, but not limited thereto, the following compounds (No. 1-100).

Example Compounds 1. 7-(N'-carbazoyl)-N,N-diphenyl-9H-fluorene-2-amine
2. 7-(N'-carbazoyl)-N-phenyl-N-(4'-methylphenyl)-9-methyl-9H-fluorene-2-amine
3. 7-(N'-carbazoyl)-N,N-diphenyl-9,9-dimethyl-9H-fluorene-2-amine
4. 7-(N'-carbazoyl)-N-phenyl-N-(3'-methylphenyl)-9,9-dimethyl-9H-fluorene-2-amine
5. 7-(N'-carbazoyl)-N-phenyl-N-(4'-methylphenyl)-9,9-dimethyl-9H-fluorene-2-amine
6. 7-(N'-carbazoyl)-N-phenyl-N-(4'-ethylphenyl)-9,9-dimethyl-9H-fluorene-2-amine
7. 7-(N'-carbazoyl)-N-phenyl-N-(4'-tert-butylphenyl)-9,9-dimethyl-9H-fluorene-2-amine
8. 7-(N'-carbazoyl)-N-phenyl-N-(3',4'-dimethylphenyl)-9,9-dimethyl-9H-fluorene-2-amine
9. 7-(N'-carbazoyl)-N-phenyl-N-(3',5'-dimethylphenyl)-9,9-dimethyl-9H-fluorene-2-amine
10. 7-(N'-carbazoyl)-N,N-di(3'-methylphenyl)-9,9-dimethyl-9H-fluorene-2-amine
11. 7-(N'-carbazoyl)-N,N-di(4'-methylphenyl)-9,9-dimethyl-9H-fluorene-2-amine
12. 7-(N'-carbazoyl)-N,N-di(4'-ethylphenyl)-9,9-dimethyl-9H-fluorene-2-amine
13. 7-(N'-carbazoyl)-N-phenyl-N-(3'-methoxyphenyl)-9,9-dimethyl-9H-fluorene-2-amine
14. 7-(N'-carbazoyl)-N-phenyl-N-(4'-methoxyphenyl)-9,9-dimethyl-9H-fluorene-2-amine
15. 7-(N'-carbazoyl)-N-phenyl-N-(4'-ethoxyphenyl)-9,9-dimethyl-9H-fluorene-2-amine
16. 7-(N'-carbazoyl)-N-phenyl-N-(4'-n-butoxyphenyl)-9,9-dimethyl-9H-fluorene-2-amine
17. 7-(N'-carbazoyl)-N,N-di(4'-methoxyphenyl)-9,9-dimethyl-9H-fluorene-2-amine
18. 7-(N'-carbazoyl)-N-(3'-methylphenyl)-N-(4"-methoxyphenyl)-9,9-dimethyl-9H-fluorene-2-amine
19. 7-(N'-carbazoyl)-N-(4'-methylphenyl)-N-(4"-methoxyphenyl)-9,9-dimethyl-9H-fluorene-2-amine
20. 7-(N'-carbazoyl)-N-phenyl-N-(3'-fluorophenyl)-9,9-dimethyl-9H-fluorene-2-amine
21. 7-(N'-carbazoyl)-N-phenyl-N-(4'-chlorophenyl)-9,9-dimethyl-9H-fluorene-2-amine
22. 7-(N'-carbazoyl)-N-phenyl-N-(4'-phenylphenyl)-9,9-dimethyl-9H-fluorene-2-amine
23. 7-(N'-carbazoyl)-N-phenyl-N-(1'-naphthyl)-9,9-dimethyl-9H-fluorene-2-amine
24. 7-(N'-carbazoyl)-N-phenyl-N-(2'-naphthyl)-9,9-dimethyl-9H-fluorene-2-amine
25. 7-(N'-carbazoyl)-N-(4'-methylphenyl)-N-(2"-naphthyl)-9,9-dimethyl-9H-fluorene-2-amine
26. 7-(N'-carbazoyl)-N-phenyl-N-(2'-furyl)-9,9-dimethyl-9H-fluorene-2-amine
27. 7-(N'-carbozyl)-N-phenyl-N-(2'-thienyl)-9,9-dimethyl-9H-fluorene-2-amine
28. 7-(N'-carbazoyl)-N,N-diphenyl-4-fluoro-9,9-dimethyl-9H-fluorene-2-amine
29. 7-(N'-carbazoyl)-N,N-diphenyl-3-methoxy-9,9-dimethyl-9H-fluorene-2-amine
30. 7-(N'-carbazoyl)-N,N-diphenyl-4-phenyl-9,9-dimethyl-9H-fluorene-2-amine
31. 7-(3'-methyl-N'-carbazoyl)-N,N-diphenyl-9,9-dimethyl-9H-fluorene-2-amine
32. 7-(3'-methoxy-N'-carbazoyl)-N,N-diphenyl-9,9-dimethyl-9H-fluorene-2-amine
33. 7-(3'-chloro-N'-carbazoyl)-N,N-diphenyl-9,9-dimethyl-9H-fluorene-2-amine
34. 2,7-di(N-carbazoyl)-9,9-dimethyl-9H-fluorene
35. 7-(N'-phenoxazyl)-N,N-diphenyl-9,9-dimethyl-9H-fluorene-2-amine
36. 7-(N'-phenoxazyl)-N,N-di(4'-methylphenyl)-9,9-dimethyl-9H-fluorene-2-amine
37. 2,7-di(N-phenoxazyl)-9,9-dimethyl-9H-fluorene
38. 7-(N'-phenothiazyl)-N,N-diphenyl-9,9-dimethyl-9H-fluorene-2-amine
39. 7-(N'-phenothiazyl)-N-phenyl-N-(3'-methylphenyl)-9,9-dimethyl-9H-fluorene-2-amine
40. 7-(N'-phenothiazyl)-N-phenyl-N-(4'-methylphenyl)-9,9-dimethyl-9H-fluorene-2-amine
41. 7-(N'-phenothiazyl)-N,N-di(4'-methylphenyl)-9,9-dimethyl-9H-fluorene-2-amine
42. 7-(N'-phenothiazyl)-N-phenyl-N-(4'-methoxyphenyl)-9,9-dimethyl-9H-fluorene-2-amine
43. 7-(N'-phenothiazyl)-N-phenyl-N-(2'-naphthyl)-9,9-dimethyl-9H-fluorene-2-amine
44. 2,7-di(N-phenothiazyl)-9,9-dimethyl-9H-fluorene
45. 7-(N'-carbazoyl)-N,N-diphenyl-9,9-diethyl-9H-fluorene-2-amine
46. 7-(N'-carbazoyl)-N-phenyl-N-(4'-methylphenyl)-9,9-diethyl-9H-fluorene-2-amine
47. 7-(N'-carbazoyl)-N,N-di(4'-methylphenyl)-9,9-diethyl-9H-fluorene-2-amine
48. 7-(N'-carbozoyl)-N-phenyl-N-(3'-methoxyphenyl)-9,9-diethyl-9H-fluorene-2-amine
49. 7-(N'-carbazoyl)-N,N-diphenyl-4-methyl-9,9-diethyl-9H-fluorene-2-amine
50. 7-(N'-carbazoyl)-N,N-diphenyl-9-isopropyl-9H-fluorene-2-amine
51. 7-(N'-carbazoyl)-N,N-diphenyl-9,9-di-n-propyl-9H-fluorene-2-amine
52. 7-(N'-carbazoyl)-N-phenyl-N-(4'-methylphenyl)-9,9-di-n-propyl-9H-fluorene-2-amine
53. 7-(N'-carbazoyl)-N-phenyl-N-(4'-methoxyphenyl)-9,9-di-n-propyl-9H-fluorene-2-amine 54. 2,7-di(N-carbazoyl)-9,9-di-n-propyl-9H-fluorene
55. 2,7-di(N-phenoxazyl)-9,9-di-n-propyl-9H-fluorene
56. 7-(N'-carbazoyl)-N,N-diphenyl-9,9-di-n-butyl-9H-fluorene-2-amine
57. 7-(N'-carbazoyl)-N,N-di(4'-methylphenyl)-9,9-di-n-butyl-9H-fluorene-2-amine
58. 2,7-di(N-carbazoyl)-9,9-di-n-butyl-9H-fluorene
59. 7-(N'-carbazoyl)-N-phenyl-N-(4'-methoxyphenyl)-9,9-di-n-pentyl-9H-fluorene-2-amine
60. 7-(N'-phenoxazyl)-N-phenyl-N-(3'-methoxyphenyl)-9,9-di-n-pentyl-9H-fluorene-2-amine
61. 7-(N'-carbazoyl)-N,N-di(4"-methoxyphenyl)-9,9-di-n-pentyl-9H-fluorene-2-amine
62. 2,7-di(N'-carbazoyl)-9,9-di-n-pentyl-9H-fluorene
63. 7-(N'-carbazoyl)-N,N-diphenyl-9,9-di-n-hexyl-9H-fluorene-2-amine
64. 7-(N'-carbazoyl)-N,N-di(4'-methylphenyl)-9,9-di-n-hexyl-9H-fluorene-2-amine
65. 7-(N'-carbazoyl)-N,N-diphenyl-9-cyclohexyl-9H-fluorene-2-amine
66. 7-(N'-carbazoyl)-N,N-diphenyl-9,9-di-n-octyl-9H-fluorene-2-amine
67. 7-(N'-phenoxazyl)-N,N-di(4'-methylphenyl)-9,9-di-n-octyl-9H-fluorene-2-amine
68. 7-(N'-carbazoyl)-N,N-diphenyl-9-methyl-9-ethyl-9H-fluorene-2-amine
69. 7-(N'-carbazoyl)-N,N-diphenyl-9-methyl-9-n-propyl-9H-fluorene-2-amine
70. 7-(N'-phenothiazyl)-N,N-diphenyl-9-methyl-9-n-propyl-9H-fluorene-2-amine
71. 7-(N'-carbazoyl)-N,N-diphenyl-9-ethyl-9-n-hexyl-9H-fluorene-2-amine
72. 7-(N'-carbazoyl)-N,N-diphenyl-9-ethyl-9-cyclohexyl-9H-fluorene-2-amine
73. 7-(N'-carbazoyl)-N,N-diphenyl-9-benzyl-9H-fluorene-2-amine
74. 7-(N'-carbazoyl)-N,N-diphenyl-9,9-dibenzyl-9H-fluorene-2-amine
75. 7-(N'-carbazoyl)-N,N-diphenyl-9,9-di(4'-methylbenzyl)-9H-fluorene-2-amine
76. 7-(N'-carbazoyl)-N,N-diphenyl-9,9-di(4'-methoxybenzyl)-9H-fluorene-2-amine
77. 7-(N'-carbazoyl)-N-phenyl-N-(4'-methylphenyl)-9,9-dibenzyl-9H-fluorene-2-amine
78. 7-(N'-carbazoyl)-N,N-di(4'-methylphenyl)-9,9-dibenzyl-9H-fluorene-2-amine
79. 7-(N'-carbazoyl)-N-phenyl-N-(4'-methoxyphenyl)-9,9-dibenzyl-9H-fluorene-2-amine
80. 7-(N'-carbazoyl)-N-phenyl-N-(4'-phenylphenyl)-9,9-dibenzyl-9H-fluorene-2-amine
81. 7-(N'-carbazoyl)-N-phenyl-N-(2'-naphthyl)-9,9-dibenzyl-9H-fluorene-2-amine
82. 7-(N'-phenoxazyl)-N-phenyl-N-(4'-methylphenyl)-9,9-dibenzyl-9H-fluorene-2-amine
83. 7-(N'-phenothiazyl)-N,N-di(4'-methylphenyl)-9,9-dibenzyl-9H-fluorene-2-amine
84. 2,7-di(N-carbazoyl)-9,9-dibenzyl-9H-fluorene
85. 2,7-di(N-carbazoyl)-9,9-di(4'-methylbenzyl)-9H-fluorene
86. 2-(N-carbazoyl)-7-(N'-phenothiazyl)-9,9-dibenzyl-9H-fluorene
87. 7-(N'-carbazoyl)-N,N-diphenyl-9-methyl-9-benzyl-9H-fluorene-2-amine
88. 7-(N'-phenoxazyl)-N,N-diphenyl-9-ethyl-9-benzyl-9H-fluorene-2-amine
89. 7-(N'-carbazoyl)-N,N-diphenyl-9,9-diphenyl-9H-fluorene-2-amine
90. 7-(N'-carbazoyl)-N-phenyl-N-(4'-methylphenyl)-9,9-diphenyl-9H-fluorene-2-amine
91. 7-(N'-carbazoyl)-N,N-di(4'-methylphenyl)-9,9-diphenyl-9H-fluorene-2-amine
92. 7-(N'-carbazoyl)-N-phenyl-N-(3'-methylphenyl)-9,9-di(4"-methylphenyl)-9H-fluorene-2-amine
93. 7-(N'-carbazoyl)-N-phenyl-N-(3'-methylphenyl)-9,9-di(4"-methoxyphenyl)-9H-fluorene-2-amine
94. 7-(N'-phenoxazyl)-N,N-di(4'-methylphenyl)-9,9-diphenyl-9H-fluorene-2-amine
95. 7-(N'-phenothiazyl)-N,N-diphenyl-9,9-diphenyl-9H-fluorene-2-amine
96. 2,7-di(N'-carbazoyl)-9,9-di(4'-methylphenyl)-9H-fluorene
97. 2-(N-carbazolyl)-7-(N'-phenoxazyl)-9,9-diphenyl-9H-fluorene
98. 2-(N-phenoxazyl)-7-(N'-phenothiazyl)-9,9-diphenyl-9H-fluorene
99. 7-(N'-carbazoyl)-N-phenyl-N-(4'-methylphenyl)-9-methyl-9-phenyl-9H-fluorene-2-amine
100. 7-(N'-carbazoyl)-N,N-diphenyl-9-ethyl-9-phenyl-9H-fluorene-2-amine Specific examples of the nitrogen-containing heterocyclic derivative which can be used in the invention are given below.

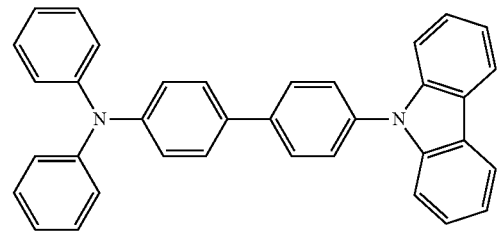

A-1

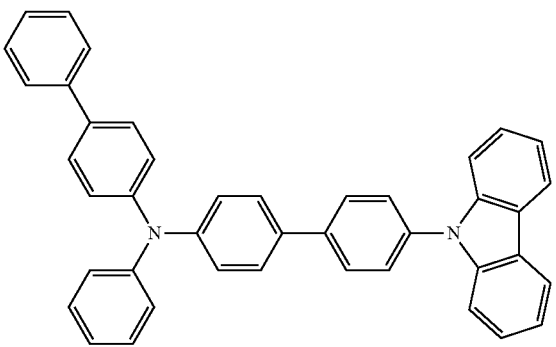

A-2

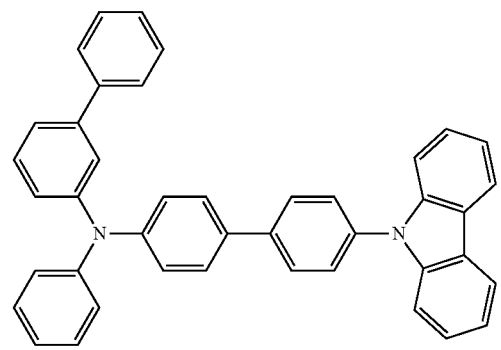

A-3

A-4
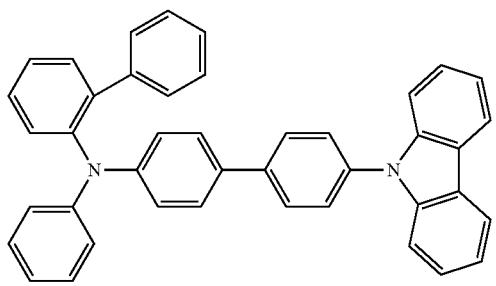
A-5
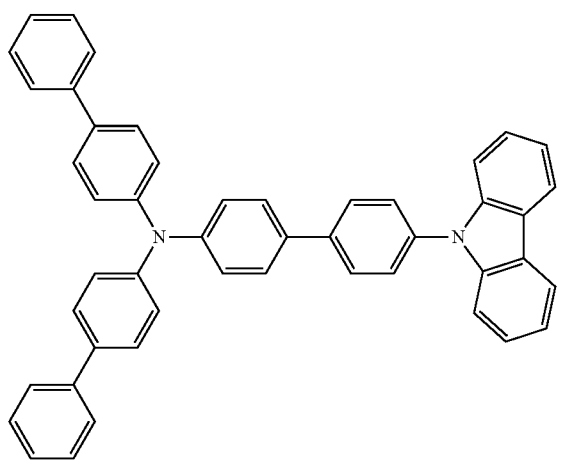
A-6
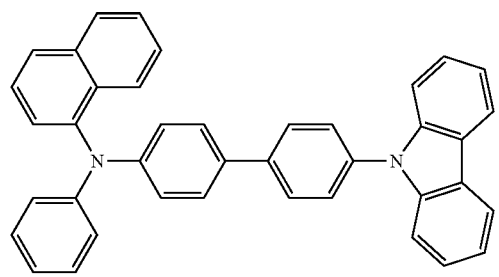
A-7
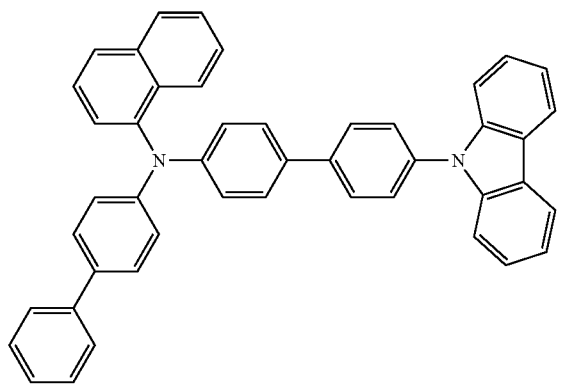
A-8
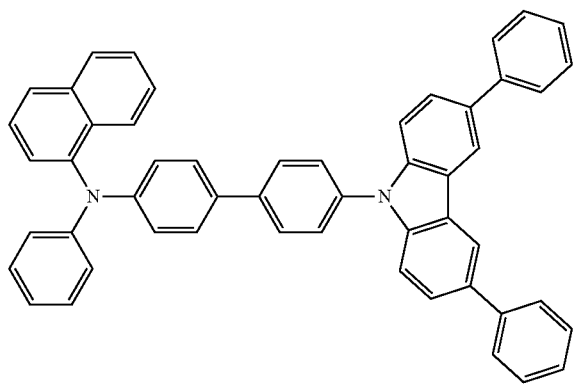
A-9
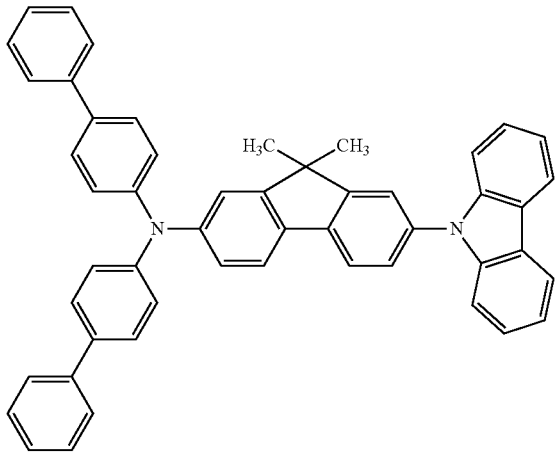
A-10
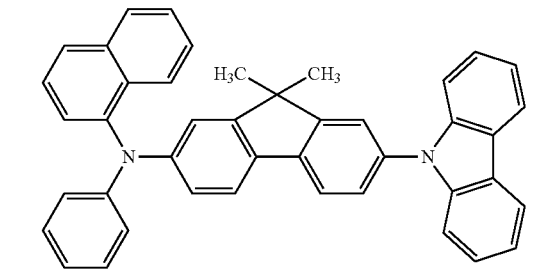
A-11
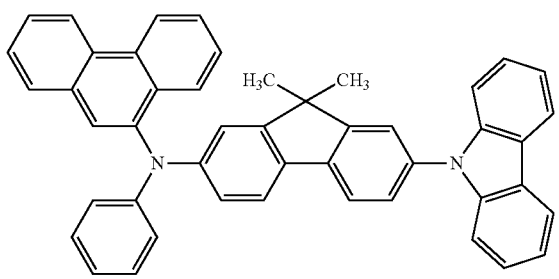

A-12
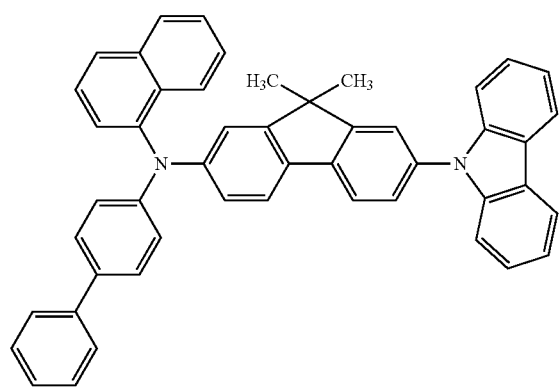
A-13
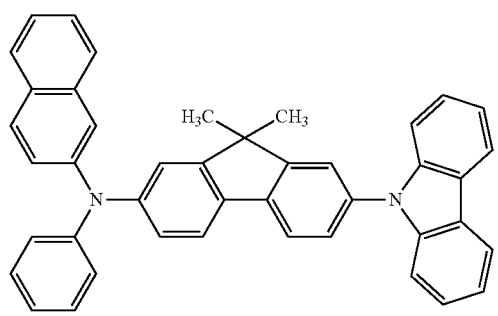
A-14
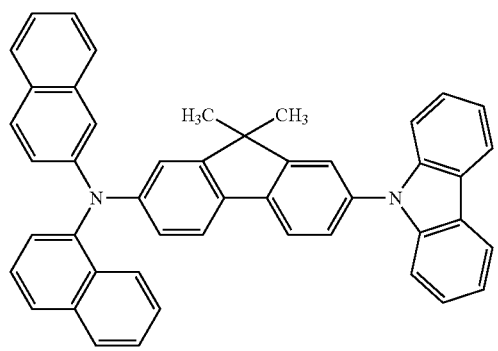
A-15
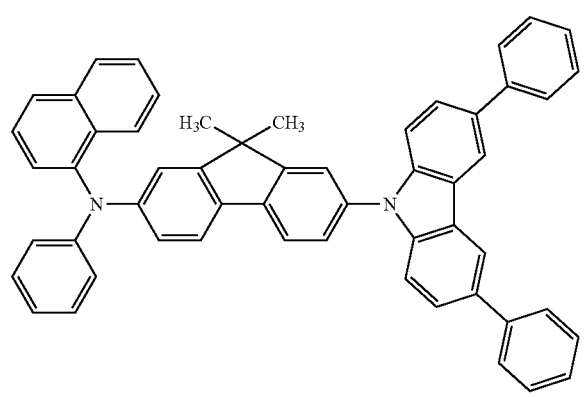
A-16
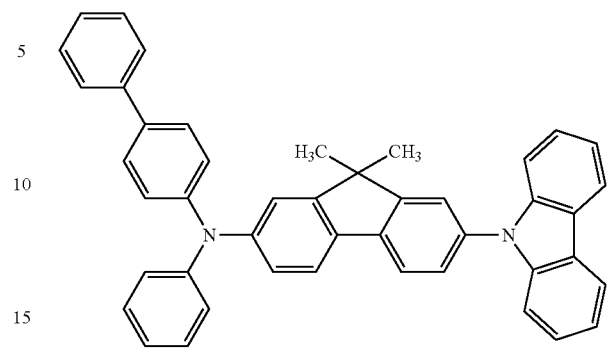
A-17
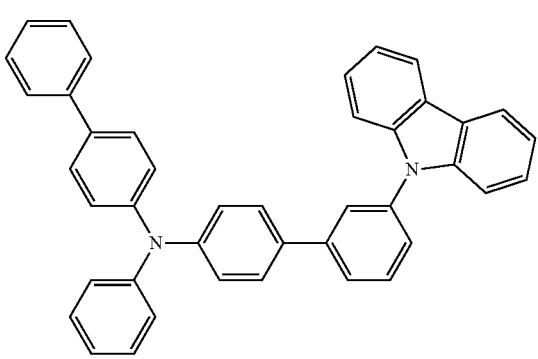
A-18
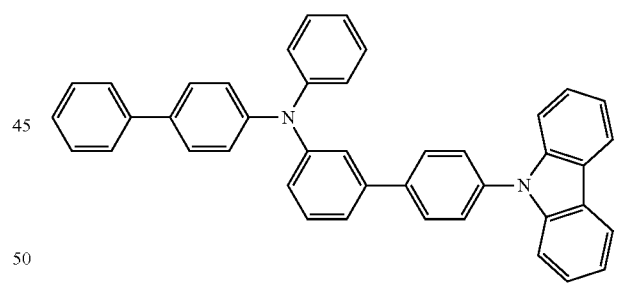
A-19
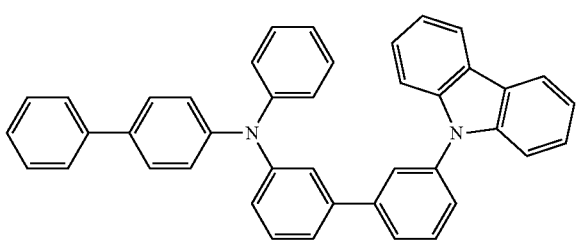

A-20
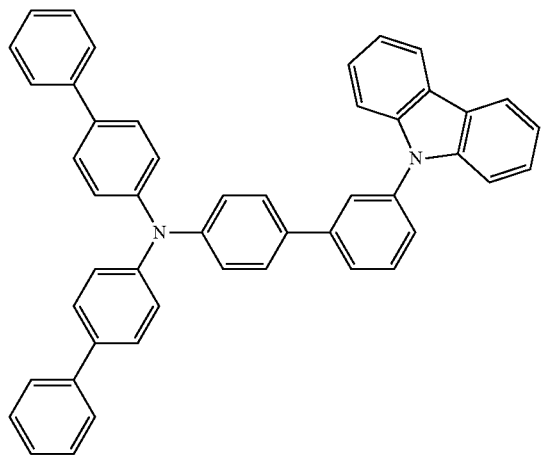
A-21
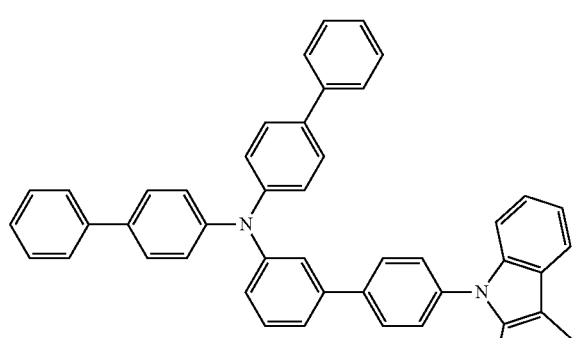
A-22
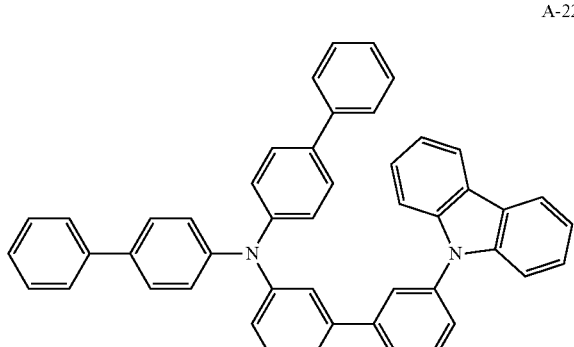
A-23
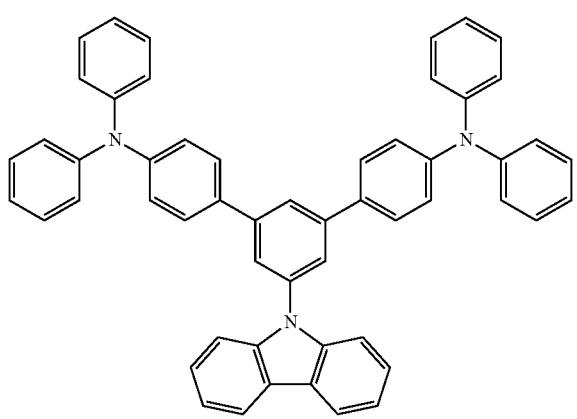
A-24
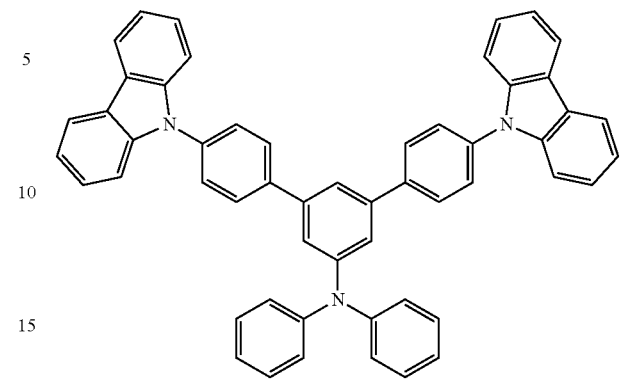
A-25
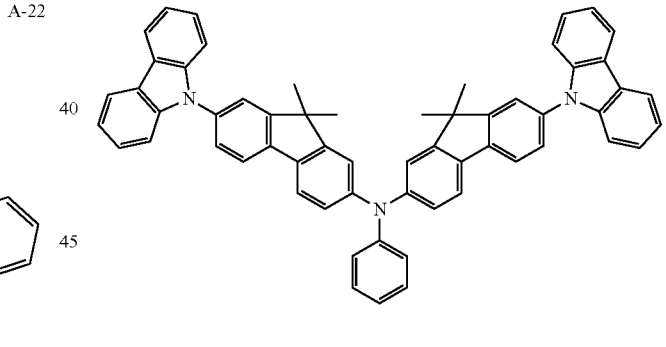
A-26
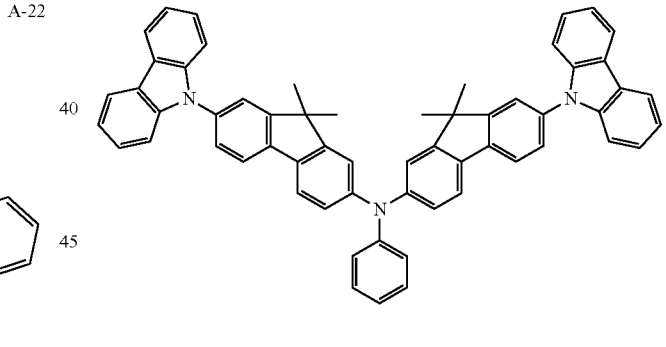
A-27

A-28
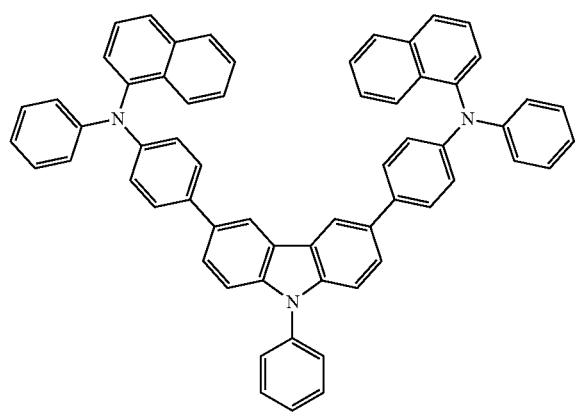
A-32
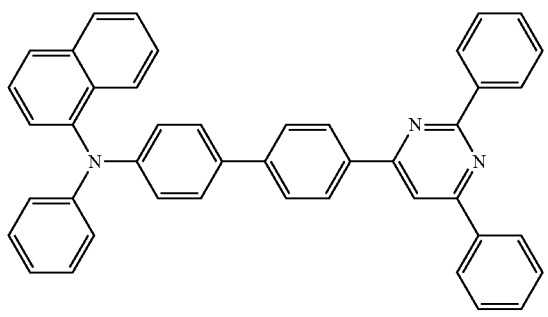
A-29
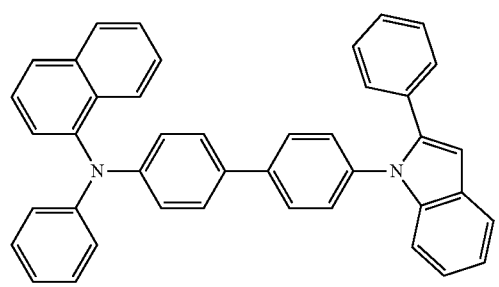
A-33
A-30
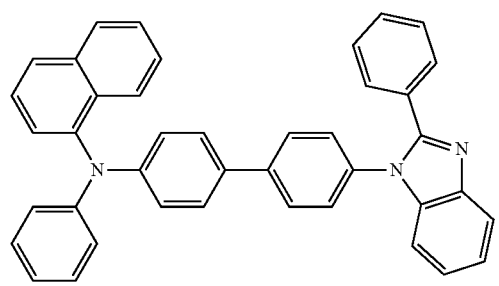
A-34
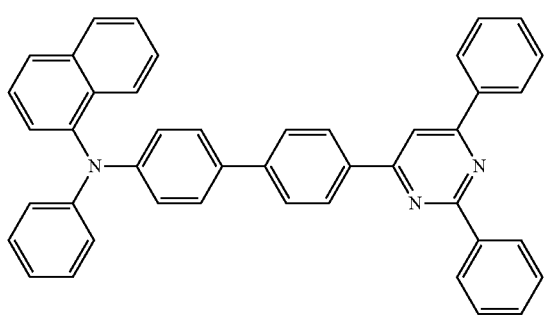
A-31
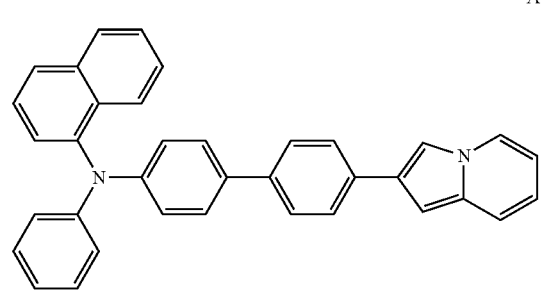
A-35
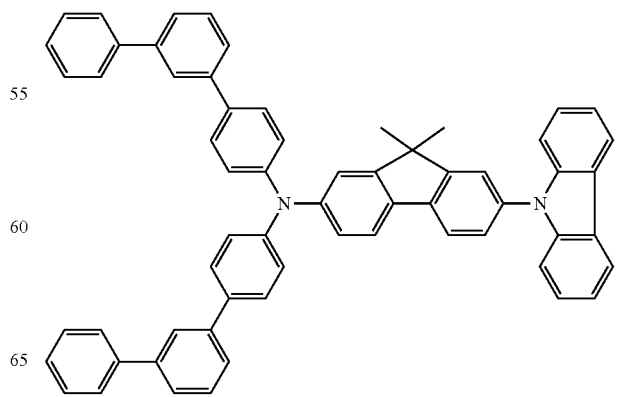

-continued
A-36
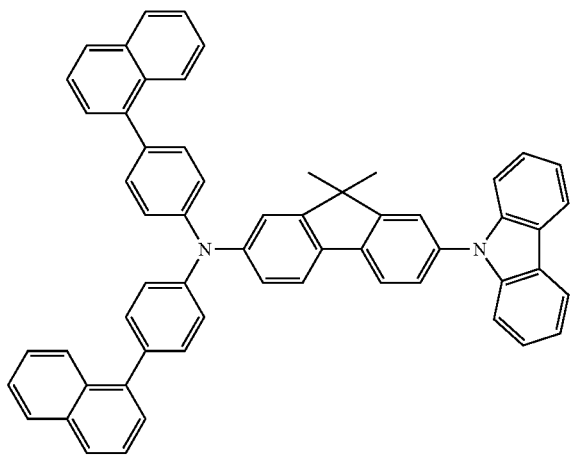
A-37
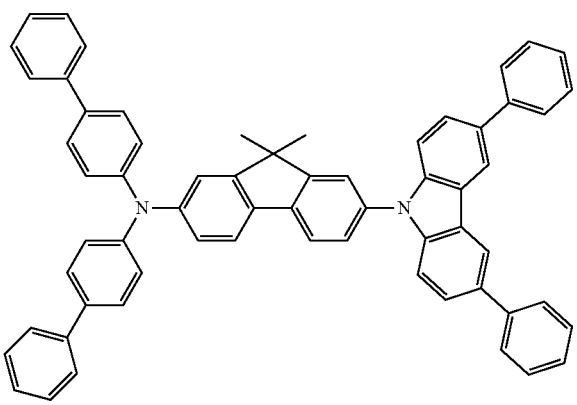
A-38
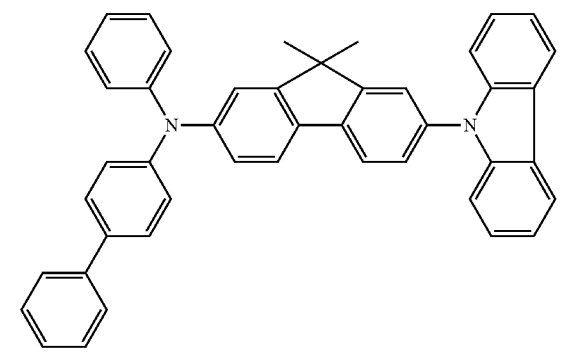
A-39
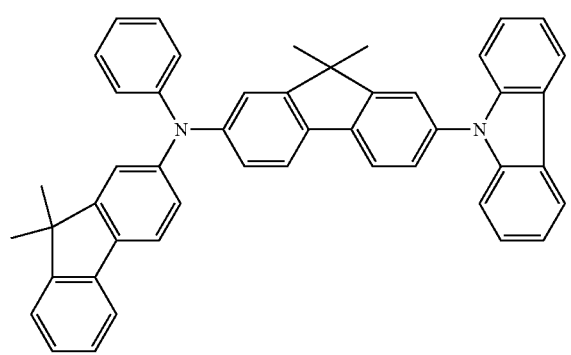
-continued
A-40
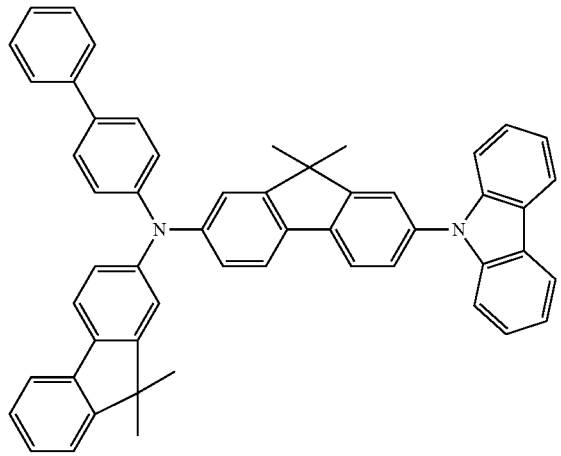
A-41
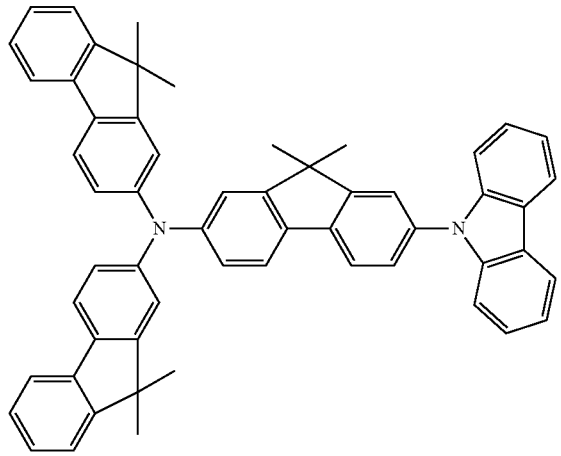
A-42
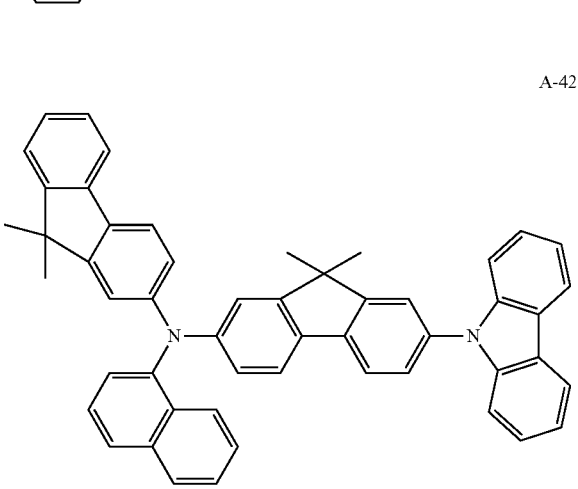
A-43
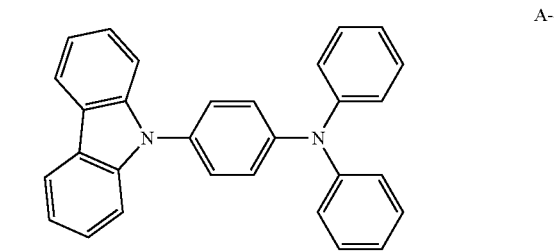

A-44
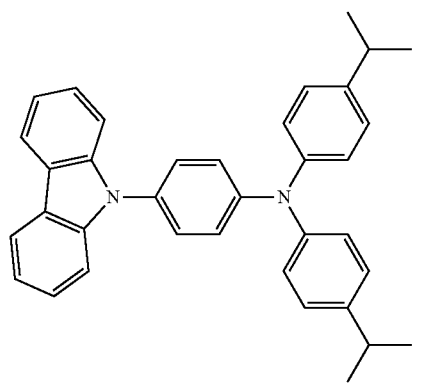
A-45
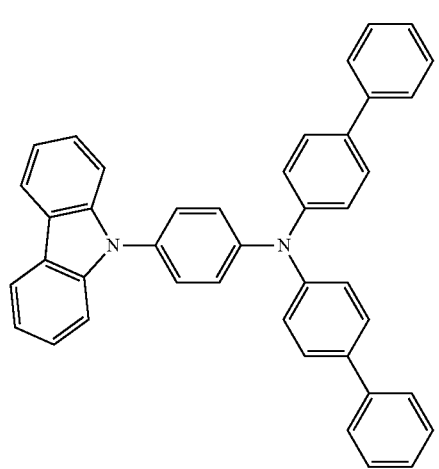
A-46
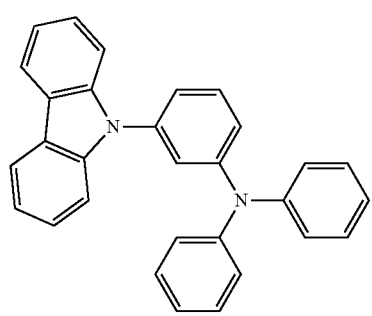
A-47
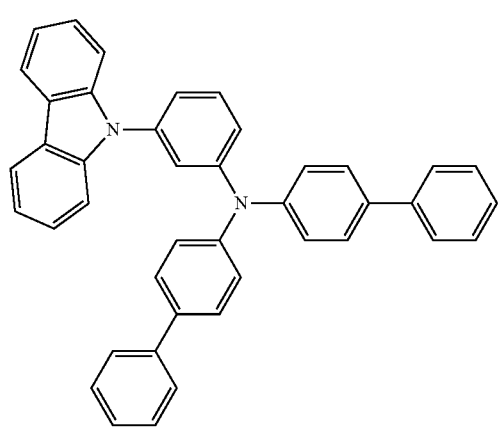
A-48
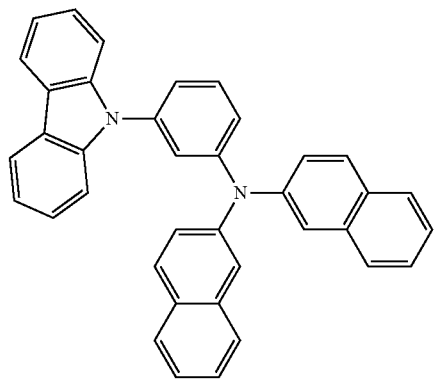
A-49
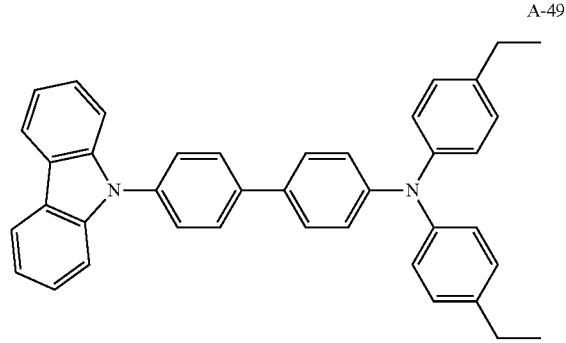
A-50
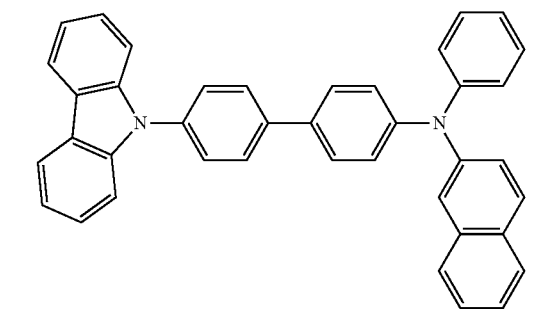
A-51
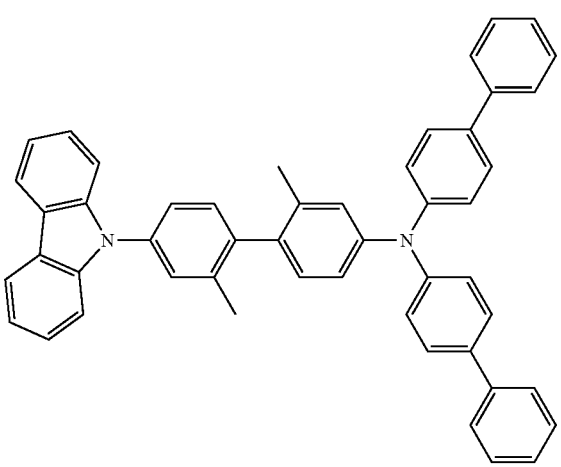

A-52
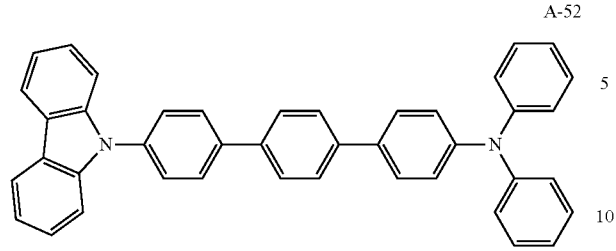
A-53
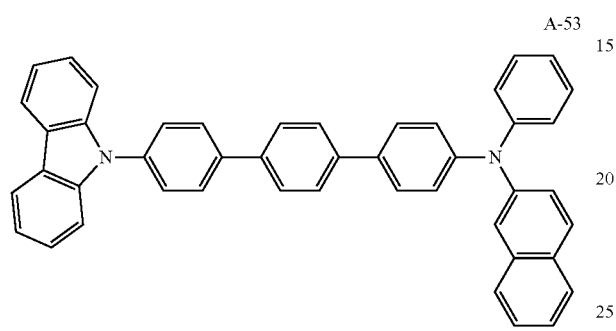
A-54
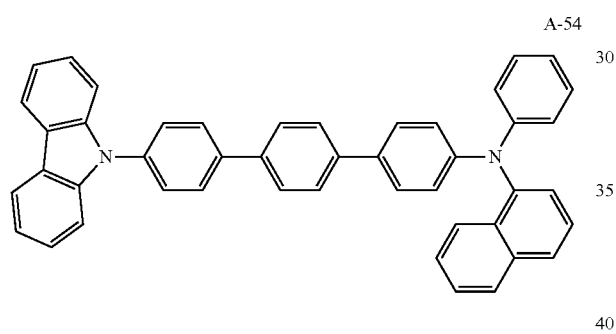
A-55
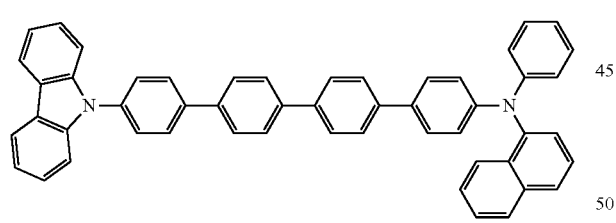
A-56
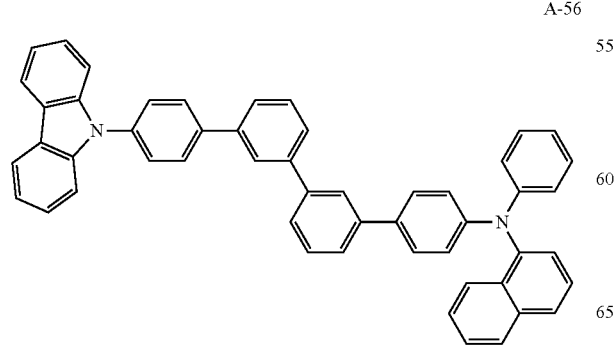
A-57
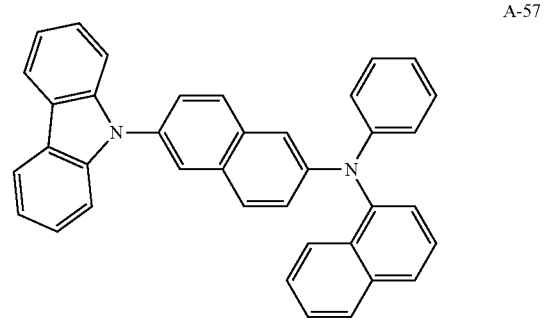
A-58
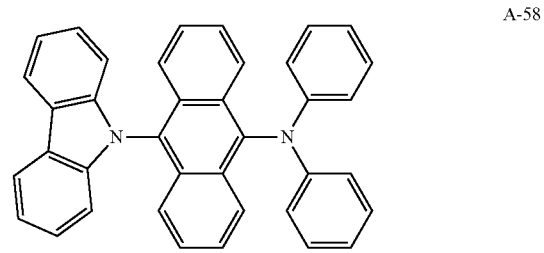
A-59
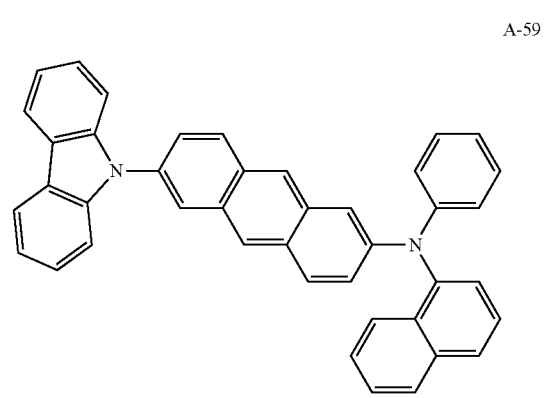
A-60
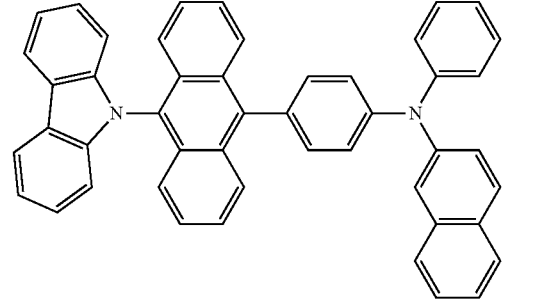
A-61
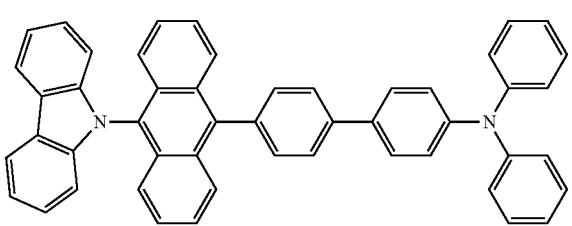

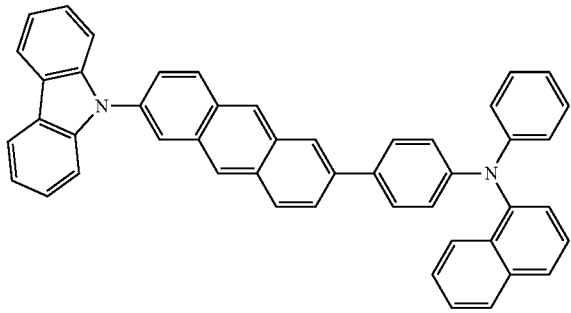

A-62

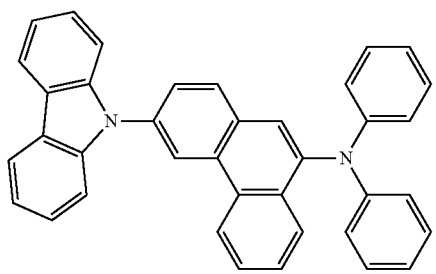

A-63

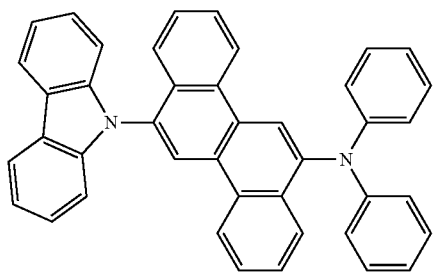

A-64

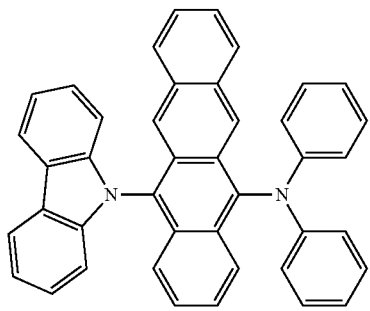

A-65

In the formula (2), $L_2$ is a substituted or unsubstituted arylene group having 10 to 40 carbon atoms.

Preferred examples include biphenylene, terphenylene, quarterphenylene, naphthylene, anthracenylene, phenanthrene, chrysenylene, pyrenylene, fluorenylene, 2,6-diphenylnaphthalene-4',4"-ene, 2-phenylnaphthalene-2,4'-ene, 1-phenylnaphthalene-1,4'-ene, 2,7-diphenylfluorenylene-4', 4"-ene, fluorenylene, 9,10-diphenylanthracene-4',4"-ene, and 6,12-diphenylchrysenylene-4',4"-ene.

Biphenylene, terphenylene, fluorenylene, 2-phenylnaphthalene-2,4'-ene, 1-phenylnaphthalene-1,4'-ene, and 6,12-diphenylchrysenylene-4',4"-ene are more preferable.

In the formula (2), $Ar_3$ to $Ar_6$ are independently a substituted or unsubstituted aromatic hydrocarbon ring group having 6 to 60 nucleus carbon atoms, or a substituted or unsubstituted aromatic heterocyclic group having 6 to 60 nucleus atoms.

Examples of the substituted or unsubstituted aromatic hydrocarbon ring group having 6 to 60 nucleus carbon atoms represented by $Ar_3$ to $Ar_6$ in the formula (2) are the same as those exemplified for $Ar_1$ and $Ar_2$ in the formula (1).

As the substituted or unsubstituted aromatic heterocyclic group having 6 to 60 necleus atoms, a 5- or 6-membered monocyclic or condensed ring containing two to five rings can be given. Specific examples include pyridyl, triazinyl, pyradinyl, quinoxalinyl and thienyl.

The amine derivative represented by the formula (2) is preferably a compound represented by the following formula (3).

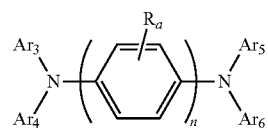

(3)

In the formula (3), $Ar_3$ to $Ar_6$ in the formula (3) are the same as $Ar_3$ to $Ar_6$ in the formula (2).

In the formula (3), $R_a$ represents a substituent. Specific examples of $R_a$ are the same as those exemplified above as the substituent for Z or the like in the formula (1).

n is an integer of 2 to 4, preferably 2 and 3.

The amine derivative represented by the formula (2) is more preferably a compound represented by the following formula (4) or (5).

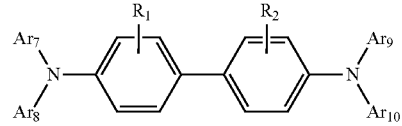

(4)

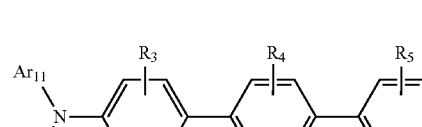

(5)

In the formula, $R_1$ to $R_5$ are a substituent. Examples thereof are the same as those exemplified as those for $R_a$ in the formula (3). $R_1$ and $R_2$, and $R_3$ to $R_5$ may be bonded to each other to form a saturated or unsaturated ring.

In the formula, $Ar_7$ to $Ar_{14}$ are independently a substituted or unsubstituted aromatic hydrocarbon ring group having 6 to 60 carbon atoms or a substituted or unsubstituted aromatic heterocyclic group having 6 to 60 nucleus atoms. Specific examples of $Ar_7$ to $Ar_{14}$ are the same as those exemplified above for $Ar_1$ and $Ar_2$ in the formula (1).

As specific examples of the substituent for $Ar_7$ to $Ar_{14}$ and $R_1$ to $R_5$, the same substituent as those exemplified as the substituent for Z or the like in the formula (1) can be given. As the structure of the substituted or unsubstituted ring formed by bonding of $R_1$ and $R_2$, the following can be given. The same can be applied when the ring is formed by bonding of $R_3$ to $R_5$.

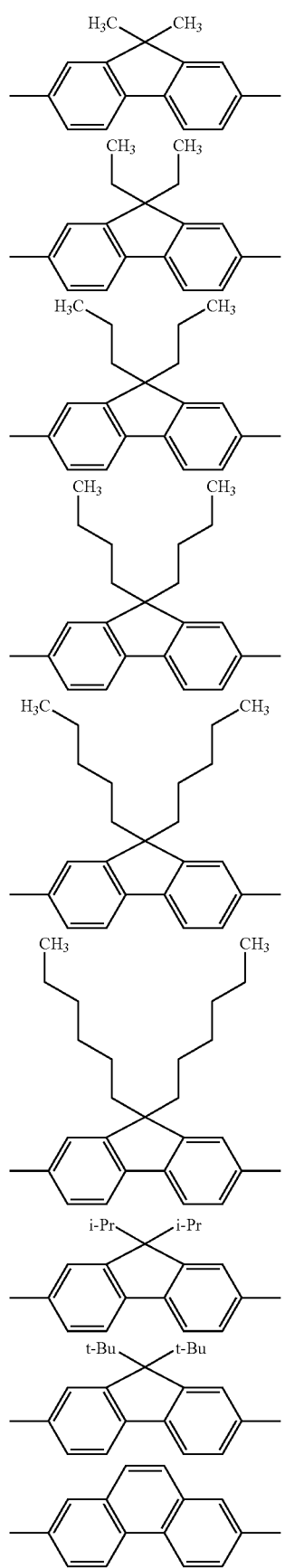
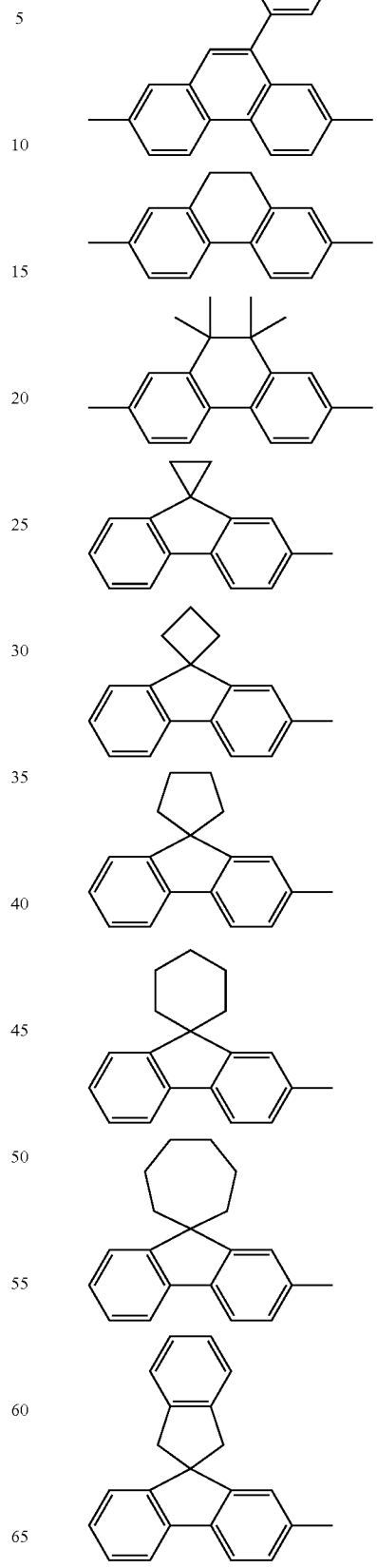

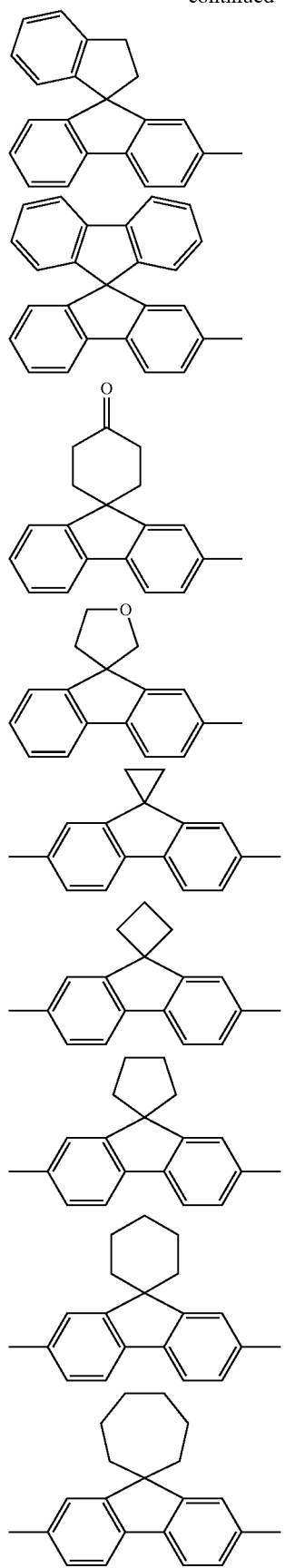
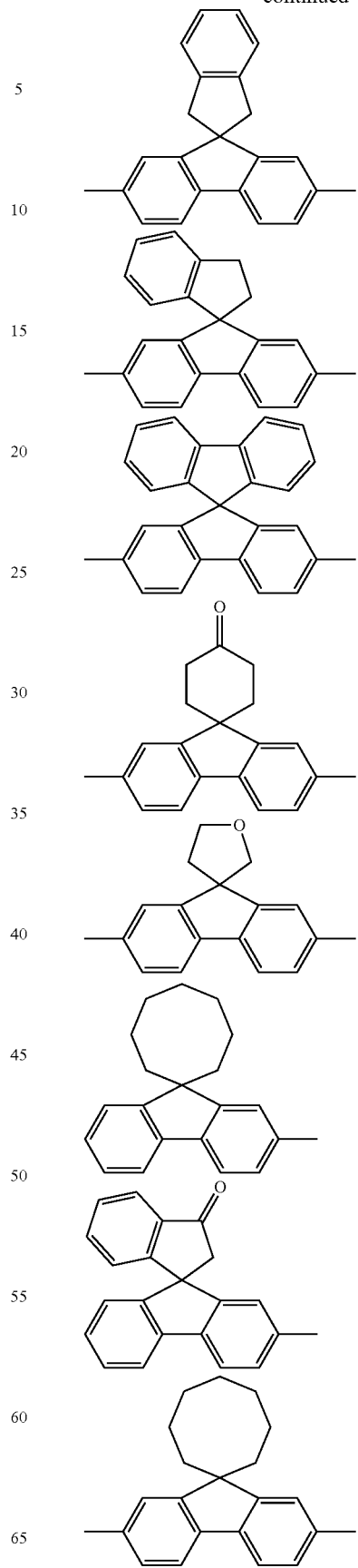

-continued

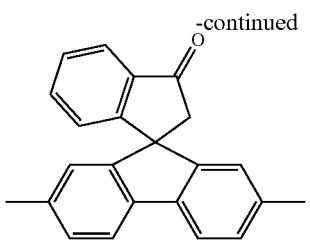

The following structures are preferable.

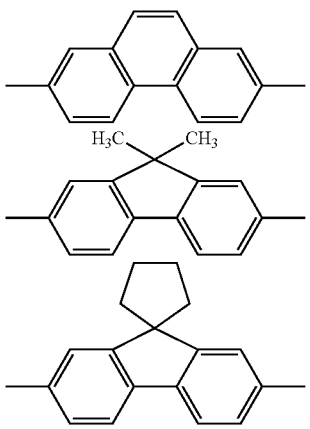

-continued

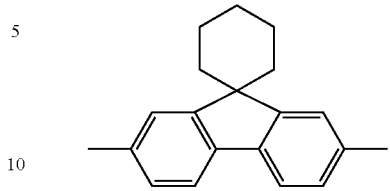

Further, it is preferred that at least one of $Ar_7$ to $Ar_{10}$ in the formula (4) and at least one of $Ar_{11}$ and $Ar_{14}$ in the formula (5) be a substituted or unsubstituted biphenyl group.

Examples of the substituted or unsubstituted biphenyl group include 2-biphenyl, 3-biphenyl, 4-biphenyl, p-terphenyl, m-terphenyl, o-terphenyl, 4'-methyl-biphenyl-4-yl, 4'-t-butyl-biphenyl-4-yl, 4'-(1-naphthyl)-biphenyl-4-yl, 4'-(2-naphthyl)-biphenyl-4-yl, 2-fluorenyl, and 9,9-dimethyl-2-fluorenyl.

Of these, 3-biphenyl, 4-biphenyl, p-terphenyl, m-terphenyl, and 9,9-dimethyl-2-fluorenyl are preferable.

The terminal of the substituted or unsubstituted biphenyl group may be substituted by an arylamino group.

Specific examples of the amine derivative which can be used in the invention are given below.

B-1

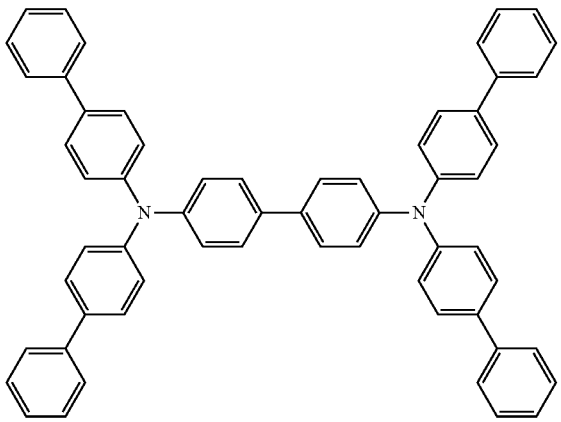

B-2

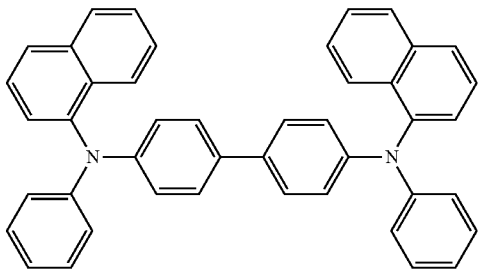

B-3

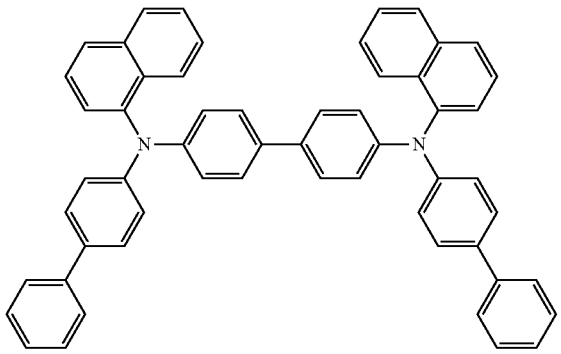

B-4

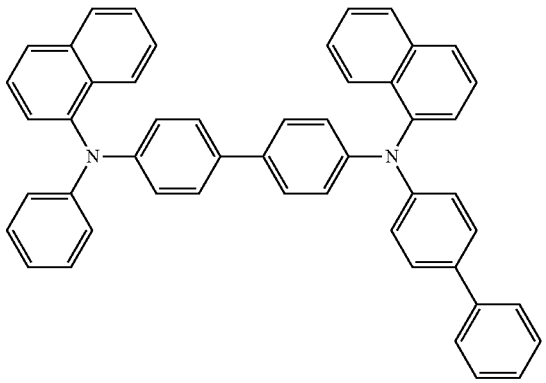

-continued
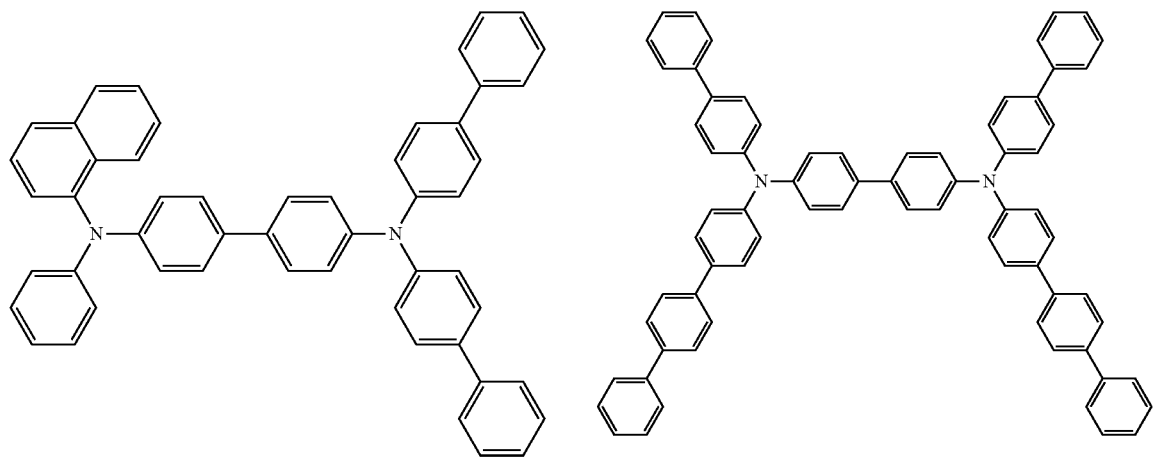
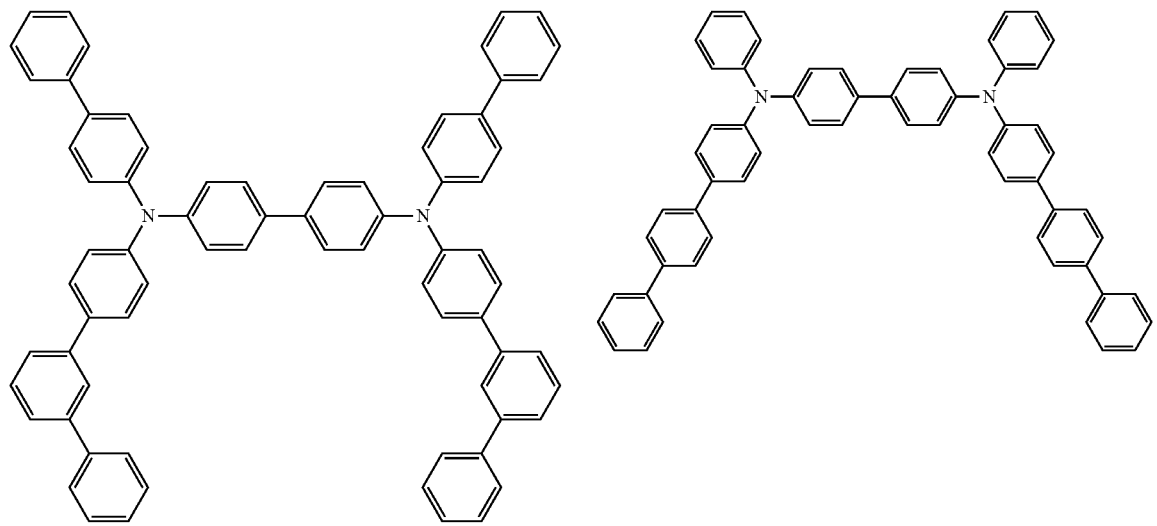
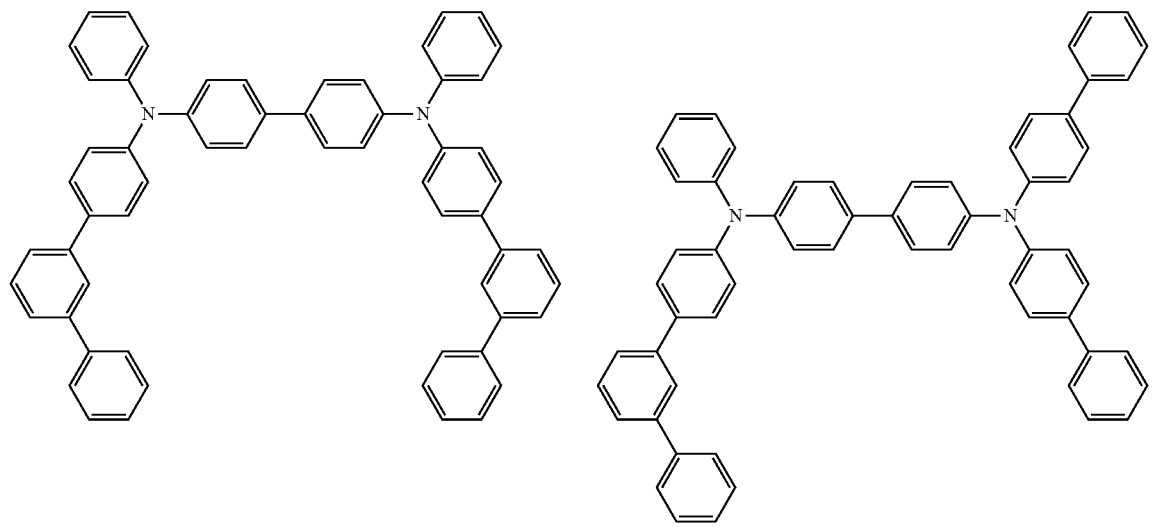

-continued
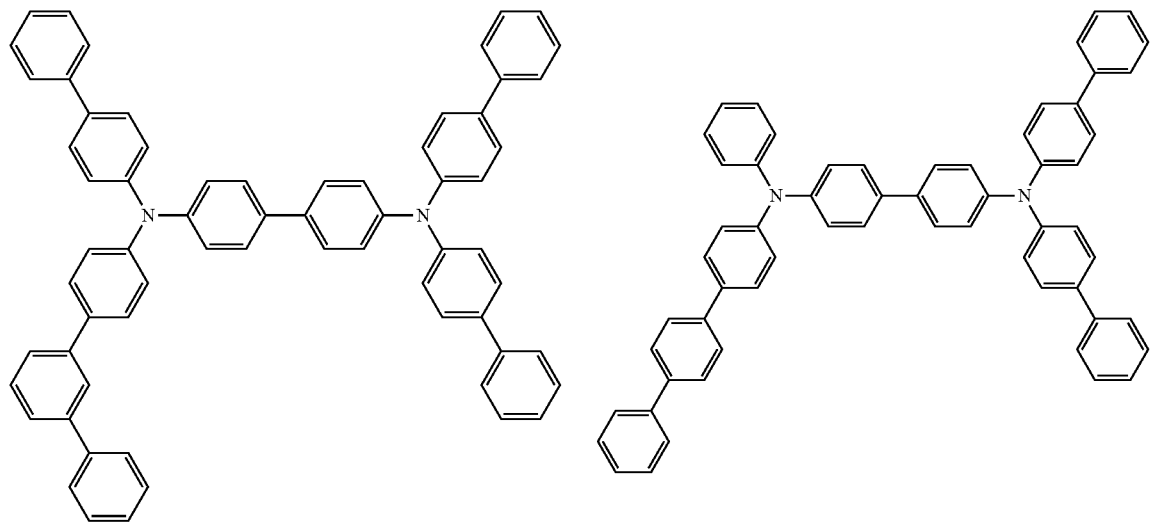
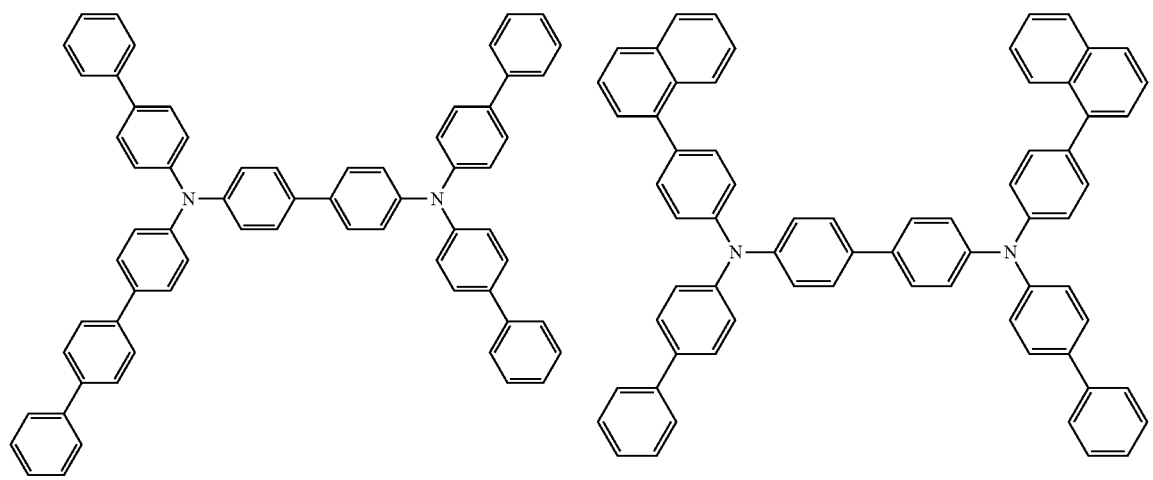
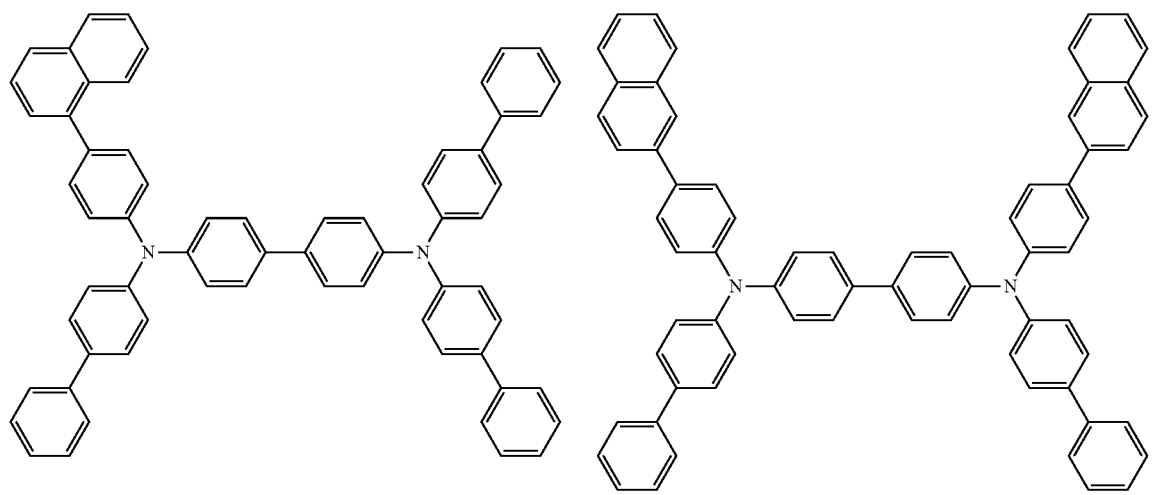

-continued
B-17
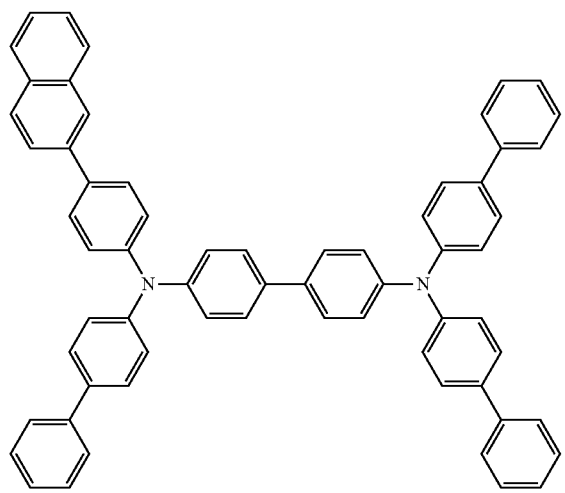
B-18
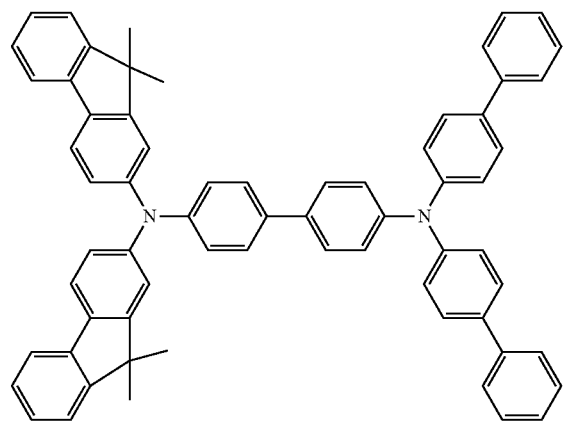
B-19
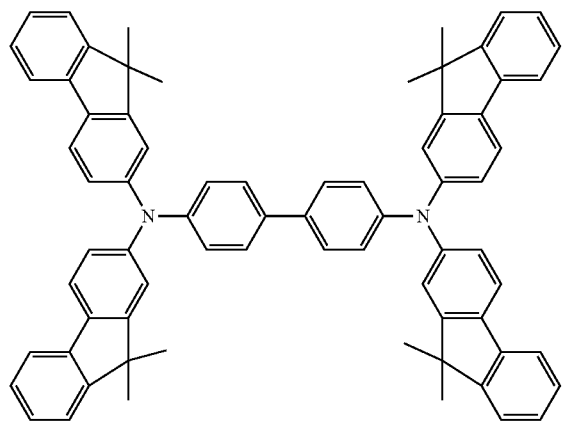
B-20
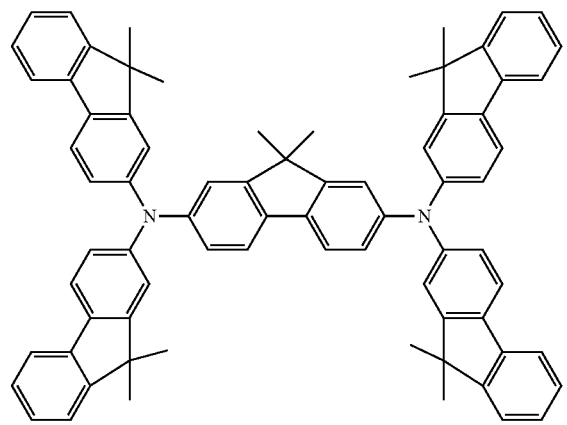
B-21
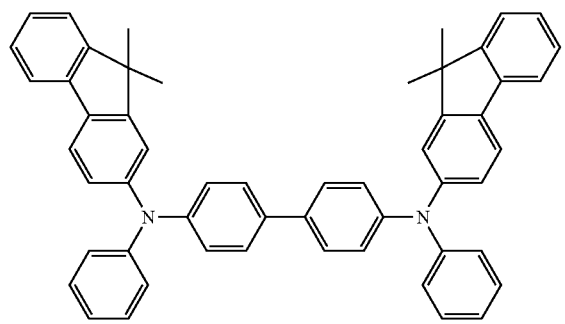
B-22
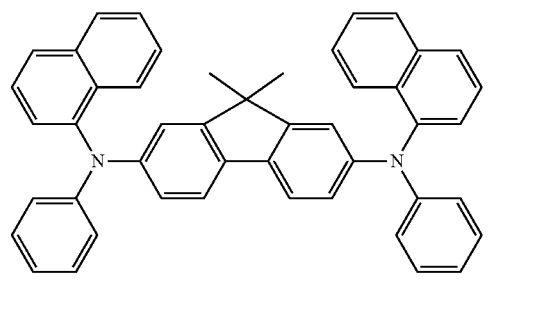

B-23
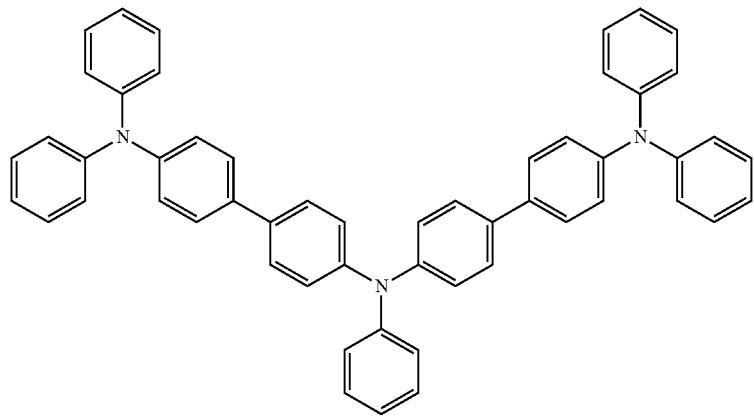
B-24
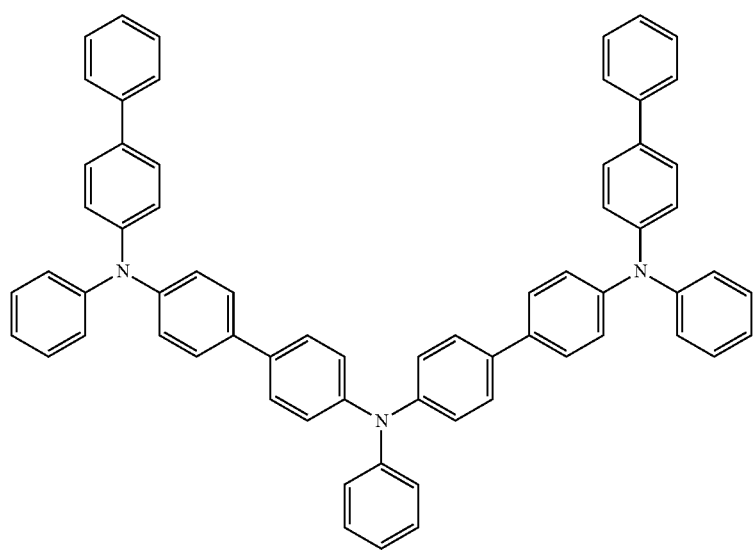
B-25
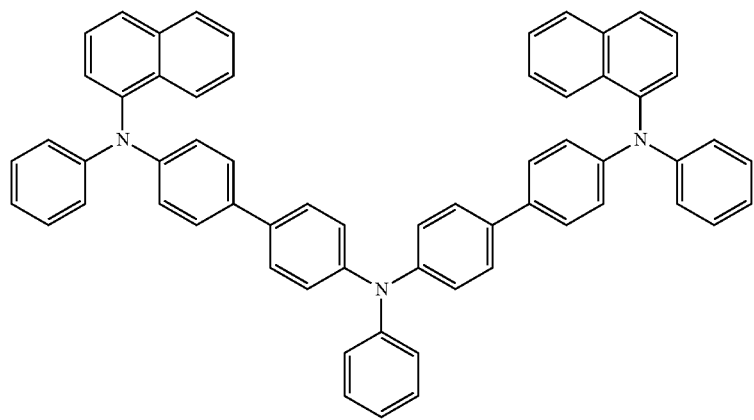

-continued
B-26
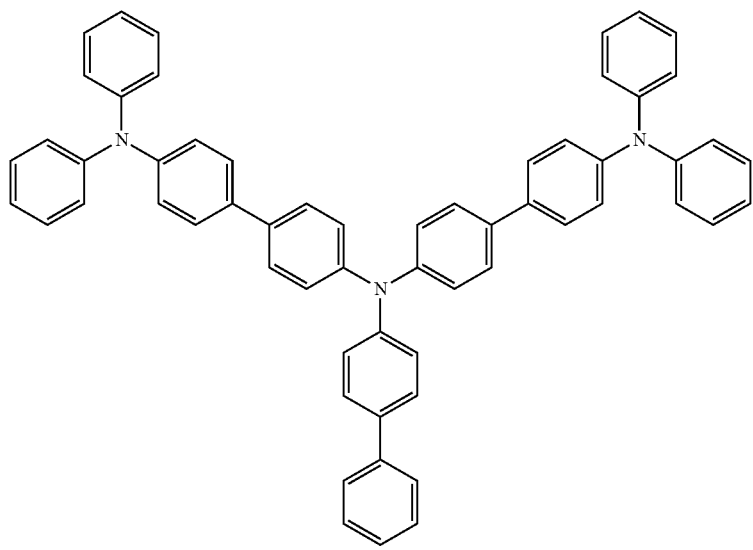
B-27
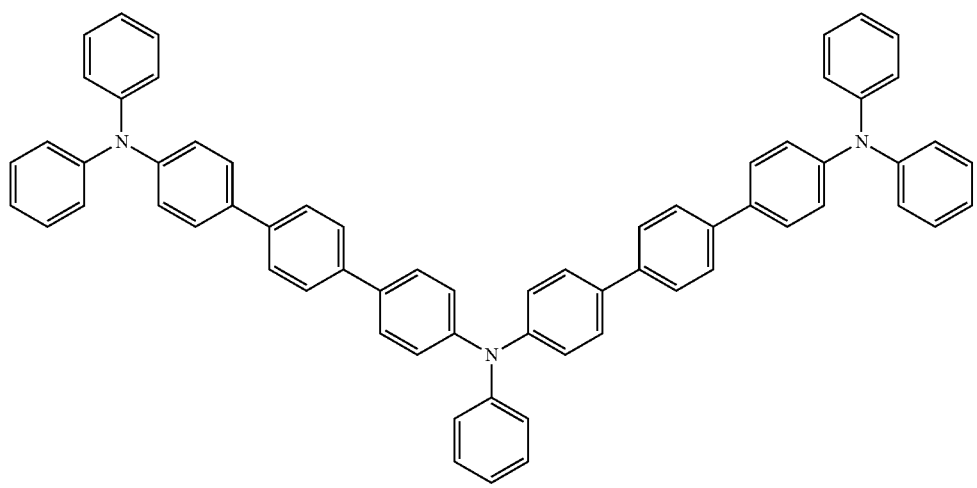
B-28
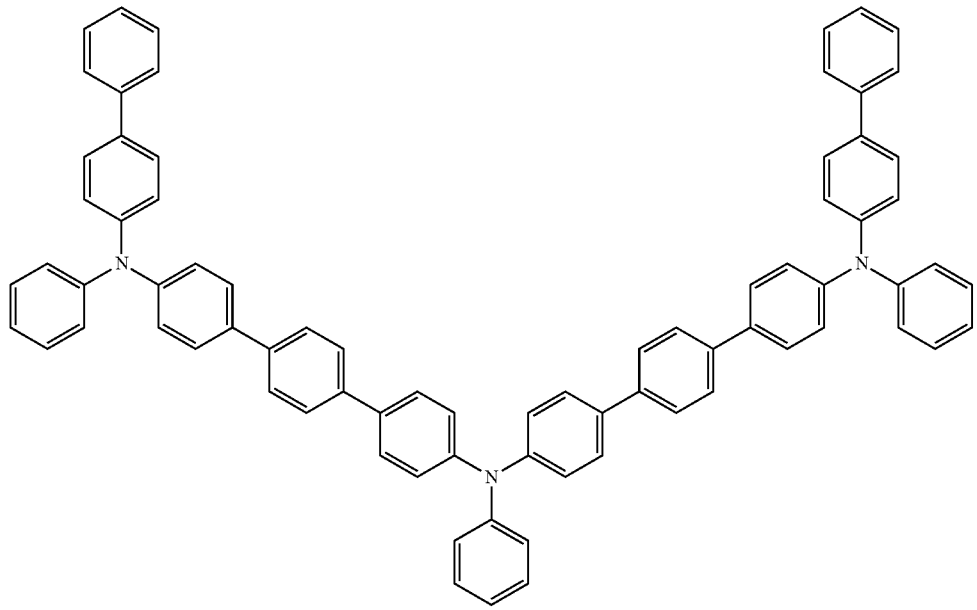

B-29
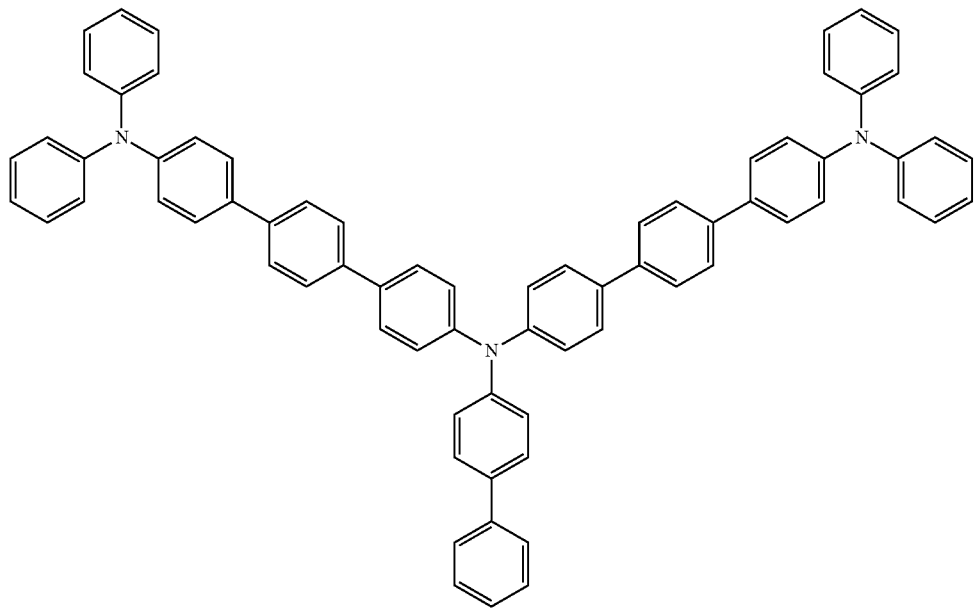
B-30
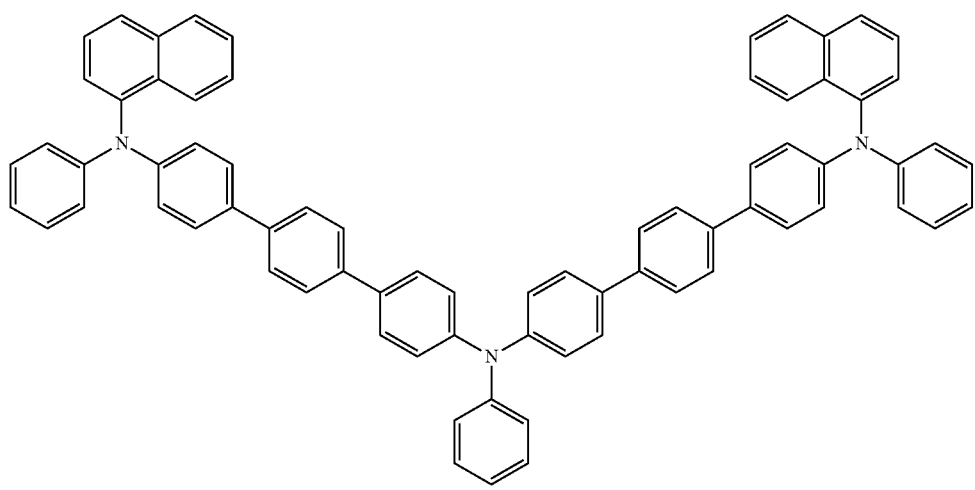
B-31
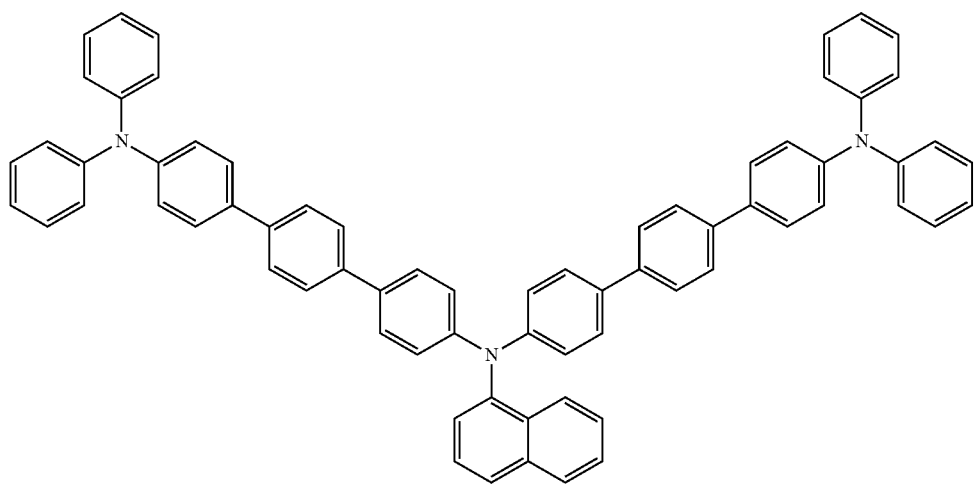

-continued
B-32
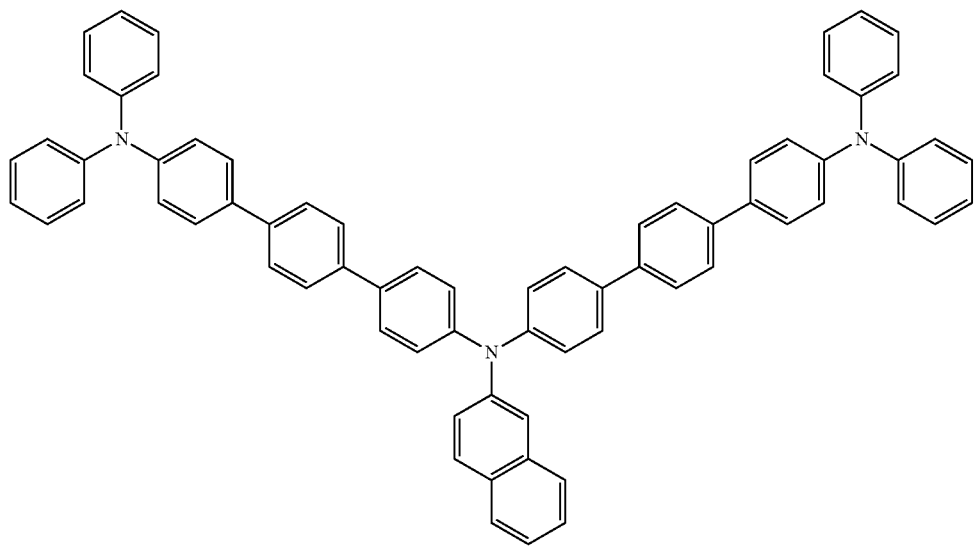
B-33
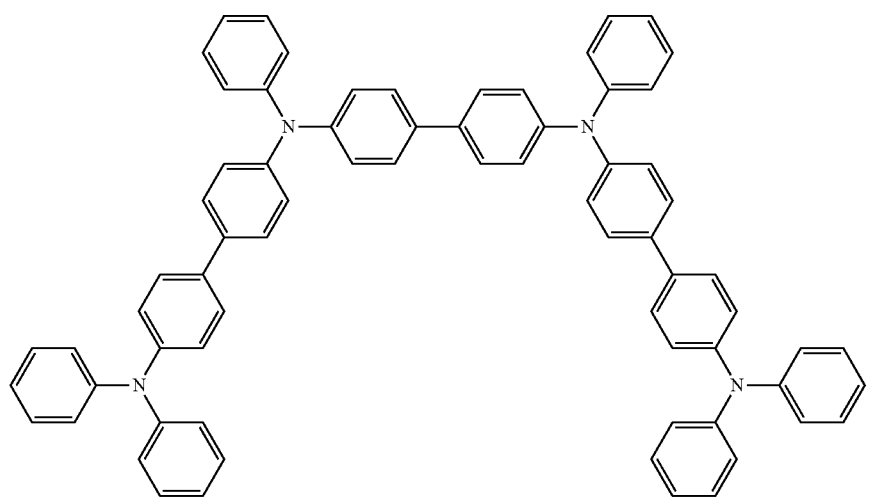
B-34
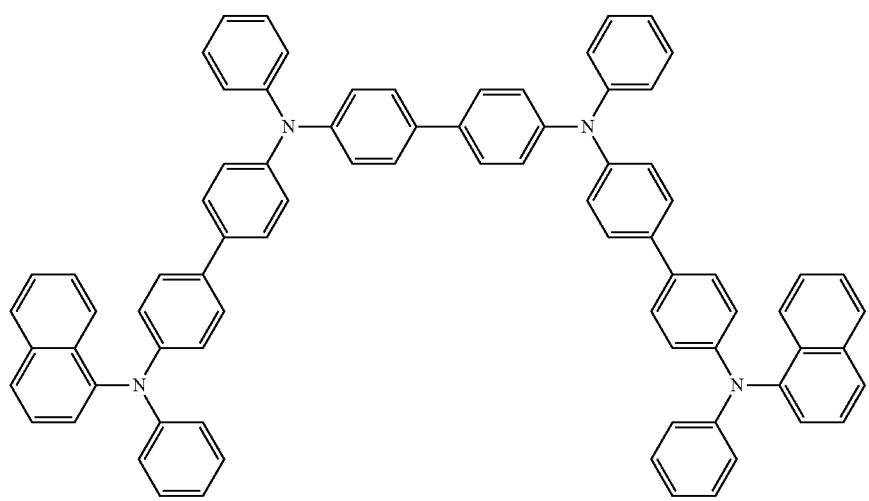

-continued
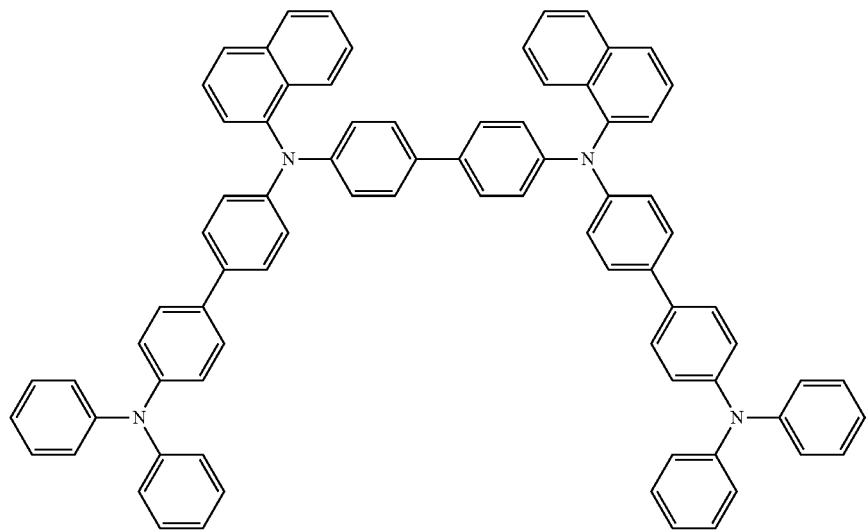
B-35
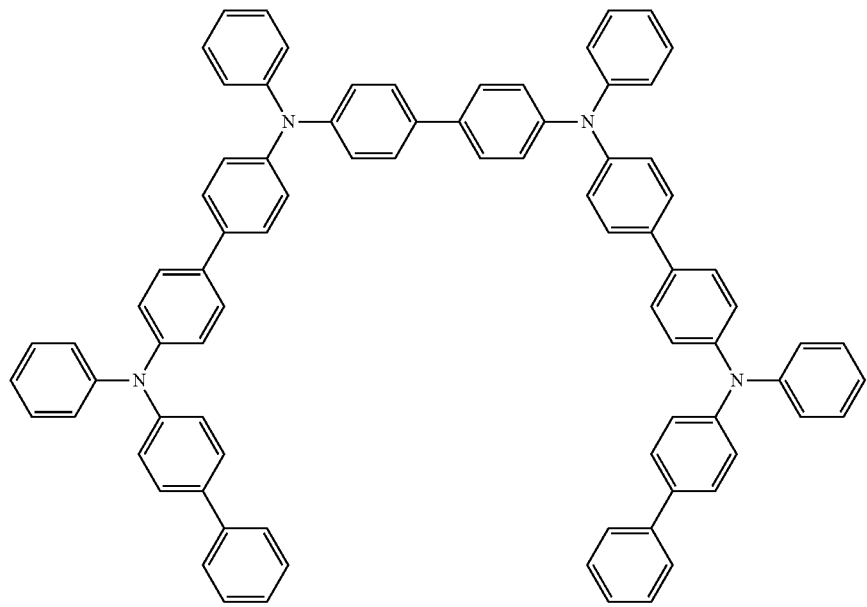
B-36
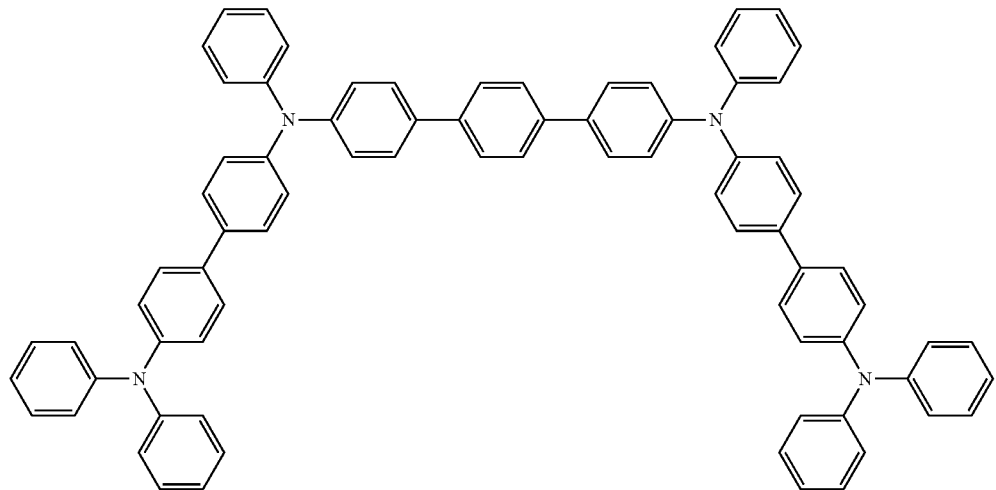
B-37

-continued

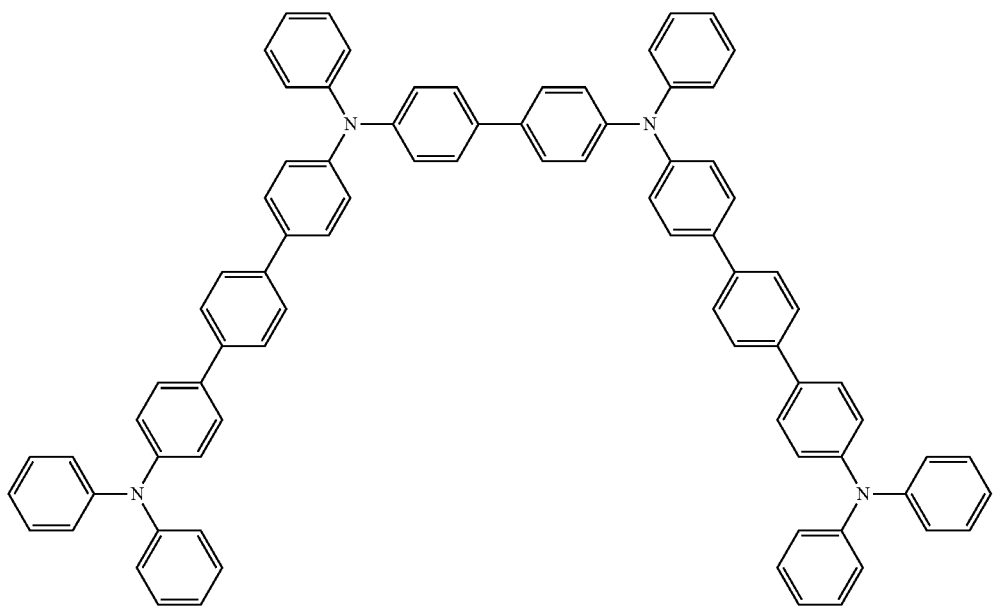
B-38

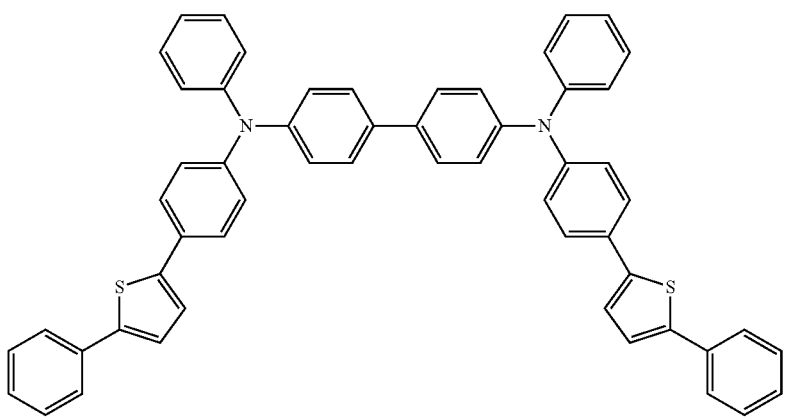
B-39

In the organic EL device of the invention, it is preferred that, of the layers provided in the hole-injecting/hole-transporting region, the layer which is in contact with the anode be a layer containing an acceptor material.

Figure 2:
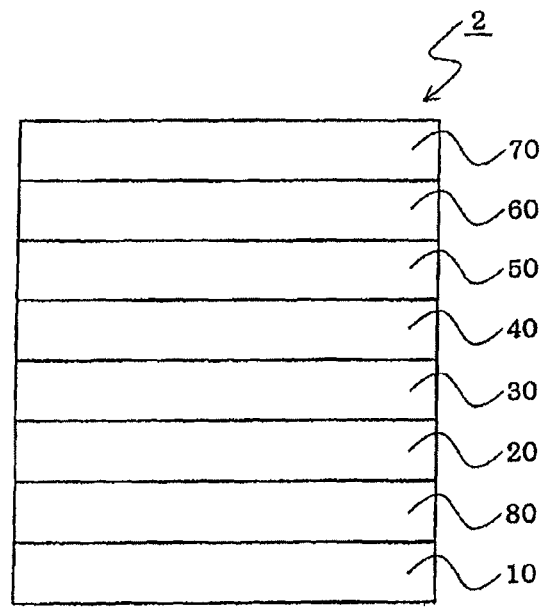
FIG. 2 is a schematic cross-sectional view showing another embodiment of an organic EL device according to the invention.

FIG. 2 is a schematic cross-sectional view showing another embodiment of the organic EL device according to the invention.

The organic EL device shown in FIG. 2 is the same as the organic EL device shown in FIG. 1, except that an acceptor-containing layer 80 is provided between the anode 10 and the hole-injecting layer 20.

A lower driving voltage can be realized by the provision of the acceptor-containing layer in such a manner that the acceptor-containing layer 80 is in contact with the anode 10, as shown in FIG. 2.

The acceptor contained in the acceptor-containing layer 80 will be explained below.

The acceptor is an organic compound which is readily-reduced.

The ease to be reduced of the compound may be measured using the reduction potential. In the invention, a compound having a reduction potential of −0.8V or more using a saturated calomel electrode (SCE) as the reference electrode is preferable, and a compound having a reduction potential greater than the reduction potential (about 0 V) of tetracyanoquinodimethane (TCNQ) is particularly preferable.

An organic compound having an electron-attracting substituent is preferable as the organic compound which is easily reduced. Specific examples of the organic compound having an electron-attracting substituent include quinoid derivatives, pyrazine derivatives, arylborane derivatives, imide derivatives, and the like can be given. The quinoid derivatives include quinodimethane derivatives, thiopyran dioxide derivatives, thioxanthene dioxide derivatives, and quinone derivatives.

As preferred examples of the quinoid derivatives, compounds of the following formulas (1a) to (1i) can be given. Note that the compounds of the formulas (1a) and (1b) are more preferable.

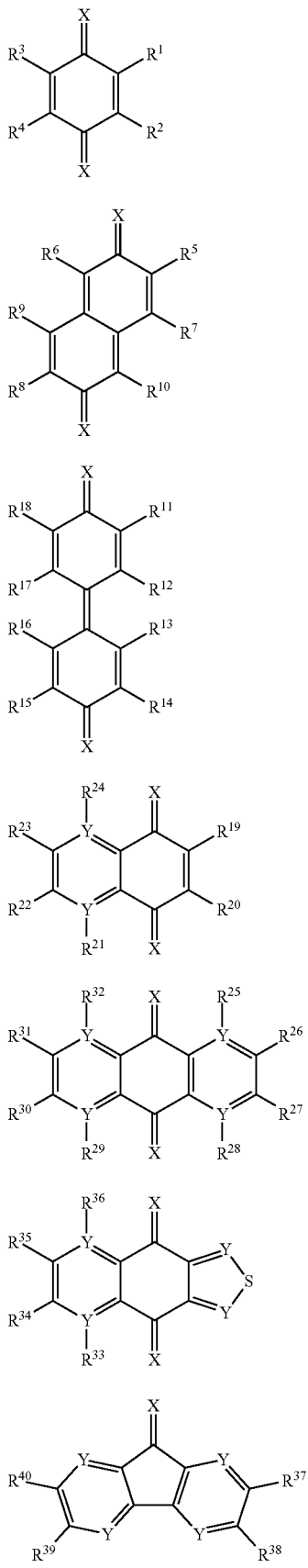

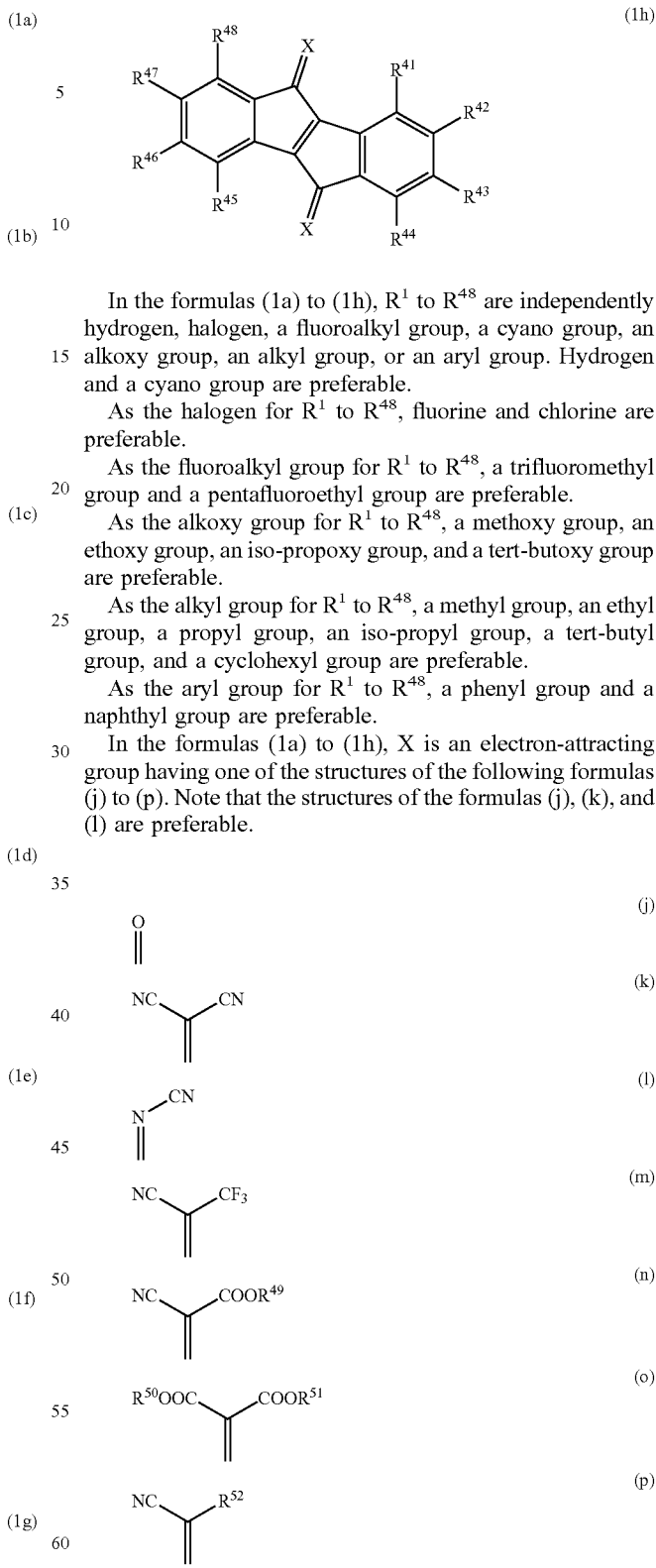

In the formulas (1a) to (1h), $R^1$ to $R^{48}$ are independently hydrogen, halogen, a fluoroalkyl group, a cyano group, an alkoxy group, an alkyl group, or an aryl group. Hydrogen and a cyano group are preferable.

As the halogen for $R^1$ to $R^{48}$, fluorine and chlorine are preferable.

As the fluoroalkyl group for $R^1$ to $R^{48}$, a trifluoromethyl group and a pentafluoroethyl group are preferable.

As the alkoxy group for $R^1$ to $R^{48}$, a methoxy group, an ethoxy group, an iso-propoxy group, and a tert-butoxy group are preferable.

As the alkyl group for $R^1$ to $R^{48}$, a methyl group, an ethyl group, a propyl group, an iso-propyl group, a tert-butyl group, and a cyclohexyl group are preferable.

As the aryl group for $R^1$ to $R^{48}$, a phenyl group and a naphthyl group are preferable.

In the formulas (1a) to (1h), X is an electron-attracting group having one of the structures of the following formulas (j) to (p). Note that the structures of the formulas (j), (k), and (l) are preferable.

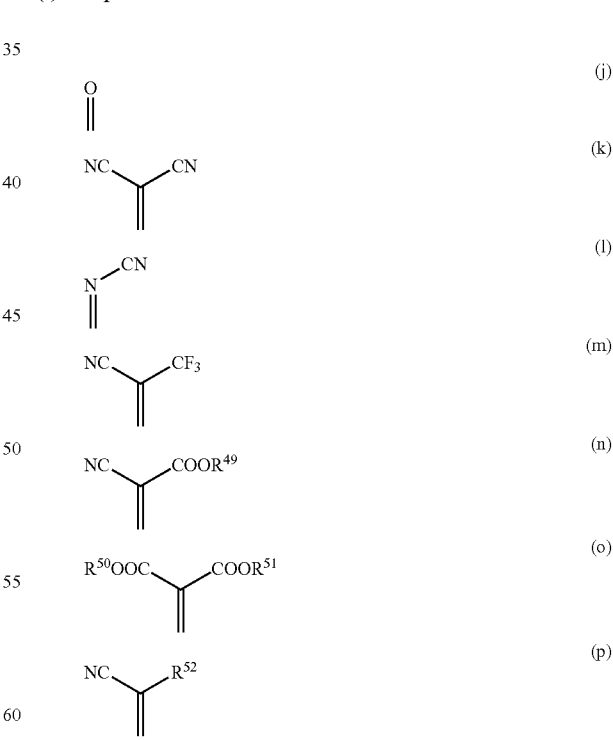

wherein $R^{49}$ to $R^{52}$ are independently hydrogen, a fluoroalkyl group, an alkyl group, an aryl group, or a heterocyclic ring, provided that $R^{50}$ and $R^{51}$ may form a ring.

The fluoroalkyl group, alkyl group, and aryl group for $R^{49}$ to $R^{52}$ are the same as those for $R^1$ to $R^{48}$.

As the heterocyclic ring for $R^{49}$ to $R^{52}$, substituents of the following formulas are preferable.

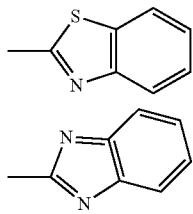
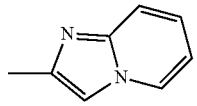
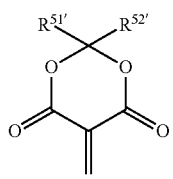

When $R^{50}$ and $R^{51}$ form a ring, X is preferably a substituent of the following formula.

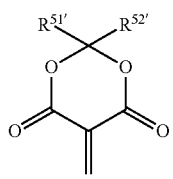

wherein $R^{51'}$ and $R^{52'}$ are independently a methyl group, an ethyl group, a propyl group, or a tert-butyl group.

In the formulas (1a) to (1h), Y is —N= or —CH=.

As specific examples of the quinoid derivatives, the following compounds can be given.

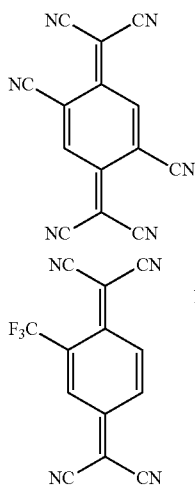
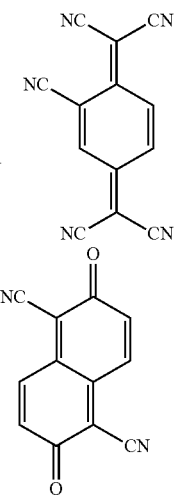
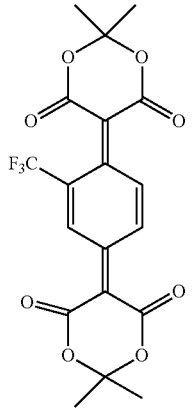
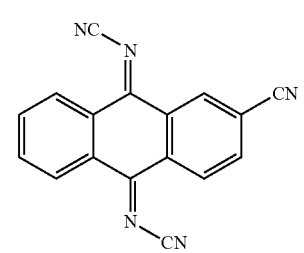
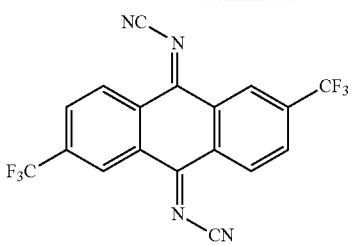
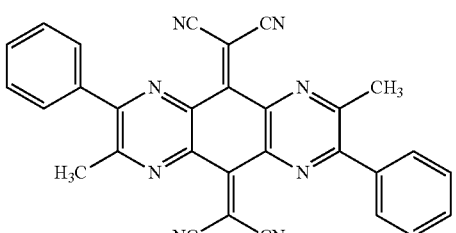
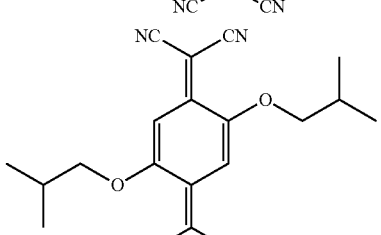
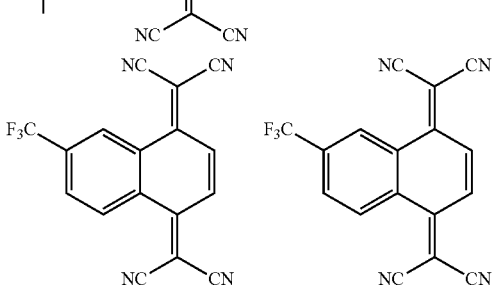
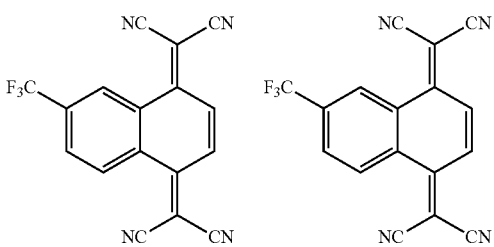

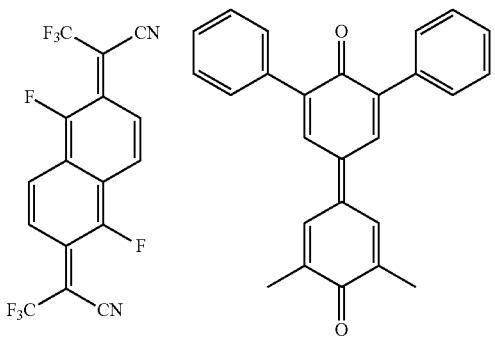

Compounds of the following formula (2) can be given as examples of the arylborane derivatives.

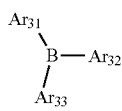 (2)

In the formula (2), $Ar_{31}$ to $Ar_{33}$ are independently an aryl group or a heterocyclic ring having an electron-attracting group.

As the aryl group having an electron-attracting group represented by $Ar_{31}$ to $Ar_{33}$, a pentafluorophenyl group, a heptafluoronaphthyl group, and a pentafluorophenyl group are preferable.

As the heterocyclic ring having an electron-attracting group represented by $Ar_{31}$ to $Ar_{33}$, a quinoline ring, a quinoxaline ring, a pyridine ring, a pyrazine ring, and the like are preferable.

As specific examples of the arylborane derivatives, the following compounds can be given.

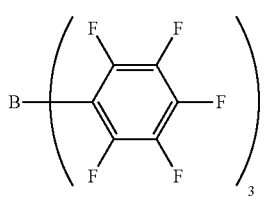

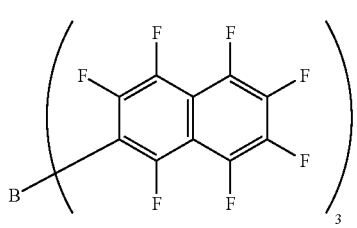

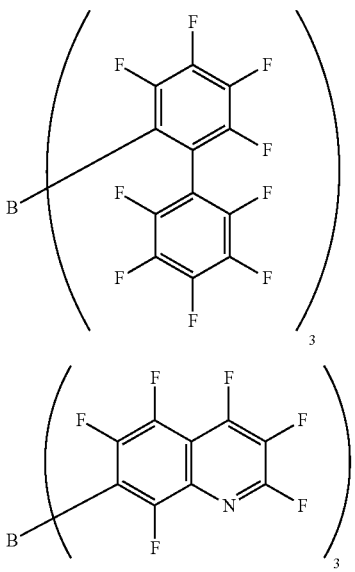

The arylborane derivative is preferably a compound having at least one fluorine as the substituent for the aryl, and particularly preferably tris-β-(pentafluoronaphthyl)borane (PNB).

Compounds of the following formula (3a) can be given as examples of the thiopyran dioxide derivatives, and compounds of the following formula (3b) can be given as examples of the thioxanthene dioxide derivatives.

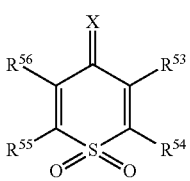 (3a)

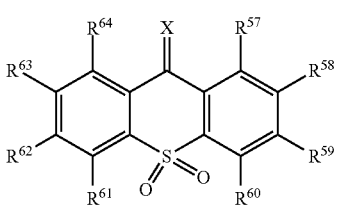 (3b)

In the formulas (3a) and (3b), $R^{53}$ to $R^{64}$ are independently hydrogen, halogen, a fluoroalkyl group, a cyano group, an alkyl group, or an aryl group. Hydrogen and a cyano group are preferable.

In the formulas (3a) and (3b), X is an electron-attracting group which is the same as X in the formulas (1a) to (1i). The structures of the formulas (i), (j), and (k) are preferable.

The halogen, fluoroalkyl group, alkyl group, and aryl group represented by $R^{53}$ to $R^{64}$ are the same as those for $R^1$ to $R^{48}$.

Specific examples of the thiopyran dioxide derivatives of the formula (3a) and the thioxanthene dioxide derivatives of the formula (3b) are given below.

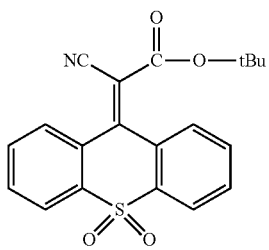

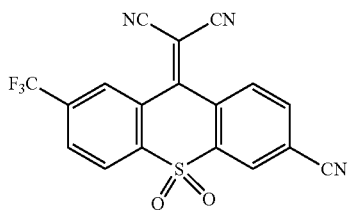

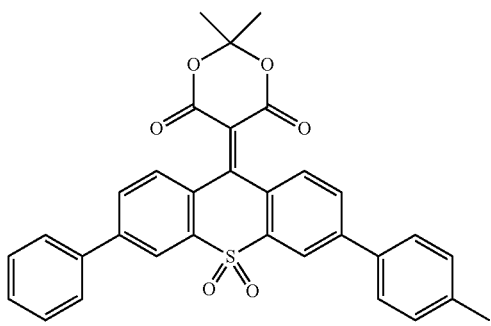

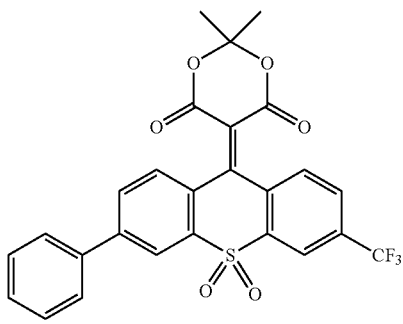

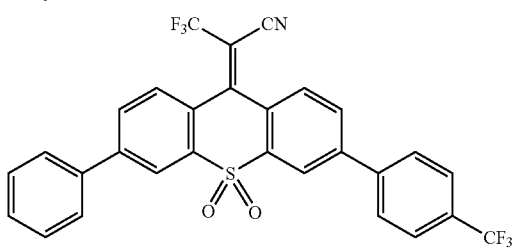

wherein tBu is a t-butyl group.

As the imide derivatives, naphthalenetetracarboxylic acid diimide compounds and pyromellitic acid diimide compounds are preferable.

Other than those mentioned above, a nitrogen-containing heterocyclic derivative represented by the following formula (4a), which is disclosed in Japanese Patent No. 3571977, can also be used.

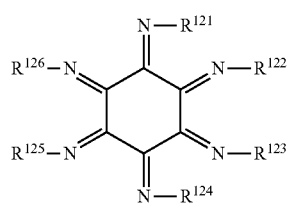

(4a)

wherein $R^{121}$ to $R^{126}$ are independently a substituted or unsubstituted alkyl group, a substituted or unsubstituted aryl group, a substituted or unsubstituted aralkyl group, or a substituted or unsubstituted heterocyclic group, provided that $R^{121}$ to $R^{126}$ may be the same or different. $R^{121}$ and $R^{122}$, $R^{123}$ and $R^{124}$, $R^{125}$ and $R^{126}$, $R^{121}$ and $R^{126}$, $R^{122}$ and $R^{123}$, and $R^{124}$ and $R^{125}$ may form a condensed ring.

Further, a compound of the following formula (4b), as disclosed in U.S. Patent Publication No. 2004/0113547, can also be used.

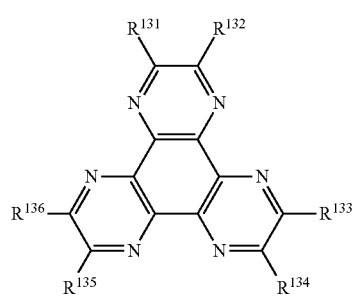

(4b)

wherein $R^{131}$ to $R^{136}$ are a substituent, preferably, an electron-attracting group such as cyano, nitro, sulfonyl, carbonyl, trifluoromethyl, and halogen.

Specific examples of the compounds represented by the formula (4b) are illustrated below. In the following formula, Me and Ph are methyl and phenyl, respectively.

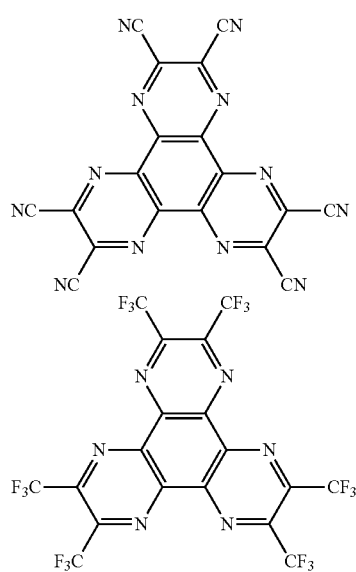

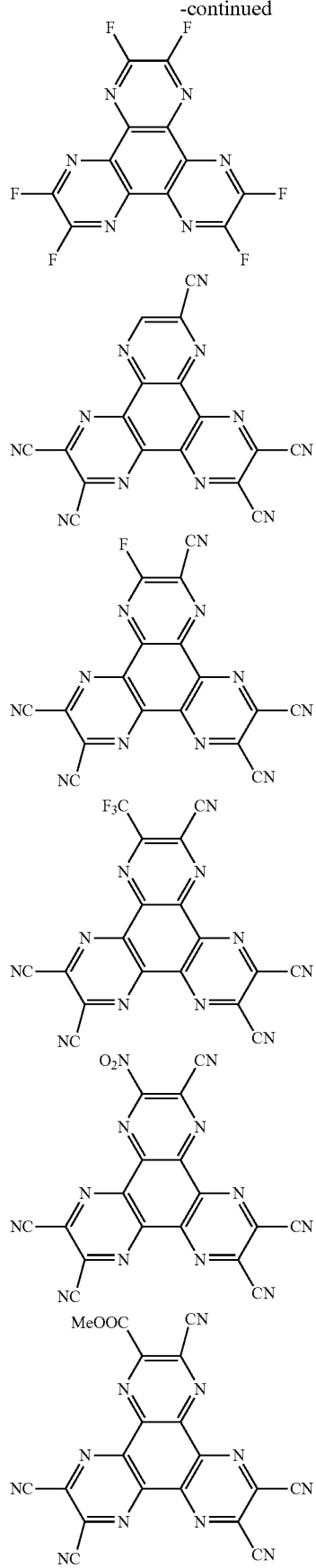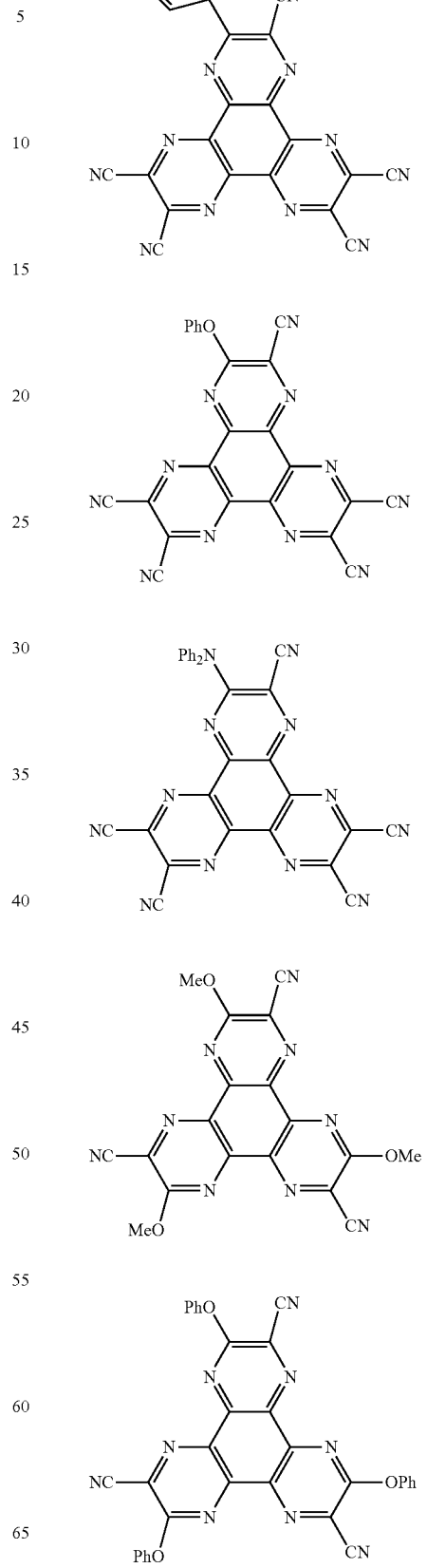

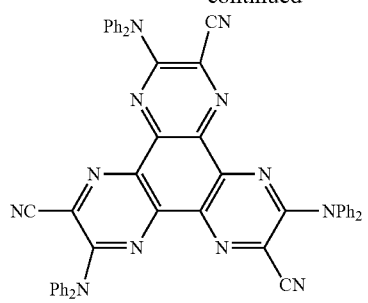
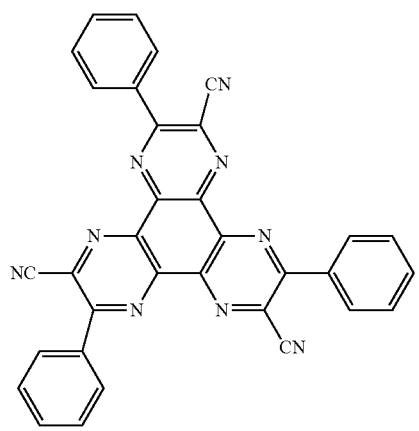
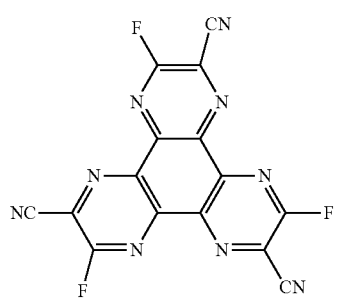
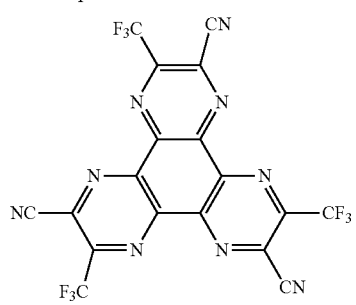
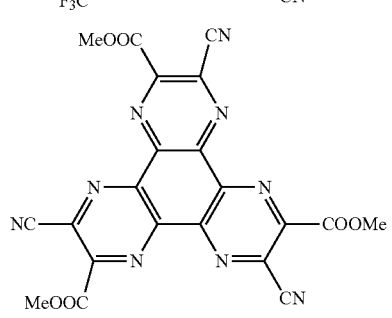
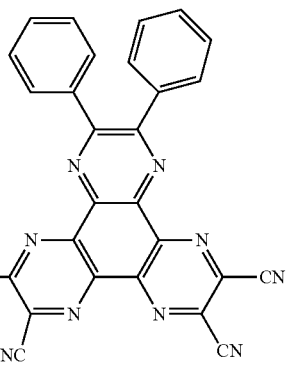
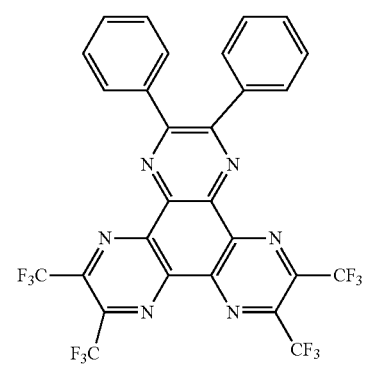
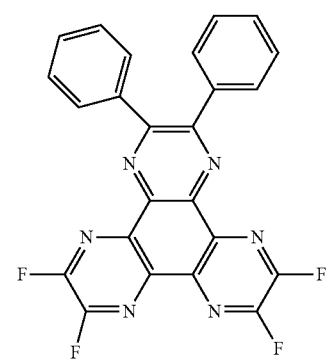
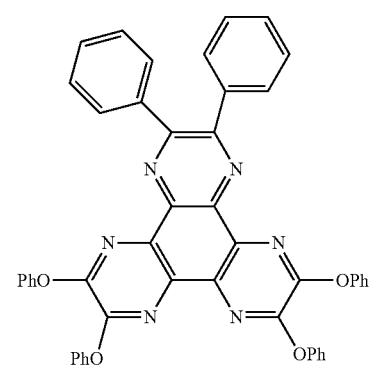

71
-continued
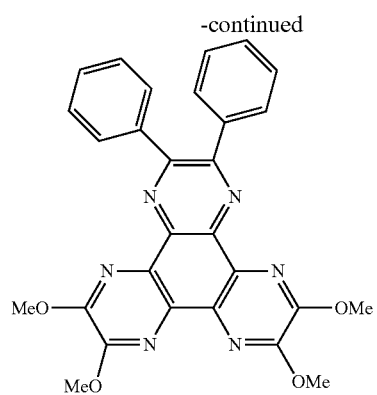
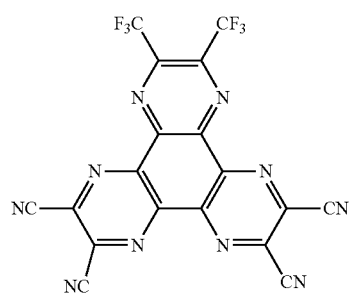
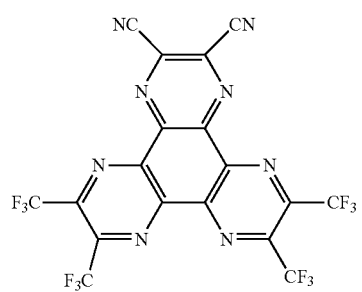
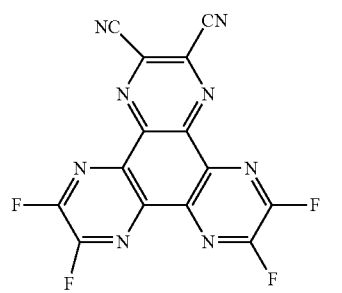
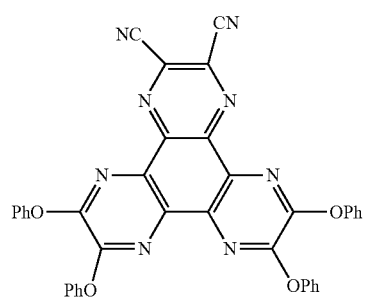
72
-continued
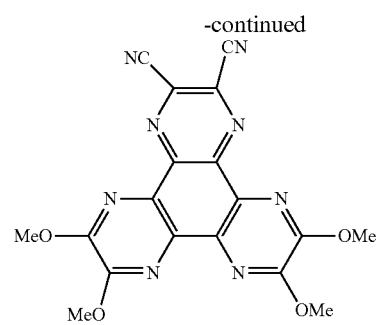
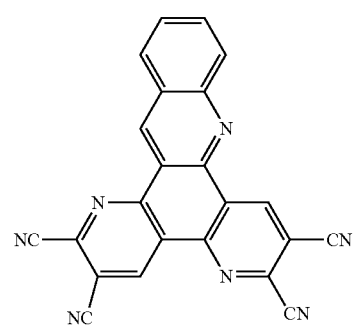
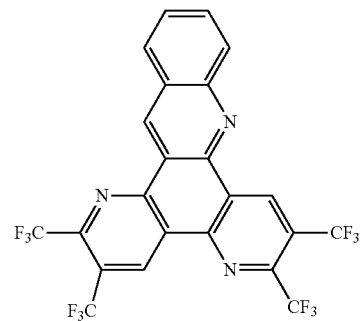
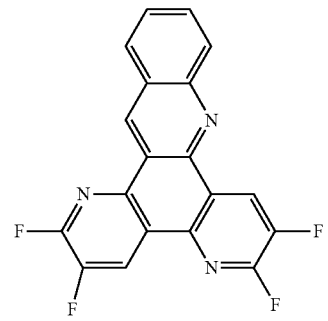
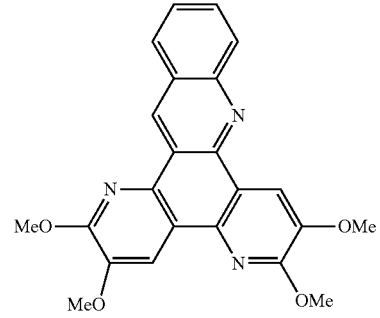

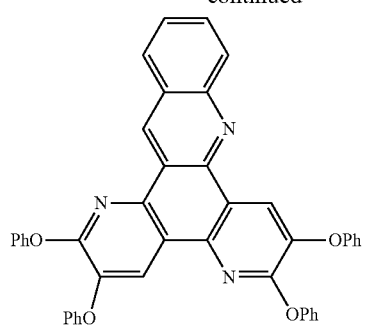
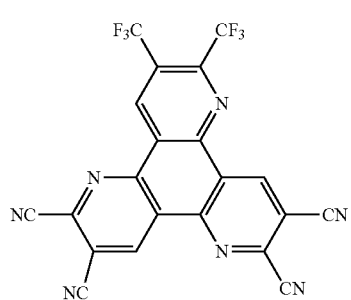
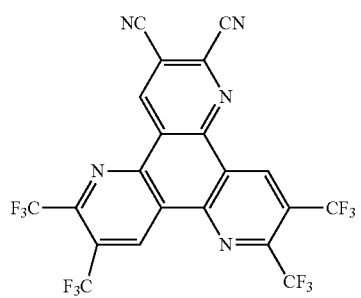
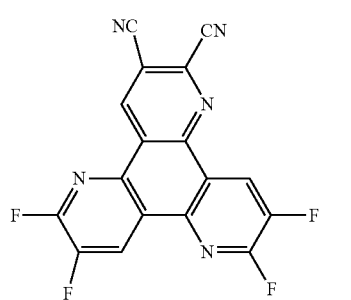
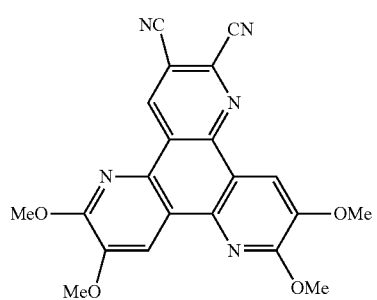
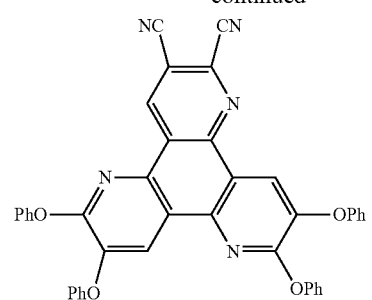
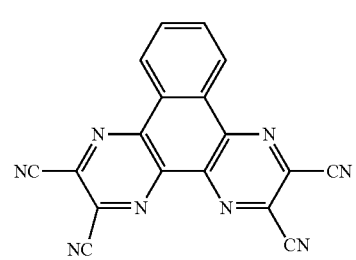
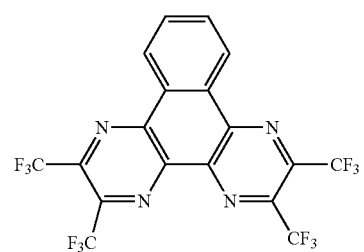
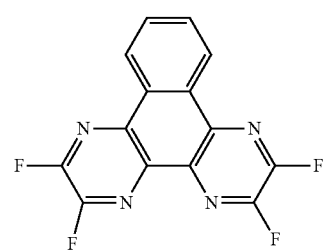
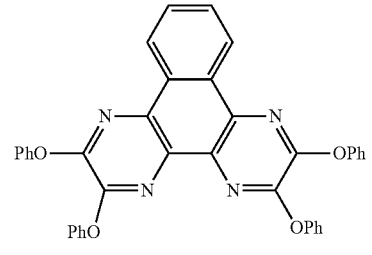
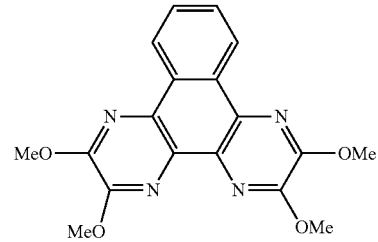

-continued
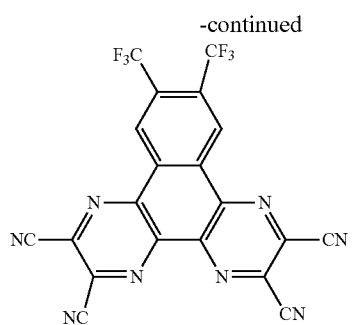
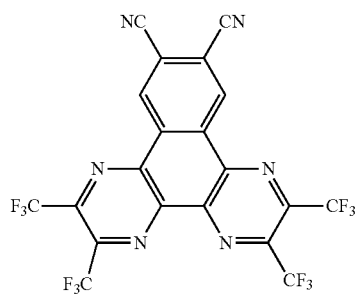
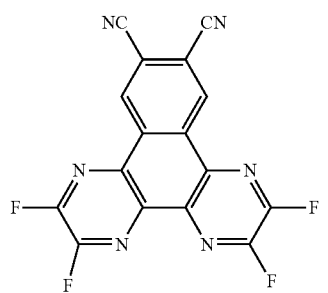
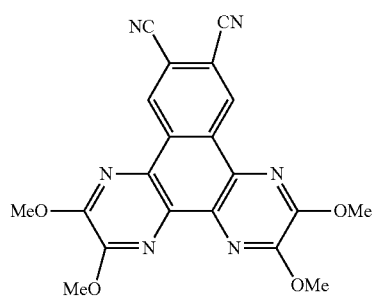
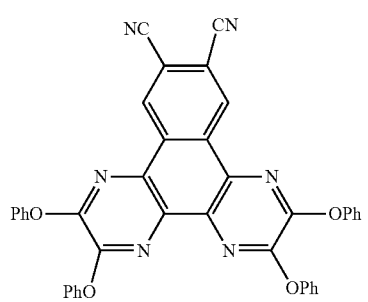
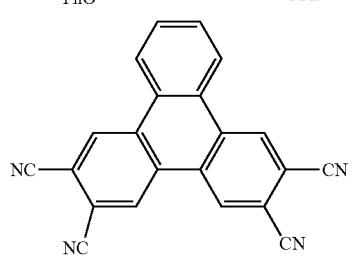
-continued
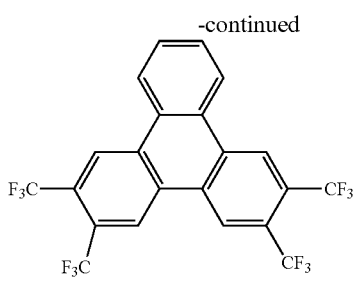
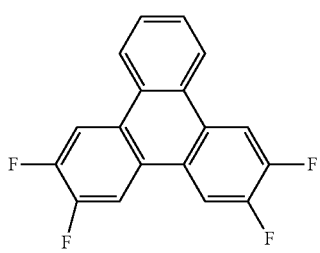
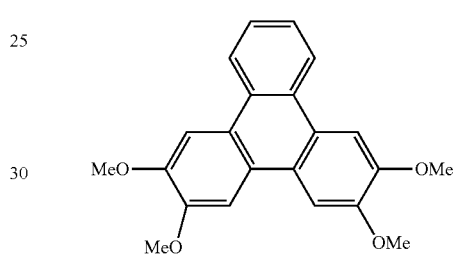
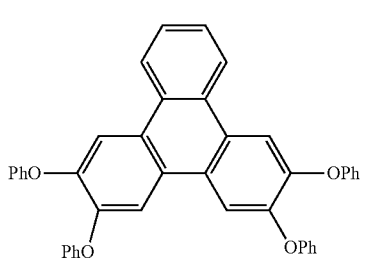
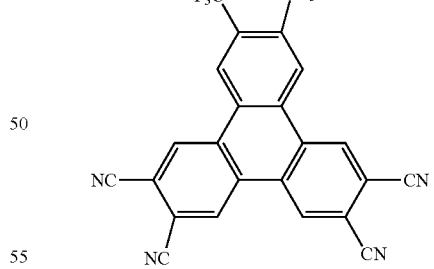
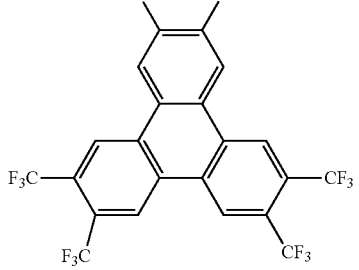

-continued
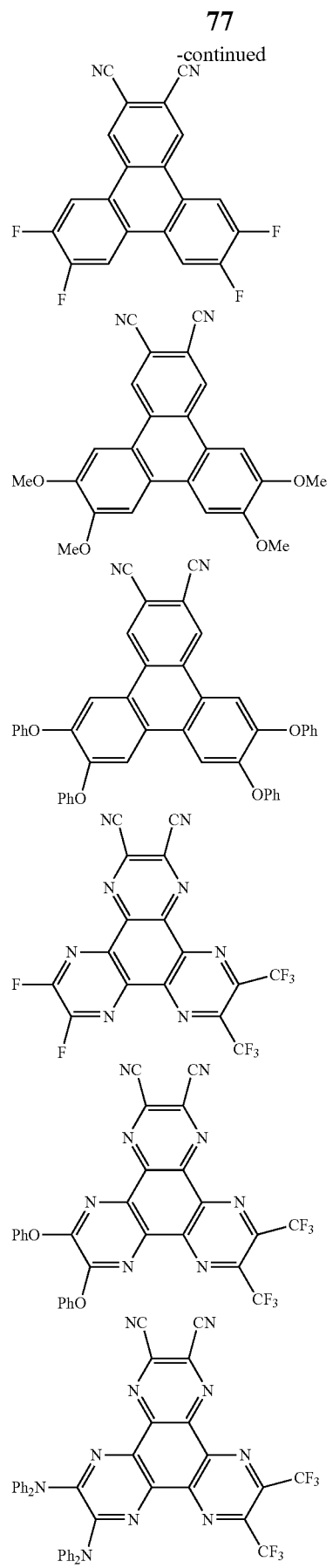
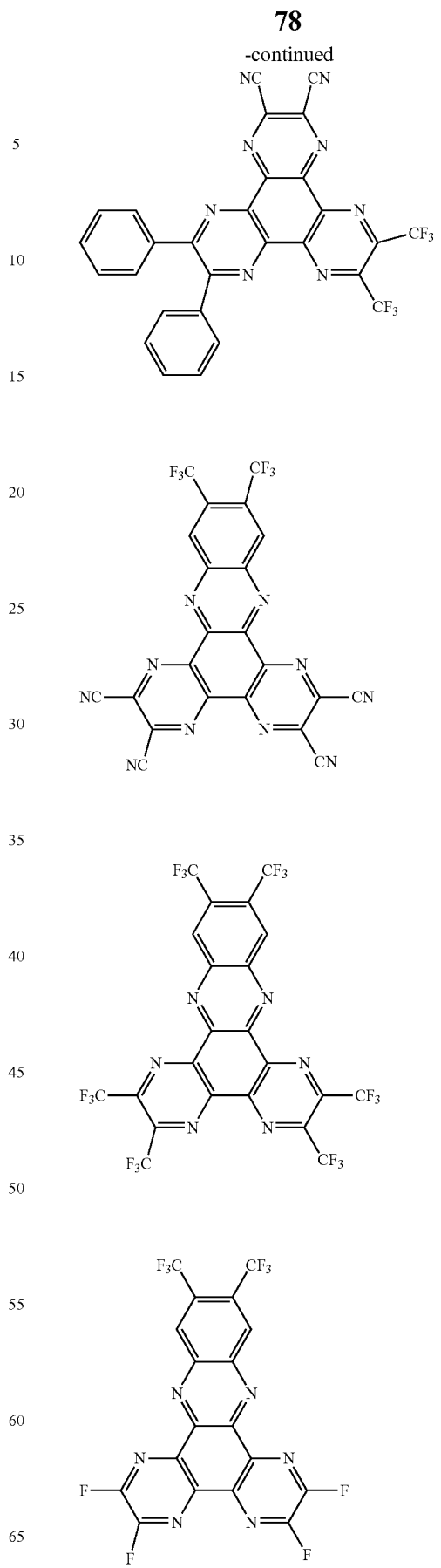

-continued

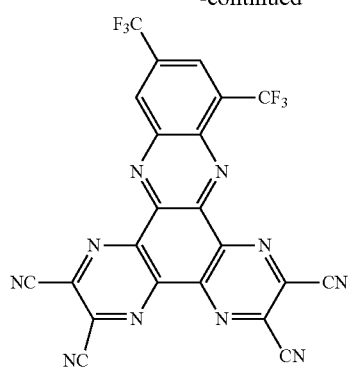

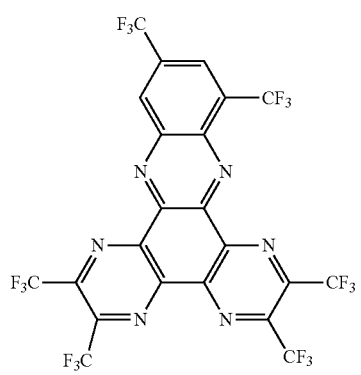

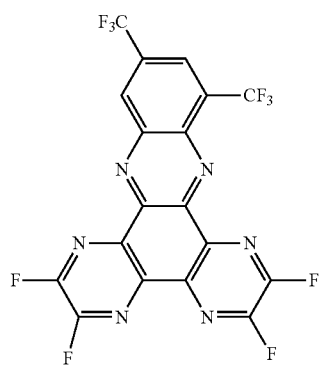

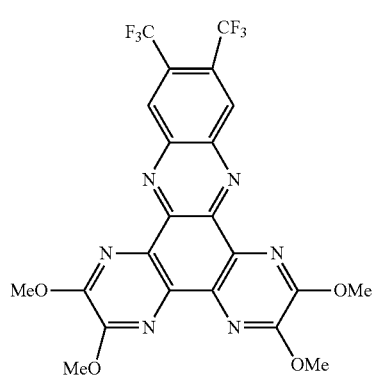

-continued

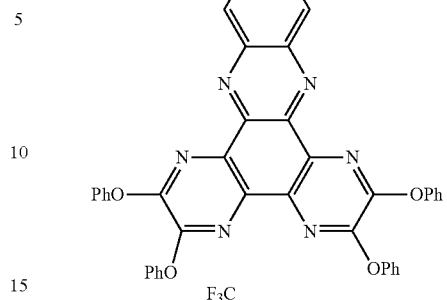

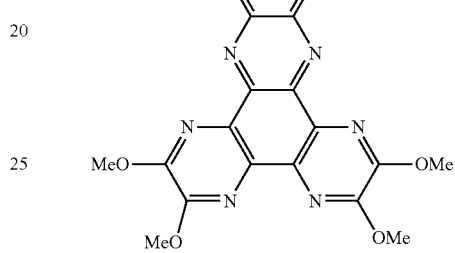

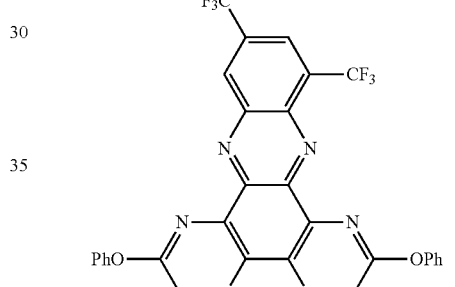

Further, the compounds of the following formula (5a) can be given.

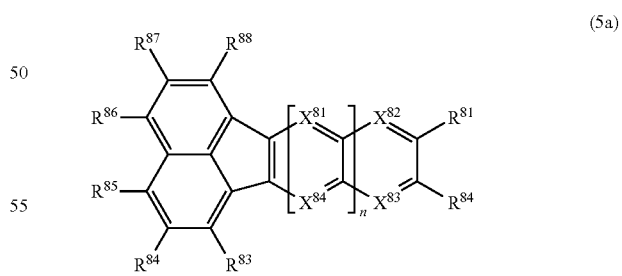

(5a)

wherein $R^{81}$ to $R^{88}$, which may be the same or different, are selected from a group consisting of hydrogen, a substituted or unsubstituted alkyl group, a substituted or unsubstituted aryl group, a substituted or unsubstituted heterocyclic ring, halogen, a cyano group, a nitro group, an ester group, an amide group, an alkoxy group, a substituted or unsubstituted phenoxy group and an amino group; the adjacent atoms or groups represented by $R^{81}$ to $R^{88}$ may be bonded to each other to form a ring structure; $X^{81}$ to $X^{84}$ are independently a carbon atom or a nitrogen atom, and n is an integer of 0 or more.

Specific examples of the compounds represented by the formula (5a) are given below.

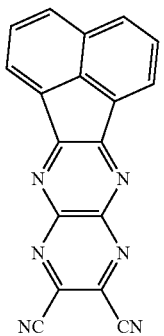 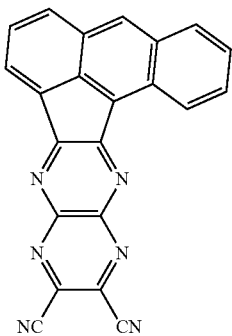

Representative examples of the structure of the organic EL device of the invention are shown below. The invention is, however, not limited to these.
(1) Anode/hole-injecting layer/hole-transporting layer/emitting layer/electron-transporting layer/cathode
(2) Anode/hole-injecting layer/hole-transporting layer/emitting layer/electron-transporting layer/electron-injecting layer/cathode (FIG. 1)
(3) Anode/hole-injecting layer/hole-transporting layer/emitting layer/electron-transporting layer/insulative layer/cathode
(4) Anode/insulative layer/hole-injecting layer/hole-transporting layer/emitting layer/electron-transporting layer/electron-injecting layer/insulative layer/cathode
(5) Anode/acceptor-containing layer/hole-injecting layer/hole-transporting layer/emitting layer/electron-transporting layer/electron-injecting layer/cathode (FIG. 2)

The light emitted by the emitting layer may be outcoupled through either the anode or the cathode, or through both.

In the organic EL device, the region between the anode and the cathode may have a cavity structure; i.e., a structure in which the light emitted by the emitting layer is reflected between the anode and the cathode. For example, the cathode is formed of a semi-transparent and semi-reflective material, and the anode has a light-reflective surface. In this case, emission, which is multi-interfered between the light-reflective surface of the anode and the light-reflective surface of the cathode, is outcoupled through the cathode. The optical distance between the light-reflective surface of the anode and the light-reflective surface of the cathode is determined according to the wavelength of light which is desired to be outcoupled. The thickness of each layer is determined in such a manner that such an optical distance can be obtained. In the organic EL device of top-emission type (emission is outcoupled outside the device without passing through the support substrate), it is possible to improve outcoupling efficiency and control the emission spectrum by the active use of such a cavity structure.

Each member of the organic EL device according to the invention is described below.
(Substrate)

The organic EL device of the invention is formed on a transparent substrate. The transparent substrate is a substrate for supporting the organic EL device, and is preferably a flat and smooth substrate having a transmittance of 50% or more to rays within visible ranges of 400 to 700 nm.

Specific examples thereof include glass plates and polymer plates. Examples of the glass plate include soda-lime glass, barium/strontium-containing glass, lead glass, aluminosilicate glass, borosilicate glass, barium borosilicate glass, and quartz. Examples of the polymer plate include polycarbonate, acrylic polymer, polyethylene terephthalate, polyethersulfide, and polysulfone.

In the case of a top-emission type organic EL device in which light is outcoupled through the side opposite to the substrate, the substrate is not necessarily transparent.
[Anode]

The anode of the organic thin film EL device plays a role for injecting holes into its hole-transporting layer or emitting layer. The anode effectively has a work function of 4.5 eV or more. Specific examples of the anode material used in the invention include metals such as aluminum (Al), chlormium (Cr), molybdenum (Mo), tungsten (W), cupper (Cu), silver (Ag) and gold (Au), alloys thereof, and oxides of these metals and alloys. Further, alloys of tin oxide ($SnO_2$) and antimony (Sb), ITO (indium tin oxide), InZnO (indium zinc oxide), and alloys of zinc oxide (ZnO) and aluminum (Al) may also be used alone or in combination.

In the case where emission from the emitting layer is outcoupled through the anode, the transmittance of the anode to the emission is preferably more than 10%.

In the case where emission from the emitting layer is outcoupled through the cathode, it is preferred that the anode be a reflective electrode. In this case, the anode may be of a stacked structure of a first layer improved in light reflectance and a second layer provided thereon and having a light transmissibility and a large work function.

For example, the first layer is formed of an alloy containing aluminum as the main component. The secondary component may be one which contains at least one element which has a relatively small work function as compared with aluminum. Preferred examples of such secondary component include a lanthanide-series element. The work function of a lanthanide-series element is not large. However, presence of such an element improves stability and hole-injection property of the anode. Besides the lanthanide-series element, an element such as silicon (Si) and cupper (Cu) may be contained as the secondary element.

As for the content of the secondary element in the aluminum alloy layer constituting the first layer, if the secondary element is Nd, Ni, Ti or the like, which serves to stabilize aluminum, it is preferred that the total content of the secondary element be 10 wt % or less. With this content, the aluminum alloy layer can be kept stable while maintaining the reflectance in the aluminum alloy layer during the production of the organic EL device. In addition, working accuracy, chemical stability, and conductivity of the anode, as well as adhesion of the anode to the substrate can also be improved.

The second layer may be formed of at least one of an oxide of aluminum alloy, an oxide of molybdenum, an oxide of zirconium, an oxide of chromium, and an oxide of tanthallium. If the secondary layer is a layer formed of an oxide of an aluminum alloy (including a naturally oxidized film) containing a lanthanide-series element as the secondary element, transmittance of the secondary layer is improved due to high transmittance of the oxide of the lanthanide-series element. Therefore, a high reflectivity can be maintained on the surface of the first layer. Further, the secondary layer may be a transparent conductive layer formed of ITO or IZO. Such a conductive layer enables electron-injecting properties of the anode to be improved.

Further, a conductive layer may be provided on the side of the anode which is in contact with the substrate in order to improve adhesion between the anode and the substrate. Examples of such a conductive layer include transparent conductive materials such as ITO and IZO.

If a display formed of the organic EL device is an active matrix type drive display, the anode is patterned for each pixel, and provided in such a manner that it is connected to a thin film transistor provided on the substrate. In this case, an insulative film is provided on the anode such that the surface of the anode for each pixel is exposed through an opening of the insulative film.

The anode can be formed by forming these electrode materials into a thin film by deposition, sputtering or the like.

The sheet resistance of the anode is preferably several hundreds Ω/□ or less. The film thickness of the anode, which varies depending upon the material thereof, is usually from 10 nm to 1 μm, preferably from 10 to 200 nm.

[Emitting Layer]

The emitting layer of the organic EL device has the following functions in combination.
(1) Injection function: function of allowing injection of holes from the anode or hole-injecting/transporting layer and injection of electrons from the cathode or electron-injecting/transporting layer upon application of an electric field
(2) Transporting function: function of moving injected carriers (electrons and holes) due to the force of an electric field
(3) Emitting function: function of allowing electrons and holes to recombine to emit light Note that electrons and holes may be injected into the emitting layer with different degrees, or the transportation capabilities indicated by the mobility of holes and electrons may differ. It is preferable that the emitting layer move either electrons or holes.

As the method of forming the emitting layer, a known method such as deposition, spin coating, or an LB method may be applied. It is preferable that the emitting layer be a molecular deposition film.

The term "molecular deposition film" refers to a thin film formed by depositing a vapor-phase material compound or a film formed by solidifying a solution-state or liquid-phase material compound. The molecular deposition film is distinguished from a thin film (molecular accumulation film) formed using the LB method by the difference in aggregation structure or higher order structure or the difference in function ascribable to the difference in structure.

The emitting layer may also be formed by dissolving a binder such as a resin and a material compound in a solvent to obtain a solution, and forming a thin film from the solution by spin coating or the like, as disclosed in JP-A-57-51781.

As the material used for the first emitting layer, a known long-lived luminescent material may be used. It is preferable to use a material of the general formula (I) as the luminescent material.

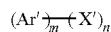

(I)

wherein Ar' is an aromatic ring having 6 to 50 nucleus carbon atoms or a heteroaromatic ring having 5 to 50 nucleus atoms.

As specific examples of Ar', a phenyl ring, a naphthyl ring, an anthracene ring, a biphenylene ring, an azulene ring, an acenaphthylene ring, a fluorene ring, a phenanthrene ring, a fluoranthene ring, an acephenanthrene ring, a triphenylene ring, a pyrene ring, a chrysene ring, a benzanthracene ring, a naphthacene ring, a picene ring, a perylene ring, a pentaphene ring, a pentacene ring, a tetraphenylene ring, a hexaphene ring, a hexacene ring, a rubicene ring, a coronene ring, a trinaphthylene ring, a pyrrole ring, an indole ring, a carbazole ring, an imidazole ring, a benzimidazole ring, an oxadizole ring, a triazole ring, a pyridine ring, a quinoxaline ring, a quinoline ring, a pyrimidine ring, a triazine ring, a thiophene ring, a benzothiophene ring, a thianthrene ring, a furan ring, a benzofuran ring, a pyrazole ring, a pyrazine ring, a pyridazine ring, an indolizine ring, a quinazoline ring, a phenanthroline ring, a silole ring, a benzosilole ring, and the like can be given.

Ar' is preferably a phenyl ring, a naphthyl ring, an anthracene ring, an acenaphthylene ring, a fluorene ring, a phenanthrene ring, a fluoranthene ring, a triphenylene ring, a pyrene ring, a chrysene ring, a benzanthracene ring, or a perylene ring.

X' is a substituent.

In more detail, X' is a substituted or unsubstituted aromatic group having 6 to 50 nucleus carbon atoms, a substituted or unsubstituted aromatic heterocyclic group having 5 to 50 nucleus atoms, a substituted or unsubstituted alkyl group having 1 to 50 carbon atoms, a substituted or unsubstituted alkoxy group having 1 to 50 carbon atoms, a substituted or unsubstituted aralkyl group having 1 to 50 carbon atoms, a substituted or unsubstituted aryloxy group having 5 to 50 nucleus atoms, a substituted or unsubstituted arylthio group having 5 to 50 nucleus atoms, a substituted or unsubstituted carboxyl group having 1 to 50 carbon atoms, a substituted or unsubstituted styryl group, a halogen atom, a cyano group, a nitro group, a hydroxyl group, or the like.

As examples of the substituted or unsubstituted aromatic group having 6 to 50 nucleus carbon atoms, a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, and 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-fluorenyl group, 9,9-dimethyl-2-fluorenyl group, 3-fluoranthenyl group, and the like can be given.

The substituted or unsubstituted aromatic group having 6 to 50 nucleus carbon atoms is preferably a phenyl group, 1-naphthyl group, 2-naphthyl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, o-tolyl group, m-tolyl group, p-tolyl group, p-t-butylphenyl group, 2-fluorenyl group, 9,9-dimethyl-2-fluorenyl group, 3-fluoranthenyl group, or the like.

As examples of the substituted or unsubstituted aromatic heterocyclic group having 5 to 50 nucleus atoms, a 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiadinyl group, 2-phenothiadinyl group, 3-phenothiadinyl group, 4-phenothiadinyl group, 10-phenothiadinyl group, 1-phenoxadinyl group, 2-phenoxadinyl group, 3-phenoxadinyl group, 4-phenoxadinyl group, 10-phenoxadinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butyl-pyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, and the like can be given.

As examples of the substituted or unsubstituted alkyl group having 1 to 50 carbon atoms, a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxy ethyl group, 2-hydroxyethyl group, 2-hydroxy isobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamantyl group, 2-adamantyl group, 1-norbornyl group, 2-norbornyl group, and the like can be given.

The substituted or unsubstituted alkoxy group having 1 to 50 carbon atoms is a group shown by —OY. As examples of Y, a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, and the like can be given.

Examples of the substituted or unsubstituted aralkyl groups having 1 to 50 carbon atoms include benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthyl isopropyl, 2-β-naphthyl isopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, and 1-chloro-2-phenylisopropyl groups.

The substituted or unsubstituted aryloxy group having 5 to 50 nucleus atoms is shown by —OY'. As examples of Y', a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl) phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiadinyl group, 2-phenothiadinyl group, 3-phenothiadinyl group, 4-phenothiadinyl group, 1-phenoxadinyl group, 2-phenoxadinyl group, 3-phenoxadinyl group, 4-phenoxadinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, and the like can be given.

The substituted or unsubstituted arylthio group having 5 to 50 nucleus atoms is shown by —SY". As examples of Y", a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl) phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiadinyl group, 2-phenothiadinyl group, 3-phenothiadinyl group, 4-phenothiadinyl group, 1-phenoxadinyl group, 2-phenoxadinyl group, 3-phenoxadinyl group, 4-phenoxadinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butyl-pyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, and the like can be given.

The substituted or unsubstituted carboxyl group having 1 to 50 carbon atoms is shown by —COOZ'. As examples of Z', a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, and the like can be given.

As examples of the substituted or unsubstituted styryl group, 2-phenyl-1-vinyl group, 2,2-diphenyl-1-vinyl group, 1,2,2-triphenyl-1-vinyl group, and the like can be given.

As examples of the halogen group, fluorine, chlorine, bromine, iodine, and the like can be given.

m is an integer of 1 to 5, and n is an integer of 0 to 6.

m is preferably 1 or 2, and n is preferably 0 to 4.

When m≥2, the Ar's in the parenthesis may be the same or different.

When n≥2, the X's in the parenthesis may be the same or different.

As the material used in the emitting layer, it is further preferable to use an anthracene derivative represented by the following formula (II).

$$A1-L-A2 \quad (II)$$

wherein A1 and A2 are independently a substituted or unsubstituted monophenylanthryl group or substituted or unsubstituted diphenylanthryl group, and may be the same or different; and L is a single bond or a divalent linking group.

In addition to the anthracene derivative described above, an anthracene derivative represented by the formula (III) can be given.

$$A3-An-A4 \quad (III)$$

wherein An is a substituted or unsubstituted divalent anthracene residue; and A3 and A4 are independently a substituted or unsubstituted monovalent condensed aromatic ring group or a substituted or unsubstituted non-condensed ring aryl group having 12 or more carbon atoms and may be the same or different.

As the anthracene derivative represented by the formula (II), an anthracene derivative represented by the following formula (II-a) can preferably be given.

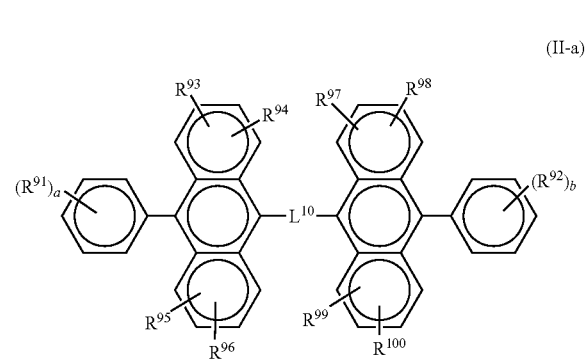

(II-a)

wherein $R^{91}$ to $R^{100}$ are independently a hydrogen atom, an alkyl group, a cycloalkyl group, a substituted or unsubstituted aryl group which may be substituted, an alkoxy group, an aryloxy group, an alkylamino group, an arylamino group or a heterocyclic group which may be substituted; a and b are independently an integer of 1 to 5; when they are 2 or more, $R^{91}$s or $R^{92}$s may be the same or different, or $R^{91}$s or $R^{92}$s may be bonded together to form a ring; $R^{93}$ and $R^{94}$, $R^{95}$ and $R^{96}$, $R^{97}$ and $R^{98}$, or $R^{99}$ and $R^{100}$ may be bonded together to form a ring; and $L^{10}$ is a single bond, —O—, —S—, —N(R)— (R is an alkyl group or a substituted or unsubstituted aryl group), or an arylene group.

An anthracene derivative represented by the following formula (II-b) can also preferably be given.

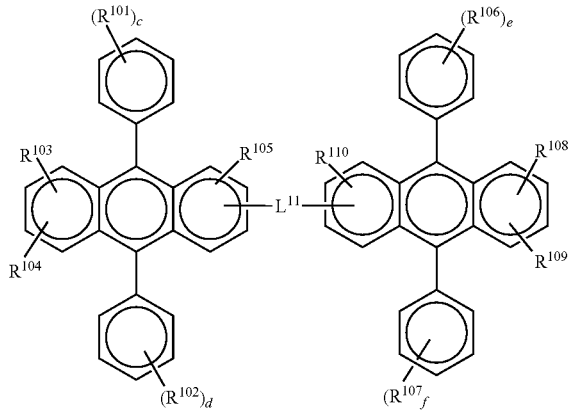

(II-b)

wherein $R^{101}$ to $R^{110}$ are independently a hydrogen atom, an alkyl group, a cycloalkyl group, a substituted or unsubstituted aryl group, an alkoxy group, an aryloxy group, an alkylamino group, an arylamino group or a substituted or unsubstituted heterocyclic group; c, d, e and f are independently an integer of 1 to 5; when they are 2 or more, $R^{101}$s, $R^{102}$s, $R^{106}$s or $R^{107}$s may be the same or different, $R^{101}$s, $R^{102}$s, $R^{106}$s or $R^{107}$s may be bonded together to form a ring, or $R^{103}$ and $R^{104}$, or $R^{108}$ and $R^{109}$ may be bonded together to form a ring; and $L^{11}$ is a single bond, —O—, —S—, —N(R)— (R is an alkyl group or an aryl group which may be substituted), or an arylene group.

As for $R^{91}$ to $R^{110}$ shown in the above formulae (II-a) and (II-b), as the alkyl group, an alkyl group having 1 to 6 carbon atoms, as the cyclo group, a cyclo alkyl group having 3 to 6 carbon atoms, as the aryl group, an aryl group having 5 to 18 carbon atoms, as the alkoxy group, an alkoxy group having 1 to 6 carbon atoms, as the aryoxy group, an aryloxy group having 5 to 18 carbon atoms, as the arylamino group, an amino group substituted with an aryl group having 5 to 16 carbon atoms, as the heterocyclic group, triazole, oxadiazole, quinoxaline, furanyl, or thienyl or the like can preferably be given.

It is preferred that the alkyl group represented by R in —N(R)— in $L^{10}$ and $L^{11}$ have 1 to 6 carbon atoms and that the ary group represented by R in —N(R)— in $L^{10}$ and $L^{11}$ have 5 to 18 carbon atoms.

As the host material for use in the emitting layer with a dopant which is described later, the compounds represented by the following formulas (i) to (ix) are preferred. Asymmetrical anthracene represented by the following formula (i)

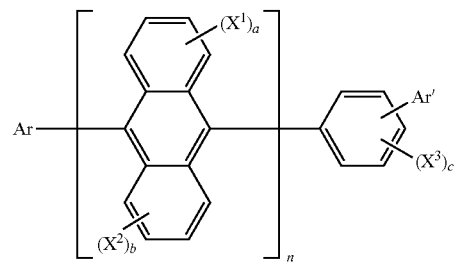

(i)

wherein Ar is a substituted or unsubstituted condensed aromatic group having 10 to 50 nucleus carbon atoms, Ar' is a substituted or unsubstituted aromatic group having 6 to 50 nucleus carbon atoms, $X^1$ to $X^3$ are independently a substituted or unsubstituted aromatic group having 6 to 50 nucleus carbon atoms, a substituted or unsubstituted aromatic heterocyclic group having 5 to 50 nucleus atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nucleus atoms, a substituted or unsubstituted arythio group having 5 to 50 nucleus atoms, a substituted or unsubstituted alkoxycarbonyl group having 1 to 50 carbon atoms, a carboxyl group, a halogen atom, a cyano group, a nitro group or a hydroxyl group; a, b and c are independently an integer of 0 to 4; and n is an integer of 1 to 3, provided that, when n is two or more, the groups in [ ] may be the same or different.

Asymmetrical monoanthracene derivatives represented by the following formula (ii)

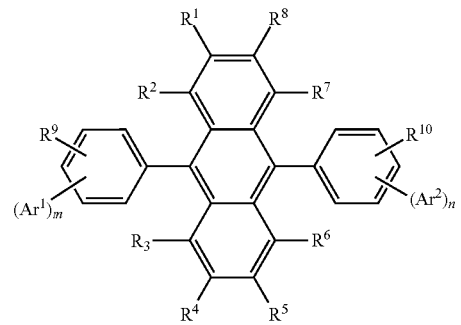

(ii)

wherein $Ar^1$ and $Ar^2$ are independently a substituted or unsubstituted aromatic ring group having 6 to 50 nucleus carbon atoms; and m and n are independently an integer of 1 to 4, provided that in the case where m=n=1 and $Ar^1$ and $Ar^2$ are symmetrically bonded to the benzene rings; $Ar^1$ and $Ar^2$ are not the same, and in the case where m or n is an integer of 2 to 4, m is different from n.

$R^1$ to $R^{10}$ are independently a hydrogen atom, a substituted or unsubstituted aromatic ring group having 6 to 50 nucleus carbon atoms, a substituted or unsubstituted aromatic hetrocyclic group having 5 to 50 nucleus atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nucleus atoms, a substituted or unsubstituted arylthio group having 5 to 50 nucleus atoms, a substituted or unsubstituted alkoxycarbonyl group having 1 to 50 carbon atoms, a substituted or unsubstituted silyl group, a carboxyl group, a halogen atom, a cyano group, a nitro group or a hydroxy group.

Asymmetrical pyrene derivatives represented by the following formula (iii)

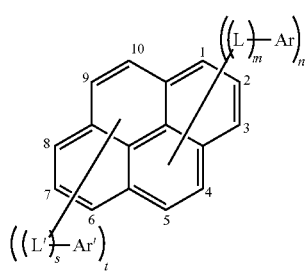

(iii)

wherein Ar and Ar' are independently a substituted or unsubstituted aromatic group having 6 to 50 nucleus carbon atoms; L and L' are independently a substituted or unsubstituted phenylene group, a substituted or unsubstituted naphthalenylene group, a substituted or unsubstituted fluolenylene group, or a substituted or unsubstituted dibenzosilolylene group;

m is an integer of 0 to 2, n is an integer of 1 to 4, s is an integer of 0 to 2, and t is an integer of 0 to 4;

L and Ar bonds at any one position of 1 to 5 of the pyrene; and L' or Ar' bonds at any one position of 6 to 10 of the pyrene; provided that when n+t is an even number, Ar, Ar', L and L' satisfy the following (1) or (2):

(1) Ar≠Ar' and/or L≠L' where ≠ means these are groups having different structures from each other.

(2) when Ar=Ar' and L=L', (2-1) m≠s and/or n≠t, or (2-2) when m=s and n=t, (2-2-1) when L, L' or pyrene bonds at different positions of Ar and Ar', or (2-2-2) L, L' or pyrene bonds at the same position of Ar and Ar', the substitution positions of L and L' or Ar and Ar' in the pyrene are not necessarily 1 and 6 positions or 2 and 7 positions.

Asymmetrical anthracene represented by the following formula (iv)

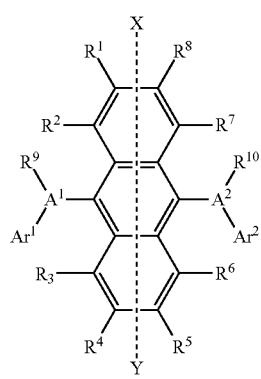

(iv)

wherein $A^1$ and $A^2$ are independently a substituted or unsubstituted condensed aromatic ring group having 10 to 20 nucleus carbon atoms;

$Ar^1$ and $Ar^2$ are independently a hydrogen atom or a substituted or unsubstituted aromatic ring group with 6 to 50 nucleus carbon atoms; and $R^1$ to $R^{10}$ are independently a hydrogen atom or a substituted or unsubstituted aromatic ring group having 6 to 50 nucleus carbon atoms, a substituted or unsubstituted aromatic hetrocyclic group having 5 to 50 nucleus atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nucleus atoms, a substituted or unsubstituted arylthio group having 5 to 50 nucleus atoms, a substituted or unsubstituted alkoxycarbonyl group having 1 to 50 carbon atoms, a substituted or unsubstituted silyl group, a carboxyl group, a halogen atom, a cyano group, a nitro group or a hydroxy group;

Each of $Ar^1$, $Ar^2$, $R^9$ and $R^{10}$ may be plural, and adjacent groups thereof may form a saturated or unsaturated ring structure.

However, in the formula, groups do not symmetrically bond to 9 and 10 positions of the central anthracene with respect to X-Y axis.

A small amount of a phosphor compound may be added to the emitting layer as a dopant to improve emission performance. Dopants known as a dopant material having a long lifetime may be used. It is preferable to use, as the dopant material of the luminescent material, a material represented by the formula (VI):

(IV)

In the formula, $Ar^{41}$ to $Ar^{43}$ are a substituted or unsubstituted aromatic group having 6 to 50 nucleus carbon atoms or a substituted or unsubstituted styryl group.

As examples of the substituted or unsubstituted aromatic group having 6 to 50 nucleus atoms, a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, and 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-fluorenyl group, 9,9-dimethyl-2-fluorenyl group, 3-fluoranthenyl group, and the like can be given.

The substituted or unsubstituted aromatic group having 6 to 50 nucleus atoms is preferably a phenyl group, 1-naphthyl group, 2-naphthyl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, o-tolyl group, m-tolyl group, p-tolyl group, p-t-butylphenyl group, 2-fluorenyl group, 9,9-dimethyl-2-fluorenyl group, 3-fluoranthenyl group, or the like.

As examples of the substituted or unsubstituted styryl group, 2-phenyl-1-vinyl group, 2,2-diphenyl-1-vinyl group, 1,2,2-triphenyl-1-vinyl group, and the like can be given.

p is an integer of 1 to 4.

When p≥2, the $Ar^{42}$ and $Ar^{43}$ in the parenthesis may be the same or different.

[Hole-Injecting/Transporting Layer]

The hole-injecting/transporting layer is a layer for helping the injection of holes into the emitting layer to transport the holes to a light-emitting region. The hole mobility thereof is large and the ionization energy thereof is usually as small as 5.6 eV or less. Such a hole-injecting/transporting layer is preferably made of a material which can transport holes to the emitting layer at a low electric field intensity. The hole mobility thereof is preferably at least $10^{-4}$ cm²/V·second when an electric field of, e.g., $10^4$ to $10^6$ V/cm is applied.

In the invention, the hole-injection layer and the hole-transporting layer may be formed of a plurality of layers. The compounds used in the device configuration of the invention, which are represented by the above formulas (1) and (2), may form a hole-injecting/transporting layer alone or in combination with other materials.

Any materials which have the above preferable properties can be used in combination with the compounds represented by the formulas (1) and (2), which are used in the device configuration of the invention, as the material for forming the hole-injecting/transporting layer without particular limitation. The material for forming the hole-injecting layer or the hole-transporting layer can be arbitrarily selected from materials which have been widely used as a material transporting carriers of holes in photoconductive materials and known materials used in a hole-injecting layer of organic EL devices. Other than the aromatic amine derivative layer and the nitrogen-containing heterocyclic derivative layer, layers constituting the hole-transporting region may be provided. The material forming such layers may be selected arbitrarily from the known materials as mentioned above. A compound represented by the following formula can be considered as the aromatic amine derivative.

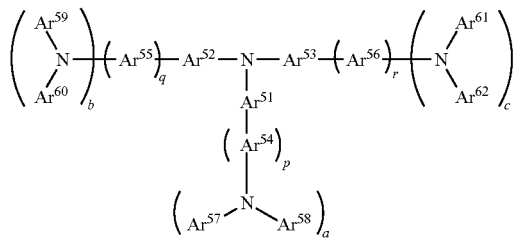

$Ar^{57}$ to $Ar^{62}$, $Ar^{51}$ to $Ar^{53}$, $Ar^{54}$ to $Ar^{56}$ are independently a substituted or unsubstituted aromatic group having 6 to 50 nucleus carbon atoms or a heteroaromatic group having 5 to 50 nucleus atoms; a to c, and p to r are independently an integer of 0 to 3; and $Ar^{57}$ and $Ar^{58}$, $Ar^{59}$ and $Ar^{60}$, and $Ar^{61}$ and $Ar^{62}$ may be bonded to each other to form a saturated or unsaturated ring.

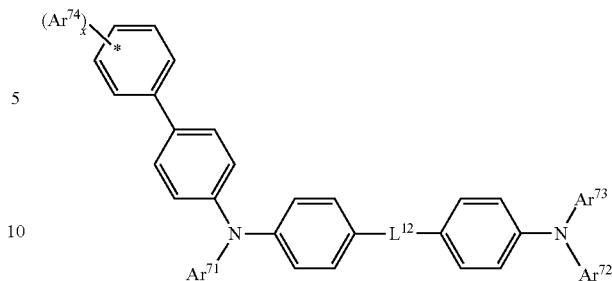

$Ar^{71}$ to $Ar^{74}$ are a substituted or unsubstituted aromatic group having 6 to 50 nucleus carbon atoms or a heteroaromatic group having 5 to 50 nucleus atoms; $L^{12}$ is a linking group, a single bond, a substituted or unsubstituted aromatic group having 6 to 50 nucleus carbon atoms, or a heteroaromatic group having 5 to 50 nucleus atoms; x is an integer of 0 to 5; and $Ar^{72}$ and $Ar^{73}$ may be bonded to each other to form a saturated or unsaturated ring.

Specific examples include triazole derivatives (see U.S. Pat. No. 3,112,197 and others), oxadiazole derivatives (see U.S. Pat. No. 3,189,447 and others), imidazole derivatives (see JP-B-37-16096 and others), polyarylalkane derivatives (see U.S. Pat. Nos. 3,615,402, 3,820,989 and 3,542,544, JP-B-45-555 and 51-10983, JP-A-51-93224, 55-17105, 56-4148, 55-108667, 55-156953 and 56-36656, and others), pyrazoline derivatives and pyrazolone derivatives (see U.S. Pat. Nos. 3,180,729 and 4,278,746, JP-A-55-88064, 55-88065, 49-105537, 55-51086, 56-80051, 56-88141, 57-45545, 54-112637 and 55-74546, and others), phenylene diamine derivatives (see U.S. Pat. No. 3,615,404, JP-B-51-10105, 46-3712, 47-25336, 54-119925, and others), arylamine derivatives (see U.S. Pat. Nos. 3,567,450, 3,240,597, 3,658,520, 4,232,103, 4,175,961 and 4,012,376, JP-B-49-35702 and 39-27577, JP-A-55-144250, 56-119132 and 56-22437, DE1,110,518, and others), amino-substituted chalcone derivatives (see U.S. Pat. No. 3,526,501, and others), oxazole derivatives (ones disclosed in U.S. Pat. No. 3,257,203, and others), styrylanthracene derivatives (see JP-A-56-46234, and others), fluorenone derivatives (JP-A-54-110837, and others), hydrazone derivatives (see U.S. Pat. No. 3,717,462, JP-A-54-59143, 55-52063, 55-52064, 55-46760, 57-11350, 57-148749 and 2-311591, and others), stilbene derivatives (see JP-A-61-210363, 61-228451, 61-14642, 61-72255, 62-47646, 62-36674, 62-10652, 62-30255, 60-93455, 60-94462, 60-174749 and 60-175052, and others), silazane derivatives (U.S. Pat. No. 4,950,950), polysilanes (JP-A-2-204996), aniline copolymers (JP-A-2-282263), and electroconductive high molecular oligomers (in particular thiophene oligomers).

The same substances used for the hole-transporting layer can be used as the material of the hole-injecting layer. The following can also be used: porphyrin compounds (disclosed in JP-A-63-295695 and others), aromatic tertiary amine compounds and styrylamine compounds (see U.S. Pat. No. 4,127,412, JP-A-53-27033, 54-58445, 55-79450, 55-144250, 56-119132, 61-295558, 61-98353 and 63-295695, and others). Aromatic tertiary amine compounds are particularly preferably used.

The following can also be given as examples: 4,4'-bis(N-(1-naphthyl)-N-phenylamino)biphenyl (abbreviated by NPD hereinafter), which has in the molecule thereof two condensed aromatic rings, disclosed in U.S. Pat. No. 5,061,569, and 4,4',4''-tris(N-(3-methylphenyl)-N-phenylamino)triphenylamine (abbreviated by MTDATA, hereinafter), wherein three triphenylamine units are linked to each other in a star-burst form, disclosed in JP-A-4-308688.

Other than those mentioned above, a nitrogen-containing heterocyclic derivative represented by the following formula, as disclosed in Japanese Patent No. 3571977, can also be used.

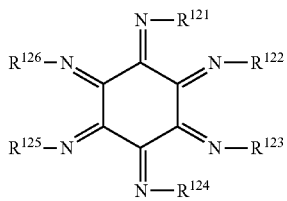

wherein $R^{121}$ to $R^{126}$ are independently a substituted or unsubstituted alkyl group, a substituted or unsubstituted aryl group, a substituted or unsubstituted aralkyl group, or a substituted or unsubstituted heterocyclic group. $R^{121}$ to $R^{126}$ may be the same or different. $R^{121}$ and $R^{122}$, $R^{123}$ and $R^{124}$, $R^{125}$ and $R^{126}$, $R^{121}$ and $R^{126}$, $R^{122}$ and $R^{123}$, and $R^{124}$ and $R^{125}$ may form a condensed ring.

Further, a compound represented by the following formula, as described in the U.S. Patent Publication No. 2004/0113547 can also be used.

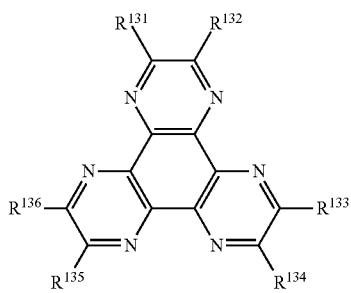

wherein $R^{131}$ to $R^{136}$ are a substituent, preferably an electron-attracting group such as a cyano group, a nitro group, a sulfonyl group, a carbonyl group, a trifluoromethyl group, or halogen.

The acceptor materials which are represented by these materials can also be used as the material for injecting holes. Specific examples thereof are the same as those mentioned above.

Inorganic compounds such as aromatic dimethylidene type compounds, mentioned above as the material for an emitting layer, and p-type Si and p-type SiC can also be used as the material of the hole-injecting layer.

The hole-injecting/transporting layer can be formed from the above-mentioned compounds by a known method such as vacuum vapor deposition, spin coating, casting or LB technique. The film thickness of the hole-injecting/transporting layer is not particularly limited, and is usually from 5 nm to 5 μm. This hole-injecting layer/transporting layer may be a single layer made of one or more of the above-mentioned materials, or may be stacked hole-injecting layers or hole-transporting layers made of different compounds, insofar as the compound of the invention is contained in the hole-transporting region.

Further, an organic semiconductor layer may be provided. The organic semiconductor layer is a layer for helping the injection of holes or electrons into the emitting layer, and is preferably a layer having an electric conductivity of $10^{-10}$ S/cm or more. As the material of such an organic semiconductor layer, electroconductive oligomers such as thiophene-containing oligomers or arylamine-containing oligomers disclosed in JP-A-8-193191, and electroconductive dendrimers such as arylamine-containing dendrimers may be used.

[Electron-Injecting/Transporting Layer]

The electron injecting/transporting layer is a layer which assists injection of electrons into the emitting layer, and exhibits a high electron mobility. An adhesion-improving layer is one of the electron-injecting layers and is formed of a material which exhibits excellent adhesion to the cathode. The material used in the electron-transporting layer is preferably a metal complex of 8-hydroxyquinoline or a derivative thereof.

As specific examples of a metal compled of 8-hydroxyquinoline and its derivative, metal chelate oxinoid compounds including a chelate of oxine (8-quinolinol or 8-hydroxyquinoline) can be given.

For example, Alq described as the luminescent material can be used for the electron-injecting layer.

An electron-transporting compound of the following general formula can be given as the oxadiazole derivative.

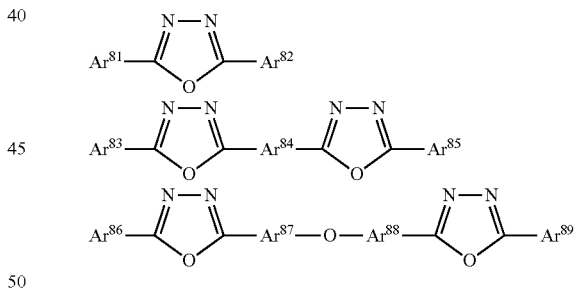

wherein $Ar^{81}$, $Ar^{82}$, $Ar^{83}$, $Ar^{85}$, $Ar^{86}$, and $Ar^{89}$ are independently substituted or unsubstituted aryl groups and may be the same or different; and $Ar^{84}$, $Ar^{87}$ and $Ar^{88}$ are a substituted or unsubstituted arylene group and may be the same or different.

As examples of the aryl group, a phenyl group, a biphenyl group, an anthranyl group, a perylenyl group, and a pyrenyl group can be given. As examples of the arylene group, a phenylene group, a naphthylene group, a biphenylene group, an anthranylene group, a perylenylene group, a pyrenylene group, and the like can be given. As the substituent, an alkyl group having 1 to 10 carbon atoms, an alkoxy group having 1 to 10 carbon atoms, a cyano group, and the like can be given. The electron-transporting compound is preferably one from which a thin film can be formed.

The following compounds can be given as specific examples of the electron-transporting compound.

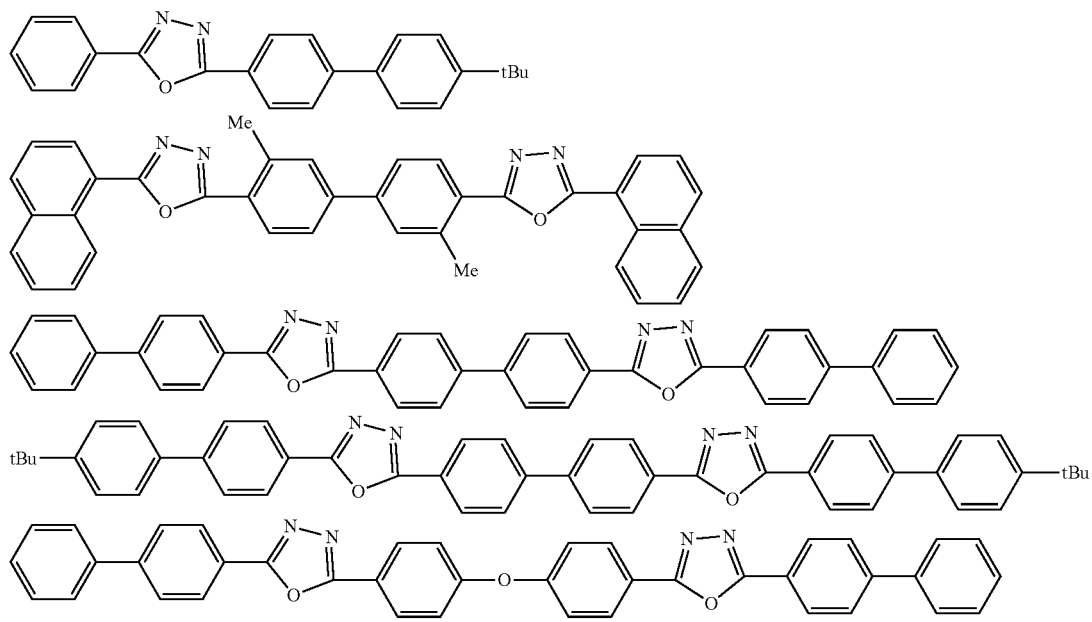

The nitrogen-containing heterocyclic derivatives represented by the following formulas (A) and (B) can be used in the electron-injecting layer.

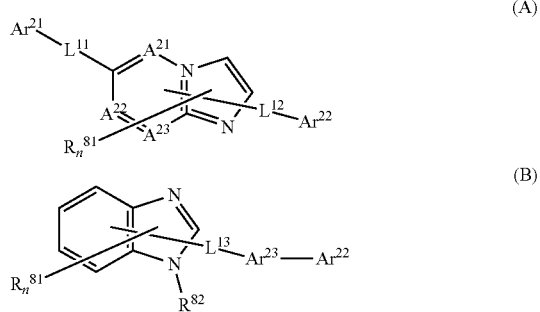

Nitrogen-containing heterocyclic ring derivatives represented by the formulas (A) and (B) wherein $A^{21}$ to $A^{23}$ are independently a nitrogen atom or a carbon atom; $Ar^{21}$ is a substituted or unsubstituted aryl group having 6 to 60 nucleus carbon atoms or a substituted or unsubstituted heteroaryl group having 3 to 60 nucleus carbon atoms; $Ar^{22}$ is a hydrogen atom, a substituted or unsubstituted aryl group having 6 to 60 nucleus carbon atoms, a substituted or unsubstituted heteroaryl group having 3 to 60 nucleus carbon atoms, a substituted or unsubstituted alkyl group having 1 to 20 carbon atoms, a substituted or unsubstituted alkoxy group having 1 to 20 carbon atoms, or a divalent group of these; provided that one of $Ar^{21}$ and $Ar^{22}$ is a substituted or unsubstituted condensed ring group having 10 to 60 carbon atoms or a substituted or unsubstituted monoheterocondensed ring group having 3 to 60 carbon atoms or a divalent group of these;

$Ar^{23}$ is a substituted or unsubstituted arylene group having 6 to 60 carbon atoms or a substituted or unsubstituted heteroarylene group having 3 to 60 carbon atoms;

$L^{11}$, $L^{12}$, and $L^{13}$ are independently a single bond, a substituted or unsubstituted arylene group having 6 to 60 carbon atoms, a substituted or unsubstituted heteroarylene group having 3 to 60 carbon atoms, or a substituted or unsubstituted fluorenylene group.

$R^{81}$ is a hydrogen atom, a substituted or unsubstituted aryl group having 6 to 60 nucleus carbon atoms, a substituted or unsubstituted heteroaryl group having 3 to 60 nucleus carbon atoms, a substituted or unsubstituted alkyl group having 1 to 20 carbon atoms, or a substituted or unsubstituted alkoxy group having 1 to 20 carbon atoms, and n is an integer of 0 to 5, provided that, when n is an integer of 2 or more, a plurality of $R^{81}$s may be the same or different; adjacent $R^{81}$s may be bonded to form a carbocyclic aliphatic ring or a carbocyclic aromatic ring;

$R^{82}$ is a hydrogen atom, a substituted or unsubstituted aryl group having 6 to 60 nucleus carbon atoms, a substituted or unsubstituted heteroaryl group having 3 to 60 nucleus carbon atoms, a substituted or unsubstituted alkyl group having 1 to 20 carbon atoms, a substituted or unsubstituted alkoxy group having 1 to 20 carbon atoms or -$L^{11}$-$Ar^{21}$—$Ar^{22}$.

Nitrogen-containing heterocyclic ring derivatives of the following formula (C)

wherein HAr is a nitrogen-containing heterocyclic ring having 3 to 40 carbon atoms which may have a substituent; $L^{14}$ is a single bond, an arylene group having 6 to 60 carbon atoms which may have a substituent, a heteroarylene group having 3 to 60 carbon atoms which may have a substituent or a fluorenylene group which may have a substituent; $Ar^{24}$ is a divalent aromatic hydrocarbon group having 6 to 60 carbon atoms which may have a substituent; and $Ar^{25}$ is an aryl group with 6 to 60 carbon atoms which may have a substituent or a heteroaryl group having 3 to 60 carbon atoms which may have a substituent.

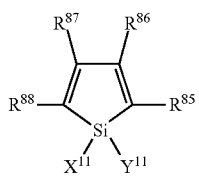

(D)

Silacyclopentadiene derivative represented by the formula (D) wherein $X^{11}$ and $Y^{11}$ are individually a saturated or unsaturated hydrocarbon group having 1 to 6 carbon atoms, an alkoxy group, an alkenyloxy group, an alkynyloxy group, a hydroxyl group, a substituted or unsubstituted aryl group, or a substituted or unsubstituted heterocyclic ring, or $X^{11}$ and $Y^{11}$ are bonded to form a saturated or unsaturated ring, and $R^{85}$ to $R^{88}$ are independently a hydrogen atom, a halogen atom, a substituted or unsubstituted aryl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group, or adjacent groups thereof form a substituted or unsubstituted condensed ring.

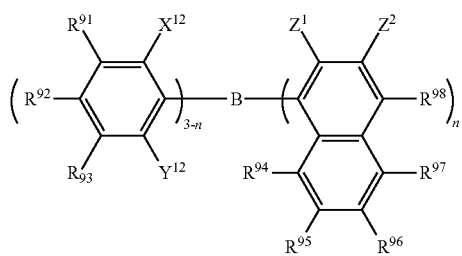

(E)

Boran derivative represented by the formula (E) wherein $R^{91}$ to $R^{98}$ and $Z^2$ are independently a hydrogen atom, a saturated or unsaturated hydrocarbon group, an aromatic group, a heterocyclic group, a substituted amino group, a substituted boryl group, an alkoxy group, or an aryloxy group, $X^{12}$, $Y^{12}$, and $Z^1$ are independently a saturated or unsaturated hydrocarbon group, an aromatic group, a heterocyclic group, a substituted amino group, an alkoxy group, or an aryloxy group, the substituents for $Z^1$ and $Z^2$ may be bonded to form a condensed ring, n is an integer of 1 to 3, provided that the $Z^1$s may differ when n is 2 or more, and a case in which n is 1, $X^{12}$, $Y^{12}$, and $R^{92}$ are methyl groups, and $R^{98}$ is a hydrogen atom or a substituted boryl group, and a case in which n is 3 and $Z_1$ is a methyl group are excluded.

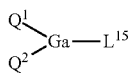

(F)

wherein $Q^1$ and $Q^2$ are independently ligands of the following formula (G), $L^{15}$ is a halogen atom, a substituted or unsubstituted alkyl group, a substituted or unsubstituted cycloalkyl group, a substituted or unsubstituted aryl group, a substituted or unsubstituted heterocyclic group, —OR' (R' is a hydrogen atom, a substituted or unsubstituted alkyl group, a substituted or unsubstituted cycloalkyl group, a substituted or unsubstituted aryl group, or a substituted or unsubstituted heterocyclic group), or —O-Ga-$Q^3(Q^4)$ ($Q^3$ and $Q^4$ have the same meanings as $Q^1$ and $Q^2$).

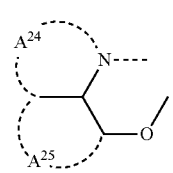

(G)

wherein rings $A^{24}$ and $A^{25}$ are independently a 6-membered aryl ring structure which may have a substituent, and are condensed to each other.

The metal complexes have the strong nature of an n-type semiconductor and large ability of injecting electrons. Further, the energy generated at the time of forming a complex is small so that a metal is then strongly bonded to ligands in the complex formed and the fluorescent quantum efficiency becomes large as the luminescent material.

Specific examples of the substituents for the rings $A^{24}$ and $A^{25}$ forming the ligand of the formula (G) include halogen atoms such as chlorine, bromine, iodine, and fluorine, substituted or unsubstituted alkyl groups such as a methyl group, ethyl group, propyl group, butyl group, sec-butyl group, tert-butyl group, pentyl group, hexyl group, heptyl group, octyl group, stearyl group, and trichloromethyl group, a substituted or unsubstituted aryl groups such as a phenyl group, naphthyl group, 3-methylphenyl group, 3-methoxyphenyl group, 3-fluorophenyl group, 3-trichloromethylphenyl group, 3-trifluoromethylphenyl group, and 3-nitrophenyl group, a substituted or unsubstituted alkoxy groups such as a methoxy group, n-butoxy group, tert-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, and 6-(perfluoroethyl)hexyloxy group, a substituted or unsubstituted aryloxy groups such as a phenoxy group, p-nitrophenoxy group, p-tert-butylphenoxy group, 3-fluorophenoxy group, pentafluorophenyl group, and 3-trifluoromethylphenoxy group, a substituted or unsubstituted alkylthio groups such as a methylthio group, ethylthio group, tert-butylthio group, hexylthio group, octylthio group, and trifluoromethylthio group, a substituted or unsubstituted arylthio groups such as a phenylthio group, p-nitrophenylthio group, p-tert-butylphenylthio group, 3-fluorophenylthio group, pentafluorophenylthio group, and 3-trifluoromethylphenylthio group, a cyano group, a nitro group, an amino group, mono- or di-substituted amino groups such as a methylamino group, diethylamino group, ethylamino group, diethylamino group, dipropylamino group, dibutylamino group, and diphenylamino group, acylamino groups such as a bis(acetoxymethyl)amino group, bis(acetoxyethyl)amino group, bis(acetoxypropyl)amino group, and bis(acetoxybutyl)amino group, a hydroxyl group, a siloxy group, an acyl group, a substituted or unsubstituted carbamoyl group such as a carbamoyl group, a methylcarbamoyl group, dimethylcarbamoyl group, ethylcarbamoyl group, diethylcarbamoyl group, propylcarbamoyl group, butylcarbamoyl group, and phenylcarbamoyl group, a carboxylic acid group, a sulfonic acid group, an imide group, cycloalkyl groups such as a cyclopentane group and a cyclohexyl group, aryl groups such as a phenyl group, naphthyl group, biphenyl group, anthranyl group, phenanthryl group, fluorenyl group, and pyrenyl group, heterocyclic groups such as a pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, carbazolyl group, furanyl group, thiophenyl group, oxazolyl group, triathinyl group, oxadiazolyl group, benzooxazolyl group, thiazolyl group, thiadiazolyl group, benzothiazolyl group, triazolyl group, imidazolyl group, benzimidazolyl group, pranyl group, and the like. The above substituents may be bonded to form a six-membered aryl ring or heterocyclic ring.

Polymer compounds containing a nitrogen-containing heterocyclic group or nitrogen-containing heterocyclic derivative may also be used.

A preferred embodiment of the invention is a device containing a reducing dopant in an interfacial region between its electron-transferring region or cathode and organic layer. The reducing dopant is defined as a substance which can reduce an electron-transferring compound. Accordingly, various substances which have given reducing properties can be used. For example, at least one substance can be preferably used which is selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, alkali metal organic complexes, alkaline earth metal organic complexes, and rare earth metal organic complexes.

More specific examples of the preferred reducing dopants include at least one alkali metal selected from the group consisting of Na (work function: 2.36 eV), K (work function: 2.28 eV), Rb (work function: 2.16 eV) and Cs (work function: 1.95 eV), and at least one alkaline earth metal selected from the group consisting of Ca (work function: 2.9 eV), Sr (work function: 2.0 to 2.5 eV), and Ba (work function: 2.52 eV). Metals having a work function of 2.9 eV or less are particularly preferred. Among these, a more preferable reducing dopant is at least one alkali metal selected from the group consisting of K, Rb and Cs. Even more preferable is Rb or Cs. Most preferable is Cs. These alkali metals are particularly high in reducing ability. Thus, the addition of a relatively small amount thereof to an electron-injecting zone improves the luminance of the organic EL device and make the lifetime thereof long. As a reducing agent having work function of 2.9 eV or less, combinations of two ore more alkali metals are preferable, particularly combinations including Cs, such as Cs and Na, Cs and K, Cs and Rb, or Cs, Na and K are preferable. The combination containing Cs makes it possible to exhibit the reducing ability efficiently. The luminance of the organic EL device can be improved and the lifetime thereof can be made long by the addition thereof to its electron-injecting zone.

In the invention, an electron-injecting layer of an insulator and a semiconductor may be further formed between a cathode and an organic layer. By forming the electron-injecting layer, a current leakage can be efficiently prevented and electron-injecting properties can be improved. As the insulator, at least one metal compound selected from the group consisting of alkali metal calcogenides, alkaline earth metal calcogenides, halides of alkali metals and halides of alkaline earth metals can be preferably used. When the electron-injecting layer is formed of the alkali metal calcogenide or the like, the injection of electrons can be preferably further improved.

Specifically preferable alkali metal calcogenides include $Li_2O$, LiO, $Na_2S$, $Na_2Se$ and NaO and preferable alkaline earth metal calcogenides include CaO, BaO, SrO, BeO, BaS and CaSe. Preferable halides of alkali metals include LiF, NaF, KF, LiCl, KCl and NaCl. Preferable halides of alkaline earth metals include fluorides such as $CaF_2$, $BaF_2$, $SrF_2$, $MgF_2$ and $BeF_2$ and halides other than fluorides.

Semiconductors forming an electron-transporting layer include one or combinations of two ore more of oxides, nitrides, and oxidized nitrides containing at least one element of Ba, Ca, Sr, Yb, Al, Ga, In, Li, Na, Cd, Mg, Si, Ta, Sb and Zn. An inorganic compound forming an electron-transporting layer is preferably a microcrystalline or amorphous insulating thin film. When the electron-transporting layer is formed of the insulating thin films, more uniformed thin film is formed whereby pixel defects such as a dark spot are decreased. Examples of such an inorganic compound include the above-mentioned alkali metal calcogenides, alkaline earth metal calcogenides, halides of alkali metals, and halides of alkaline earth metals.

[Cathode]

For the cathode, the following may be used: an electrode substance made of a metal, an alloy or an electroconductive compound, or a mixture thereof which has a small work function (4 eV or less). Specific examples of the electrode substance include sodium, sodium-potassium alloy, magnesium, lithium, magnesium/silver alloy, aluminum/aluminum oxide, aluminum/lithium alloy, indium, and rare earth metals.

This cathode can be formed by making the electrode substances into a thin film by deposition, sputtering or some other method.

In the case where emission from the emitting layer is outcoupled through the cathode, it is preferred to make the transmittance of the cathode to the emission larger than 10%.

The sheet resistance of the cathode is preferably several hundreds $\Omega/\square$ or less, and the film thickness thereof is usually from 5 nm to 1 μm, preferably from 5 to 200 nm.

To make the cathode semi-transparent and semi-reflective, it will suffice that the film thickness of the above materials is adjusted.

[Insulative Layer]

In the organic EL device, pixel defects based on leakage or a short circuit are easily generated since an electric field is applied to the super thin film. In order to prevent this, it is preferred to insert an insulative thin layer between the pair of electrodes.

Examples of the material used in the insulative layer include aluminum oxide, lithium fluoride, lithium oxide, cesium fluoride, cesium oxide, magnesium oxide, magnesium fluoride, calcium oxide, calcium fluoride, cesium fluoride, cesium carbonate, aluminum nitride, titanium oxide, silicon oxide, germanium oxide, silicon nitride, boron nitride, molybdenum oxide, ruthenium oxide, and vanadium oxide.

A mixture or laminate thereof may be used.

Example of Fabricating Organic EL Device

The organic EL device can be fabricated by forming an anode, an emitting layer and, optionally forming a hole-injecting layer and an electron-injecting layer if necessary, and further forming a cathode by use of the materials and methods exemplified above. The organic EL device can be fabricated in the order reverse to the above, i.e., the order from a cathode to an anode.

An example of the fabrication of the organic EL device will be described below which has a structure wherein the following are successively formed on a transparent substrate: anode/hole-injecting layer/hole-transporting layer/emitting layer/electron-transporting layer/cathode.

First, a thin film made of an anode material is formed into a thickness of 1 μm or less, preferably 10 to 200 nm on an appropriate transparent substrate by deposition, sputtering or some other method, thereby forming an anode.

Next, a hole-injecting layer formed of the compound of the above formula (2) is provided. As described above, the hole-injecting layer can be formed by vacuum vapor deposition, spin coating, casting, LB technique, or some other method. Vacuum vapor deposition is preferred since a homogenous film is easily obtained and pinholes are not easily generated. In the case where the hole-injecting layer is formed by vacuum vapor deposition, conditions for the deposition vary depending upon a compound used (a material for the hole-injecting layer), a desired crystal structure or recombining structure of the hole-injecting layer, and others. In general, the conditions are preferably selected from the following: deposition source temperature of 50 to 450° C., vacuum degree of $10^{-7}$ to $10^{-3}$ torr, deposition rate of 0.01 to 50 nm/second, substrate temperature of −50 to 300° C., and film thickness of 5 nm to 5 μm.

On the hole-injecting layer, a hole-transporting layer formed of the compound represented by the above formula (1) is provided. The conditions and methods for forming the hole-transporting layer are the same as those for forming the hole-injecting layer.

Next, an emitting layer is formed on the thus-formed hole-transporting layer. The emitting layer can also be formed by making a desired organic luminescent material into a thin film by vacuum vapor deposition, sputtering, spin coating, casting or some other method. Vacuum vapor deposition is preferred since a homogenous film is easily obtained and pinholes are not easily generated. In the case where the emitting layer is formed by vacuum vapor deposition, conditions for the deposition, which vary depending on a compound used, can be generally selected from conditions similar to those for the hole-transporting layer.

Next, an electron-transporting layer is formed on this emitting layer. Like the hole-transporting layer and the emitting layer, the layer is preferably formed by vacuum vapor deposition because a homogenous film is required. Conditions for the deposition can be selected from conditions similar to those for the hole-transporting layer and the emitting layer.

Lastly, a cathode is stacked thereon to obtain an organic EL device.

The cathode is made of a metal, and vacuum vapor deposition or sputtering may be used. However, vacuum vapor deposition is preferred in order to protect underlying organic layers from being damaged when the cathode film is formed.

For the organic EL device fabrication that has been described above, it is preferred that the formation from the anode to the cathode is continuously carried out, using only one vacuuming operation.

The method for forming each of the layers in the organic EL device of the invention is not particularly limited. A known forming method such as vacuum vapor deposition or spin coating can be used. An organic thin film layer including the compound represented by the above formula (1) used in the organic EL device of the invention may be formed using a known method such as vacuum vapor deposition, molecular beam epitaxy (MBE), or a coating method using a solution in which the material is dissolved in a solvent, such as dipping, spin coating, casting, bar coating, or roll coating.

The film thickness of each of the organic layers in the organic EL device of the invention is not particularly limited. In general, defects such as pinholes are easily generated when the film thickness is too small. Conversely, when the film thickness is too large, a high applied voltage becomes necessary, leading to low efficiency. Usually, the film thickness is preferably in the range of several nanometers to one micrometer.

If a DC voltage is applied to the organic EL device, emission can be observed when the polarities of the anode and the cathode are positive and negative, respectively, and a DC voltage of 5 to 40 V is applied. When a voltage with an opposite polarity is applied, no electric current flows and hence, emission does not occur. If an AC voltage is applied, uniform emission can be observed only when the anode and the cathode have a positive polarity and a negative polarity, respectively. The waveform of the AC applied may be arbitrary.

EXAMPLES

The invention will be described in detail referring to the following examples, which should not be construed as limiting the scope of the invention.

Example 1

A glass substrate of 25 mm by 75 mm by 1.1 mm thick with an ITO transparent electrode (anode) (GEOMATEC CO., LTD.) was subjected to ultrasonic cleaning with isopropyl alcohol for 5 minutes, and cleaned with ultraviolet rays and ozone for 30 minutes. The resultant substrate with transparent electrode lines was mounted on a substrate holder in a vacuum deposition device. First, a film of the compound B-1 represented by the following formula was formed as the hole-injecting layer in a thickness of 60 nm so as to cover the transparent electrode on the surface where the transparent electrode lines were formed. Subsequently, a film of the compound A-10 represented by the following formula was formed on the B-1 film in a thickness of 20 nm as the hole-transporting layer.

On the A-10 film, a film of an anthracene derivative AN-1 and a styrylamine derivative D-1 represented by the following formulas (film thickness ratio: AN-1:D-1=40:2) was formed in a thickness of 40 nm to form a blue-emitting layer.

On the blue emitting layer, a film of an Alq represented by the following formula was formed as the electron-transporting layer in a thickness of 20 nm by deposition. Thereafter, an LiF film was formed in a thickness of 1 nm as the electron-injecting layer and metal Al was deposited in a thickness of 150 nm as a metal cathode, thereby fabricating an organic EL device.

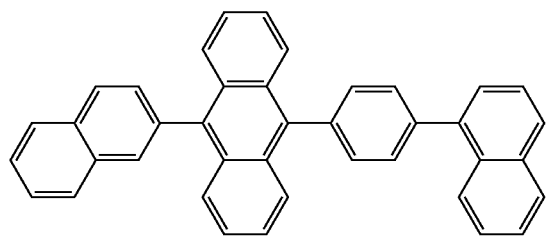

AN-1

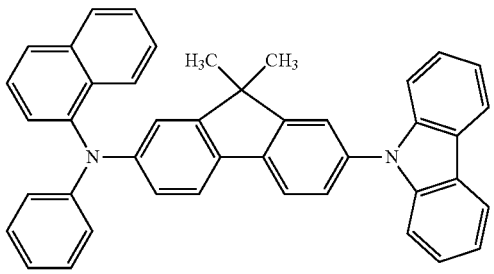

A-10

Example 2

An organic EL device was fabricated in the same manner as in Example 1, except that the compound A-2 represented by the following formula was used instead of the compound A-10 as the hole-transporting layer.

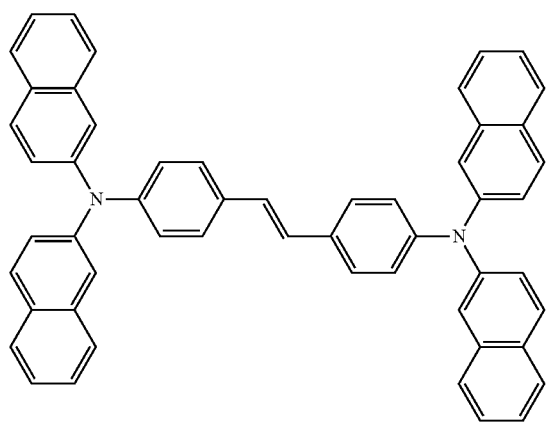

D-1

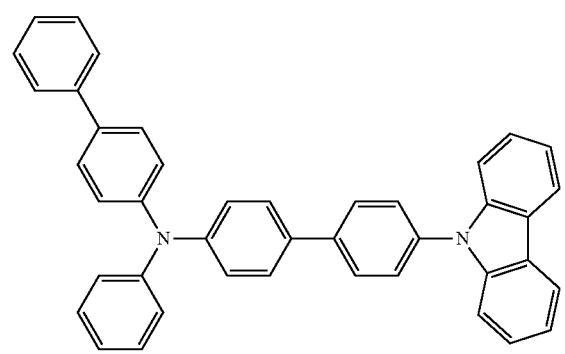

A-2

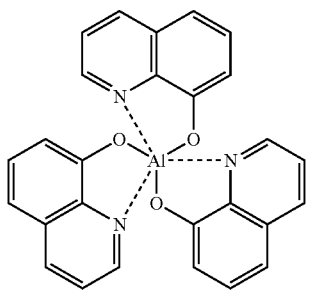

Alq

Example 3

An organic EL device was fabricated in the same manner as in Example 1, except that the compound A-6 represented by the following formula was used instead of the compound A-10 as the hole-transporting layer.

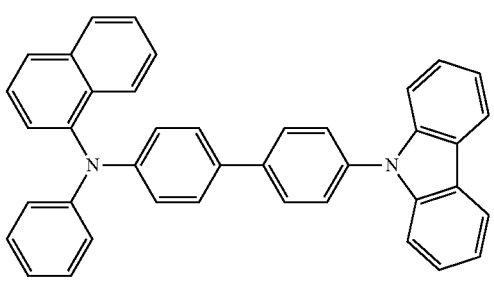

A-6

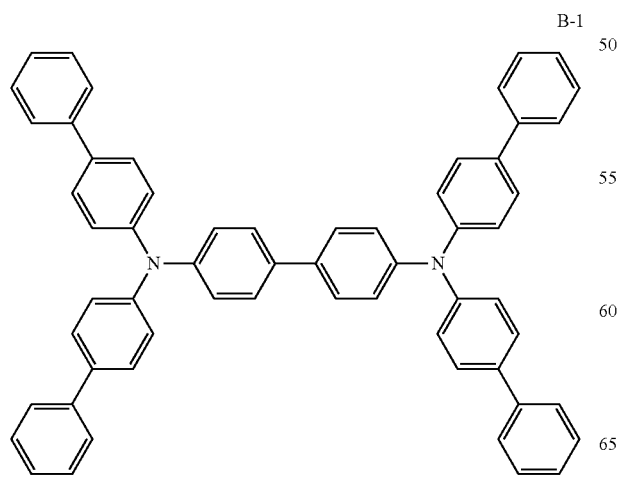

B-1

Example 4

An organic EL device was fabricated in the same manner as in Example 1, except that the compound A-9 represented by the following formula was used instead of the compound A-10 as the hole-transporting layer.

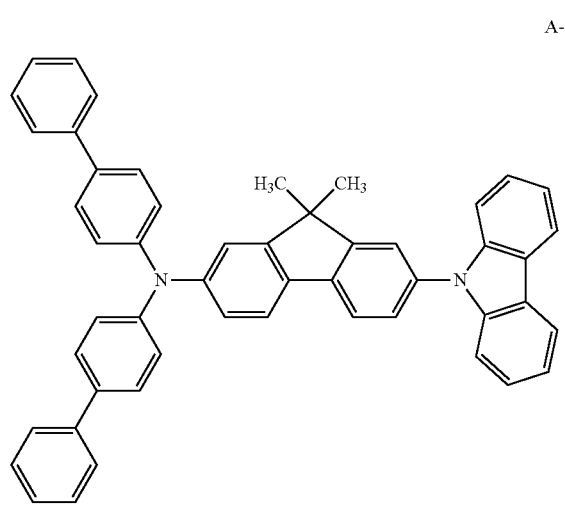

A-9

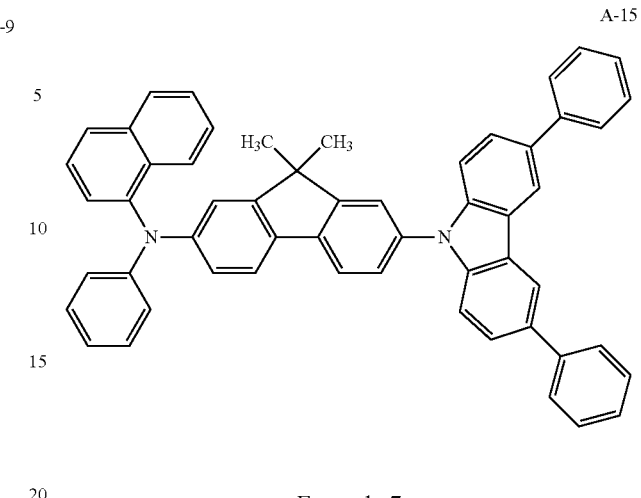

A-15

Example 5

An organic EL device was fabricated in the same manner as in Example 1, except that the compound A-11 represented by the following formula was used instead of the compound A-10 as the hole-transporting layer.

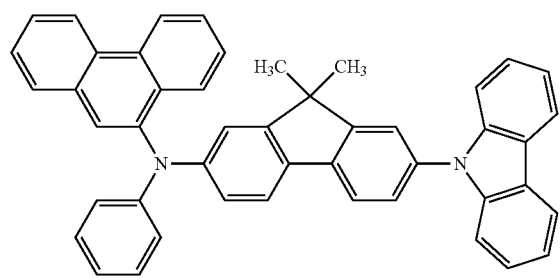

A-11

Example 6

An organic EL device was fabricated in the same manner as in Example 1, except that the compound A-15 represented by the following formula was used instead of the compound A-10 as the hole-transporting layer.

Example 7

An organic EL device was fabricated in the same manner as in Example 1, except that the compound A-25 represented by the following formula was used instead of the compound A-10 as the hole-transporting layer.

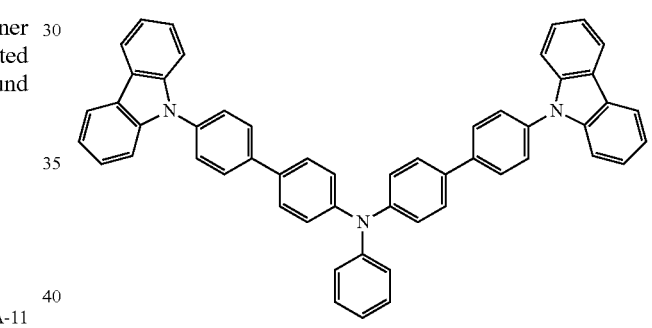

A-25

Example 8

An organic EL device was fabricated in the same manner as in Example 1, except that the compound A-26 represented by the following formula was used instead of the compound A-10 as the hole-transporting layer.

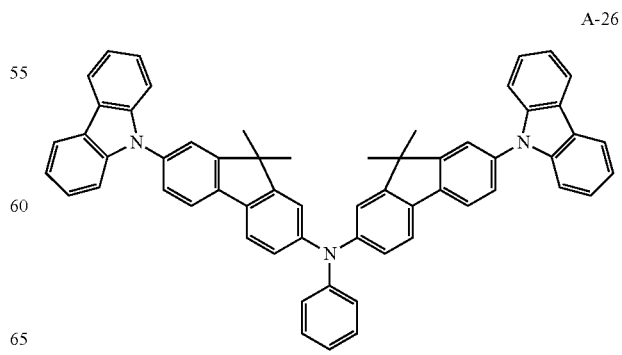

A-26

Example 9

An organic EL device was fabricated in the same manner as in Example 1, except that the compound A-28 represented by the following formula was used instead of the compound A-10 as the hole-transporting layer.

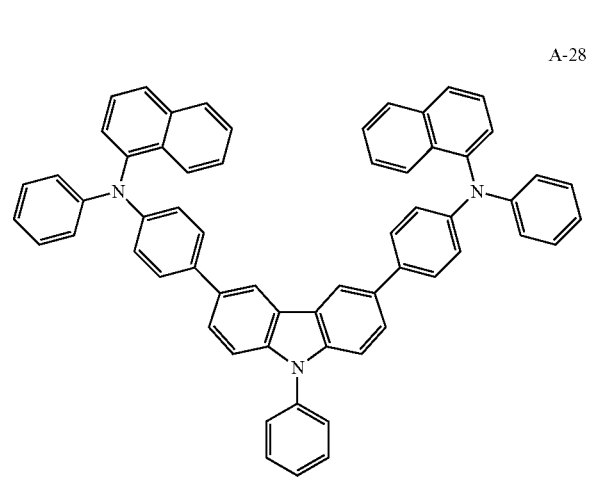 [SMILES: c1ccc(N(c2ccc(-c3ccc4c(c3)c3cc(-c5ccc(N(c6ccccc6)c6cccc7ccccc67)cc5)ccc3n4-c3ccccc3)cc2)c2cccc3ccccc23)cc1]

A-28

Example 10

An organic EL device was fabricated in the same manner as in Example 1, except that the compound A-29 represented by the following formula was used instead of the compound A-10 as the hole-transporting layer.

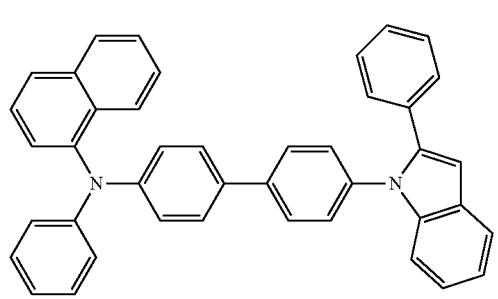

A-29

Example 11

An organic EL device was fabricated in the same manner as in Example 1, except that the compound B-5 represented by the following formula was used instead of the compound B-1 as the hole-injecting layer.

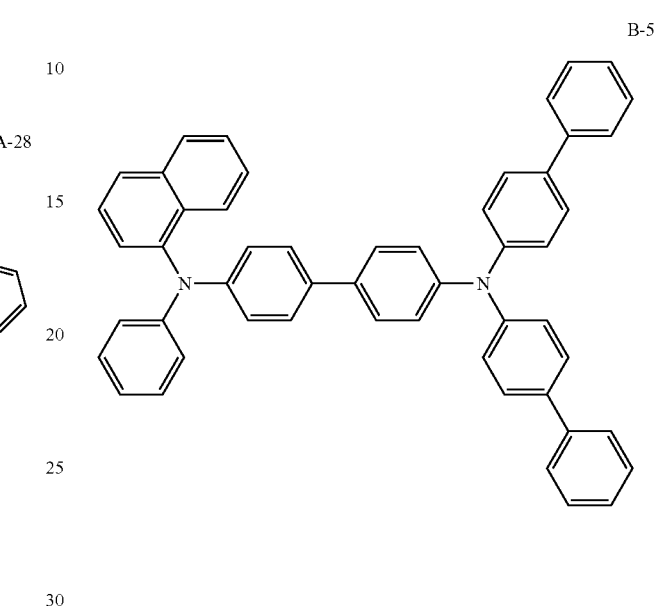

B-5

Example 12

An organic EL device was fabricated in the same manner as in Example 1, except that the compound B-7 represented by the following formula was used instead of the compound B-1 as the hole-injecting layer.

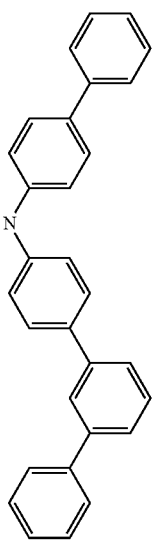

B-7

Example 13

An organic EL device was fabricated in the same manner as in Example 1, except that the compound B-8 represented by the following formula was used instead of the compound B-1 as the hole-injecting layer.

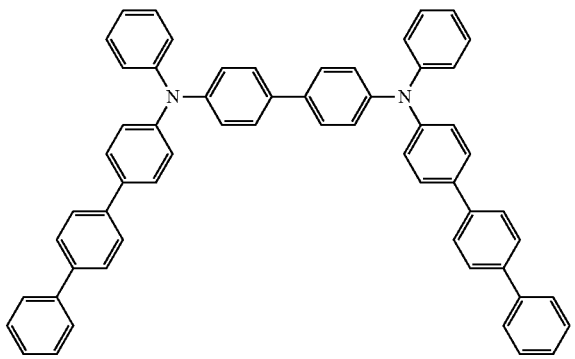

B-8

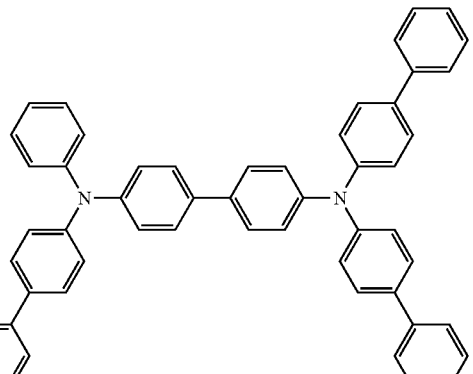

B-12

Example 14

An organic EL device was fabricated in the same manner as in Example 1, except that the compound B-12 represented by the following formula was used instead of the compound B-1 as the hole-injecting layer.

Example 15

An organic EL device was fabricated in the same manner as in Example 1, except that the compound B-25 represented by the following formula was used instead of the compound B-1 as the hole-injecting layer.

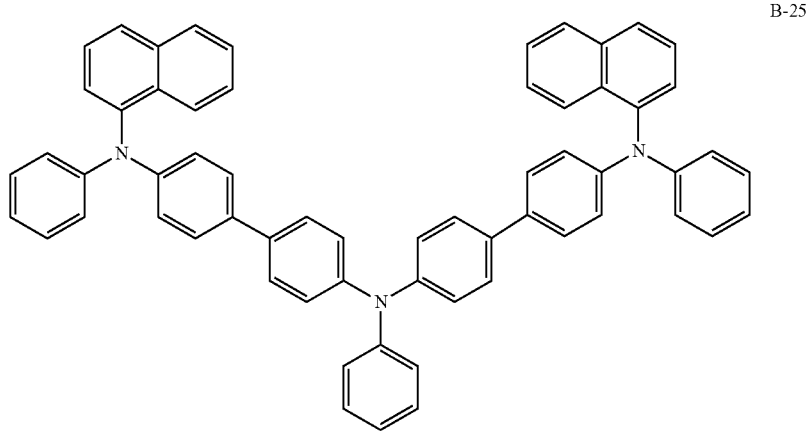 [SMILES: c1ccc(N(c2ccc(-c3ccc(N(c4ccccc4)c4cccc5ccccc45)cc3)cc2)c2ccc(-c3ccc(N(c4ccccc4)c4cccc5ccccc45)cc3)cc2)cc1]

B-25

Example 16

An organic EL device was fabricated in the same manner as in Example 1, except that the compound B-27 represented by the following formula was used instead of the compound B-1 as the hole-injecting layer.

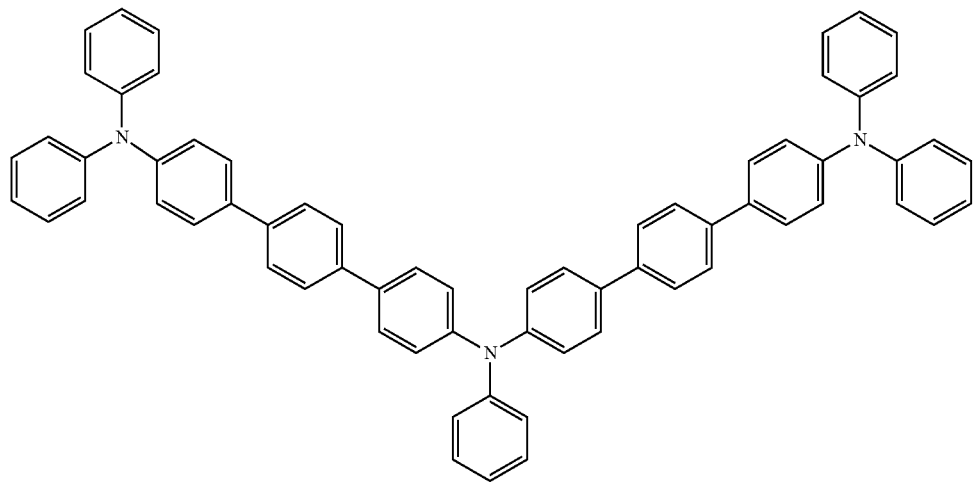

B-27

Example 17

An organic EL device was fabricated in the same manner as in Example 1, except that the compound B-33 represented by the following formula was used instead of the compound B-1 as the hole-injecting layer.

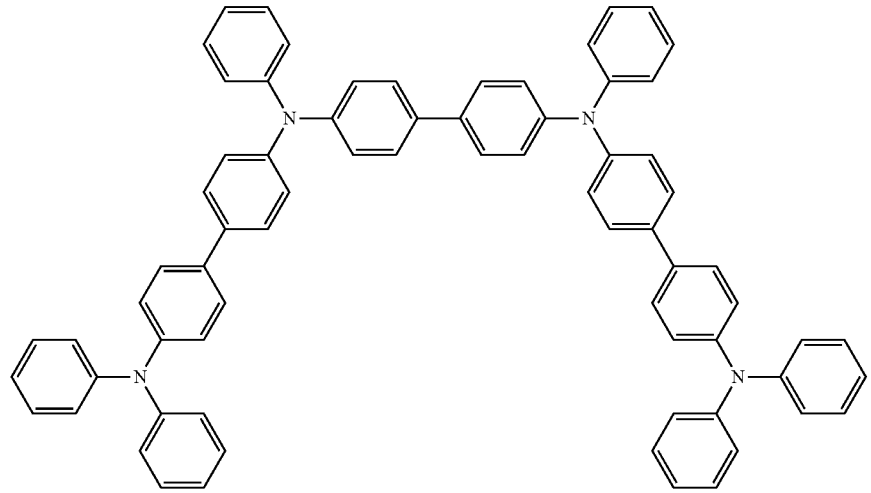

B-33

Example 18

An organic EL device was fabricated in the same manner as in Example 1, except that the compound B-39 represented by the following formula was used instead of the compound B-1 as the hole-injecting layer.

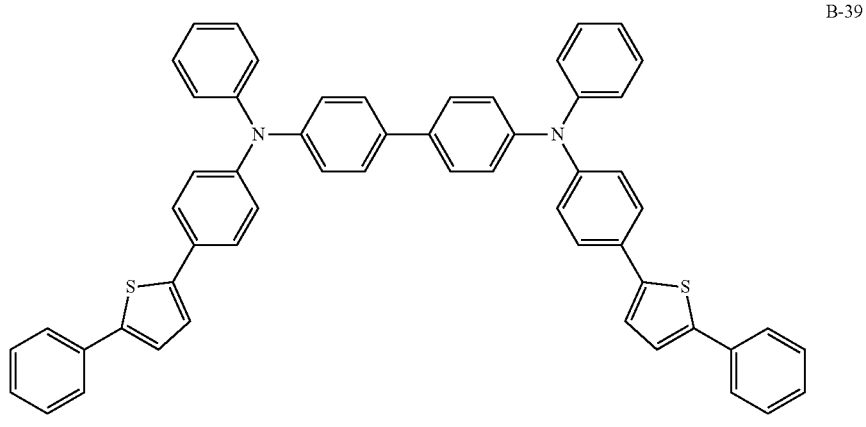 [SMILES: c1ccc(-c2ccc(-c3ccc(N(c4ccccc4)c4ccc(-c5ccc(N(c6ccccc6)c6ccc(-c7ccc(-c8ccccc8)s7)cc6)cc5)cc4)cc3)s2)cc1]

B-39

Comparative Example 1

An organic EL device was fabricated in the same manner as in Example 1, except that the compound (E-1) represented by the following formula was used instead of the compound A-10 as the hole-transporting layer.

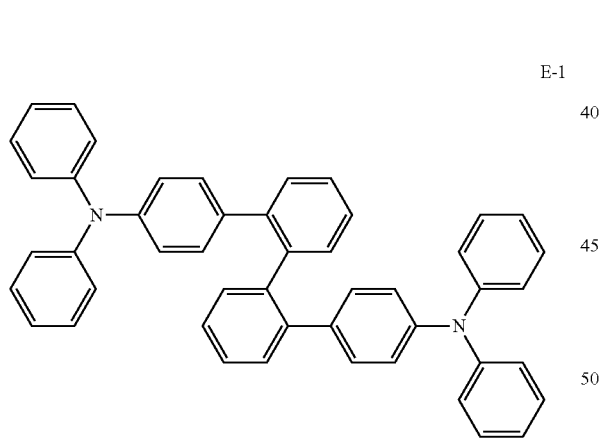

E-1

E-2

Comparative Example 2

An organic EL device was fabricated in the same manner as in Example 1, except that the compound E-2 represented by the following formula was used instead of the compound B-1 as the hole-injecting layer, and the compound B-1 was used instead of the compound A-10 as the hole-transporting layer.

Comparative Example 3

An organic EL device was fabricated in the same manner as in Example 1, except that the compound E-2 represented by the following formula was used instead of the compound B-1 as the hole-injecting layer.

Comparative Example 4

An organic EL device was fabricated in the same manner as in Example 1, except that the compound (E-3) represented by the following formula was used instead of the compound B-1 as the hole-injecting layer.

Comparative Example 5

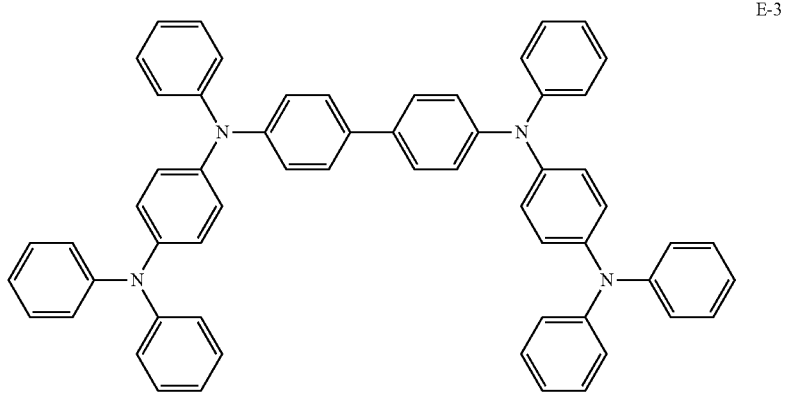 [SMILES: c1ccc(N(c2ccccc2)c2ccc(N(c3ccccc3)c3ccc(-c4ccc(N(c5ccccc5)c5ccc(N(c6ccccc6)c6ccccc6)cc5)cc4)cc3)cc2)cc1]

E-3

An organic EL device was fabricated in the same manner as in Example 1, except that the thickness of the hole-injecting layer formed of the compound B-1 was changed to 80 nm, and the hole-transporting layer was not formed.

Comparative Example 6

An organic EL device was fabricated in the same manner as in Comparative Example 5, except that the compound A-10 was used instead of the compound B-1 as the hole-injecting layer.

Comparative Example 7

An organic EL device was fabricated in the same manner as in Comparative Example 5, except that the compound B-39 was used instead of the compound B-1 as the hole-injecting layer.

The performance of each device fabricated in Examples 1 to 18 and Comparative Examples 1 to 7 is shown in Table 1.

TABLE 1

| | Hole-injecting layer | Hole-transporting layer | Voltage (V) | Luminous efficiency (cd/A) | Color of emitted light | Life time |
|---|---|---|---|---|---|---|
| Example 1 | 5-1 | A-10 | 6.9 | 8.2 | blue | 8000 |
| Example 2 | B-1 | A-2 | 7.1 | 8.3 | blue | 7000 |
| Example 3 | B-1 | A-6 | 7 | 8.3 | blue | 7000 |
| Example 4 | B-1 | A-9 | 6.9 | 8.3 | blue | 8000 |
| Example 5 | B-1 | A-11 | 6.9 | 8.2 | blue | 8000 |
| Example 6 | B-1 | A-15 | 6.9 | 8.3 | blue | 8000 |
| Example 7 | B-1 | A-25 | 7.1 | 8.3 | blue | 8000 |
| Example 8 | B-1 | A-26 | 7 | 8.2 | blue | 8000 |
| Example 9 | B-1 | A-28 | 7 | 8.2 | blue | 8000 |
| Example 10 | B-1 | A-29 | 7 | 8.2 | blue | 8000 |
| Example 11 | B-5 | A-10 | 6.9 | 8.3 | blue | 8000 |
| Example 12 | B-7 | A-10 | 6.9 | 8.3 | blue | 8000 |
| Example 13 | B-8 | A-10 | 6.9 | 8.3 | blue | 8000 |
| Example 14 | B-12 | A-10 | 6.9 | 8.3 | blue | 6000 |
| Example 15 | B-25 | A-10 | 6.9 | 8.3 | blue | 8000 |
| Example 16 | B-27 | A-10 | 6.9 | 8.3 | blue | 8000 |
| Example 17 | B-33 | A-10 | 6.9 | 8.3 | blue | 8000 |
| Example 18 | B-39 | A-10 | 6.9 | 8.2 | blue | 8000 |
| Comparative Example 1 | B-1 | E-1 | 7.3 | 6.7 | blue | 500 |
| Comparative Example 2 | E-2 | B-1 | 6.8 | 6.5 | blue | 8000 |
| Comparative Example 3 | E-2 | A-10 | 8.9 | 8.2 | blue | 500 |
| Comparative Example 4 | E-3 | A-10 | 8.5 | 8.3 | blue | 500 |
| Comparative Example 5 | B-1 | — | 6.8 | 6.5 | blue | 7000 |
| Comparative Example 6 | A-10 | — | 10.5 | 8.3 | blue | 500 |
| Comparative Example 7 | B-39 | — | 6.5 | 4.1 | blue | 600 |

Example 19

A glass substrate of 25 mm by 75 mm by 1.1 mm thick with an ITO transparent electrode (anode) (GEOMATEC CO., LTD.) was subjected to ultrasonic cleaning with isopropyl alcohol for 5 minutes, and cleaned with ultraviolet rays and ozone for 30 minutes. The resultant substrate with transparent electrode lines was mounted on a substrate holder in a vapor vacuum deposition device. First, a film of an acceptor compound C-1 represented by the following formula was formed in a thickness of 10 nm as the hole-injecting layer so as to cover the transparent electrode on the surface where the transparent electrode lines were formed.

Subsequently, on the C-1 film, a film of the compound B-1 was formed in a thickness of 50 nm as the hole-transporting layer (1).

Then, on the B-1 film, a film of the compound A-10 was formed in a thickness of 20 nm as the hole-transporting layer (2).

Further, on the A-10 film, a film of AN-1 and D-1 (film thickness ratio: AN-1:D-1=40:2) was formed in a thickness of 40 nm to form a blue-emitting layer.

On the blue-emitting layer, a 20-thick Alq film was formed by deposition. Thereafter, an LiF film was formed in a thickness of 1 nm as an electron-injecting layer and metal Al was deposited in a thickness of 150 nm as a metal cathode thereon, thereby fabricating an organic EL device.

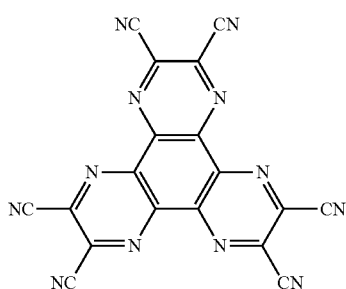

C-1

Example 20

An organic EL device was fabricated in the same manner as in Example 19, except that the compound C-2 represented by the following formula was used instead of the compound C-1 as the hole-injecting layer.

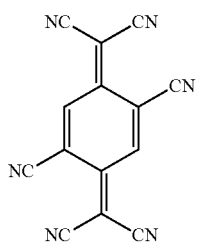

C-2

Example 21

An organic EL device was fabricated in the same manner as in Example 19, except that the compound A-2 was used instead of the compound A-10 as the hole-transporting layer (2).

Example 22

An organic EL device was fabricated in the same manner as in Example 19, except that the compound A-6 was used instead of the compound A-10 as the hole-transporting layer (2).

Example 23

An organic EL device was fabricated in the same manner as in Example 19, except that the compound A-9 was used instead of the compound A-10 as the hole-transporting layer (2).

Example 24

An organic EL device was fabricated in the same manner as in Example 19, except that the compound A-11 was used instead of the compound A-10 as the hole-transporting layer (2).

Example 25

An organic EL device was fabricated in the same manner as in Example 19, except that the compound A-15 was used instead of the compound A-10 as the hole-transporting layer (2).

Example 26

An organic EL device was fabricated in the same manner as in Example 19, except that the compound A-25 was used instead of the compound A-10 as the hole-transporting layer (2).

Example 27

An organic EL device was fabricated in the same manner as in Example 19, except that the compound A-26 was used instead of the compound A-10 as the hole-transporting layer (2).

Example 28

An organic EL device was fabricated in the same manner as in Example 19, except that the compound A-28 was used instead of the compound A-10 as the hole-transporting layer (2).

Example 29

An organic EL device was fabricated in the same manner as in Example 19, except that the compound A-29 was used instead of the compound A-10 as the hole-transporting layer (2).

Example 30

An organic EL device was fabricated in the same manner as in Example 19, except that the compound (B-2) was used instead of the compound B-1 as the hole-transporting layer (1).

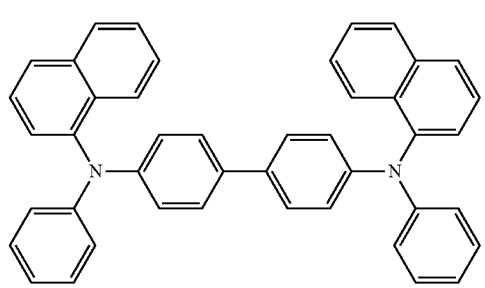

B-2

Example 31

An organic EL device was fabricated in the same manner as in Example 19, except that the compound B-5 was used instead of the compound B-1 as the hole-transporting layer (1).

Example 32

An organic EL device was fabricated in the same manner as in Example 19, except that the compound B-7 was used instead of the compound B-1 as the hole-transporting layer (1).

Example 33

An organic EL device was fabricated in the same manner as in Example 19, except that the compound B-8 was used instead of the compound B-1 as the hole-transporting layer (1).

Example 34

An organic EL device was fabricated in the same manner as in Example 19, except that the compound B-12 was used instead of the compound B-1 as the hole-transporting layer (1).

Example 35

An organic EL device was fabricated in the same manner as in Example 19, except that the compound B-25 was used instead of the compound B-1 as the hole-transporting layer (1).

Example 36

An organic EL device was fabricated in the same manner as in Example 19, except that the compound B-33 was used instead of the compound B-1 as the hole-transporting layer (1).

Example 37

An organic EL device was fabricated in the same manner as in Example 19, except that the compound B-39 was used instead of the compound B-1 as the hole-transporting layer (1).

Comparative Example 8

An organic EL device was fabricated in the same manner as in Example 19, except that the compound E-2 was used instead of the compound B-1 as the hole-transporting layer (1).

Comparative Example 9

An organic EL device was fabricated in the same manner as in Example 19, except that the compound E-3 was used instead of the compound B-1 as the hole-transporting layer (1).

Comparative Example 10

An organic EL device was fabricated in the same manner as in Example 19, except that the compound E-3 was used instead of the compound B-1 as the hole-transporting layer (1), and the compound B-1 was used instead of the compound A-10 as the hole-transporting layer (2).

Comparative Example 11

A glass substrate of 25 mm by 75 mm by 1.1 mm thick with an ITO transparent electrode (anode) (GEOMATEC CO., LTD.) was subjected to ultrasonic cleaning with isopropyl alcohol for 5 minutes, and cleaned with ultraviolet rays and ozone for 30 minutes. The resultant substrate with transparent electrode lines was mounted on a substrate holder in a vacuum vapor deposition device. First, a film of the acceptor compound (C-1) was formed in a thickness of 60 nm as the hole-injecting layer so as to cover the transparent electrode on the surface where the transparent electrode lines were formed. Subsequently, on the C-1 film, a film of the compound A-10 was formed in a thickness of 20 nm as the hole-transporting layer.

Further, on the A-10 film, a film of AN-1 and D-1 (a film thickness ratio: AN-1:D-1=40:2) was formed in a thickness of 40 nm to form a blue-emitting layer.

On the blue emitting layer, a 20 nm-thick film of Alq was formed by deposition as the electron-transporting layer. Thereafter, an LiF film was formed in a thickness of 1 nm as an electron-injecting layer and metal Al was deposited thereon in a thickness of 150 nm as a metal cathode, thereby fabricating an organic EL device.

Comparative Example 12

An organic EL device was fabricated in the same manner as in Comparative Example 11, except that the compound B-1 was used instead of the compound A-10 as the hole-transporting layer.

Comparative Example 13

An organic EL device was fabricated in the same manner as in Comparative Example 11, except that the compound B-39 was used instead of the compound A-10 as the hole-transporting layer.

The performance of each device fabricated in Examples 19 to 37 and Comparative Examples 8 to 13 is shown in Table 2.

TABLE 2

| | Hole-injecting layer | Hole-transporting layer 1 | Hole-transporting layer 2 | Voltage (V) | Luminous efficiency (cd/A) | Color of emitted light | Life time |
|---|---|---|---|---|---|---|---|
| Example 19 | C-1 | B-1 | A-10 | 6.4 | 8.2 | blue | 8000 |
| Example 20 | C-2 | B-1 | A-10 | 6.4 | 8.2 | blue | 8000 |
| Example 21 | C-1 | B-1 | A-2 | 6.6 | 8.3 | blue | 7000 |
| Example 22 | C-1 | B-1 | A-6 | 6.5 | 8.3 | blue | 7000 |
| Example 23 | C-1 | B-1 | A-9 | 6.4 | 8.3 | blue | 8000 |
| Example 24 | C-1 | B-1 | A-11 | 6.4 | 8.2 | blue | 8000 |
| Example 25 | C-1 | B-1 | A-15 | 6.4 | 8.3 | blue | 8000 |
| Example 26 | C-1 | B-1 | A-25 | 6.6 | 8.3 | blue | 8000 |
| Example 27 | C-1 | B-1 | A-26 | 6.5 | 8.2 | blue | 8000 |
| Example 28 | C-1 | B-1 | A-28 | 6.5 | 8.2 | blue | 8000 |

TABLE 2-continued

| | Hole-injecting layer | Hole-transporting layer 1 | Hole-transporting layer 2 | Voltage (V) | Luminous efficiency (cd/A) | Color of emitted light | Life time |
|---|---|---|---|---|---|---|---|
| Example 29 | C-1 | B-1 | A-29 | 6.5 | 8.2 | blue | 8000 |
| Example 30 | C-1 | B-2 | A-10 | 6.4 | 8.3 | blue | 8000 |
| Example 31 | C-1 | B-5 | A-10 | 6.4 | 8.3 | blue | 8000 |
| Example 32 | C-1 | B-7 | A-10 | 6.4 | 8.3 | blue | 8000 |
| Example 33 | C-1 | B-8 | A-10 | 6.4 | 8.3 | blue | 8000 |
| Example 34 | C-1 | B-12 | A-10 | 6.4 | 8.3 | blue | 8000 |
| Example 35 | C-1 | B-25 | A-10 | 6.4 | 8.3 | blue | 8000 |
| Example 36 | C-1 | B-33 | A-10 | 6.4 | 8.3 | blue | 8000 |
| Example 37 | C-1 | B-39 | A-10 | 6.4 | 8.3 | blue | 8000 |
| Comp. Example 8 | C-1 | E-2 | A-10 | 8.9 | 8.2 | blue | 500 |
| Comp. Example 9 | C-1 | E-3 | A-10 | 8.9 | 8.2 | blue | 500 |
| Comp. Example 10 | C-1 | E-3 | B-1 | 6.9 | 6 | blue | 5000 |
| Comp. Example 11 | C-1 | | A-10 | 10.5 | 7.5 | blue | 500 |
| Comp. Example 12 | C-1 | | B-1 | 6.6 | 6.5 | blue | 7000 |
| Comp. Example 13 | C-1 | | B-39 | 6.3 | 3.9 | blue | 600 |

The physical properties of the representative materials used in Examples and Comparative Examples are shown in Table 3.

TABLE 3

| Compound | Ionization Potential (eV) | Electron affinity (eV) | Energy gap (eV) | Hole mobility (cm$^2$/Vs) |
|---|---|---|---|---|
| E-1 | 5.6 | 2.42 | 3.18 | $1 \times 10^{-4}$ |
| E-2 | 5.2 | 1.9 | 3.3 | $3 \times 10^{-4}$ |
| B-1 | 5.5 | 2.41 | 3.09 | $9 \times 10^{-4}$ |
| A-10 | 5.52 | 2.34 | 3.18 | $1 \times 10^{-4}$ |
| AN-1 | 5.7 | 2.7 | 3 | — |

As shown in Comparative Example 6, when the hole-transporting layer was formed of the compound A-10 as a single layer, although a higher efficiency could be obtained as compared with Comparative Example 4 where the compound B-1 was used, the driving voltage became high to shorten the device life.

As shown in Table 3, the compound A-10 has an extremely small hole mobility. Thus, its film thickness is increased with an increase in driving voltage. It can be assumed that, since the amount of holes injected in the emitting layer was reduced due to an increased driving voltage, electrons arrived even at the hole-transporting layer to deteriorate hole-transporting materials, thereby shortening the device life. As compared with the compound B-1, the compound A-10 had a slightly smaller electron affinity, and a higher electron-blocking property, and hence, could enhance efficiency.

If the hole-injecting layer was inserted as in Comparative Examples 3 and 4, the driving voltage was lowered as compared with the case where the hole-transporting layer formed of the compound A-10 was used as a single layer. However, the driving voltage was still higher as compared with the device fabricated in Comparative Example 1 which had a conventional device configuration. It can be assumed that the driving voltage could not be lowered sufficiently due to insufficient hole mobility of the compound E-2.

On the other hand, the devices fabricated in Examples 1 to 18 exhibited a high luminous efficiency and a prolonged device life without increasing the drive voltage. Use of the compound B-1 in the hole-injecting layer suppressed an increase in the driving voltage due to a high hole mobility of the compound B-1.

The results of Comparative Example 1 demonstrate that use of the compound E-1 increased driving voltage and shortened device life. The results show that the conventional stepwise setting of the ionization potential level of a hole-transporting material is not necessarily effective in realizing a low-voltage, highly-efficient, and long-lived device.

The organic EL device of the invention has a structure in which holes readily flow due to the use of specific materials, thereby significantly increasing the amount of holes injected in the emitting layer. In addition, electrons are prevented from reaching the hole-transporting layer, resulting in a prolonged device life. Moreover, a lower driving voltage and a more prolonged device life can be realized by maintaining the characteristic property of enhancing an efficiency of the compound A-10.

It can be assumed that the above-mentioned tendency can be observed when analogous compounds of each compound are used.

The similar tendency can be observed when an acceptor material is used at the interface of the anode. Use of an acceptor material resulted in a further lowered driving voltage.

INDUSTRIAL APPLICABILITY

The organic EL device of the invention can be used as an organic EL device which emits not only blue light but also various other colors, and is suitable for use in the fields of various displays, back light, light source, indicators, signboards, interiors and the like. It is particularly suitable for a display device of color displays.

What is claimed is:

1. A compound represented by the formula (7)

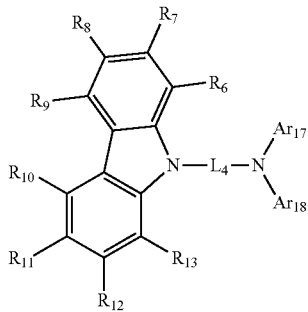

(7)

wherein
L$_4$ is a linking group selected from the group consisting of:

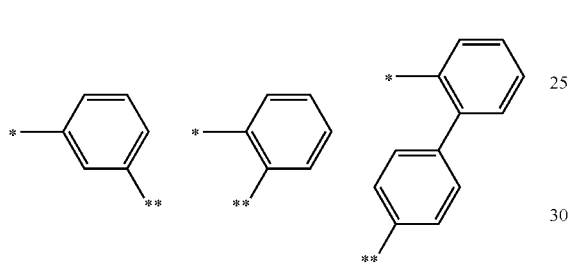

provided that a single asterisk (*) indicates the position bonding to the nitrogen atom of the carbazolyl group, and a double asterisk (**) indicates the position bonding to the nitrogen atom of N(Ar$_{17}$)(Ar$_{18}$), R$_6$ to R$_{13}$ are independently a hydrogen atom, or a phenyl group, Ar$_{17}$ is an unsubstituted phenylphenyl group, and Ar$_{18}$ is a phenylphenyl group which may be substituted by a phenyl group or a naphthyl group, or a phenyl group which may be substituted by a naphthyl group.

2. The compound according to claim 1, wherein Ar$_{18}$ is a 4-phenylphenyl group, which may be substituted by a phenyl group or a naphthyl group.

3. The compound according to claim 1, wherein Ar$_{18}$ is an unsubstituted 4-phenylphenyl group which may be substituted by a phenyl group.

4. The compound according to claim 1, wherein Ar$_{18}$ is an unsubstituted 4-phenylphenyl group.

5. The compound according to claim 1, wherein L$_4$ is a linking group of:

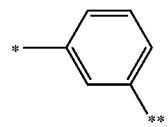

provided that a single asterisk (*) indicates the position bonding to the nitrogen atom of the carbazolyl group, and a double asterisk (**) indicates the position bonding to the nitrogen atom of N(Ar$_{17}$)(Ar$_{18}$).

6. The compound according to claim 1, wherein R$_6$ to R$_{13}$ are a hydrogen atom.

* * * * *